(12) United States Patent
Fu

(10) Patent No.: US 9,493,532 B2
(45) Date of Patent: Nov. 15, 2016

(54) COMPOSITIONS FOR CANCER THERAPY USING MUTANT LIGHT MOLECULES WITH INCREASED AFFINITY TO RECEPTORS

(71) Applicant: THE UNIVERSITY OF CHICAGO, Chicago, IL (US)

(72) Inventor: Yang-Xin Fu, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 14/363,243

(22) PCT Filed: Dec. 11, 2012

(86) PCT No.: PCT/US2012/069013
§ 371 (c)(1),
(2) Date: Jun. 5, 2014

(87) PCT Pub. No.: WO2013/090293
PCT Pub. Date: Jun. 20, 2013

(65) Prior Publication Data
US 2015/0056219 A1    Feb. 26, 2015

Related U.S. Application Data

(60) Provisional application No. 61/576,222, filed on Dec. 15, 2011.

(51) Int. Cl.
| C07K 14/525 | (2006.01) |
| A61K 47/48 | (2006.01) |
| C07K 14/625 | (2006.01) |
| A61K 45/06 | (2006.01) |

(52) U.S. Cl.
CPC ............ *C07K 14/525* (2013.01); *A61K 45/06* (2013.01); *A61K 47/48384* (2013.01); *A61K 47/48423* (2013.01); *A61K 47/48569* (2013.01); *A61K 47/48584* (2013.01); *A61K 47/48615* (2013.01); *C07K 14/625* (2013.01)

(58) Field of Classification Search
None
See application file for complete search history.

(56) References Cited

U.S. PATENT DOCUMENTS 7,811,983 B2 * 10/2010 Fu ................. A61K 39/0011
  424/184.1
8,263,081 B2 *  9/2012 Fu ................. A61K 47/48423
  424/178.1

FOREIGN PATENT DOCUMENTS

| WO | WO 01/79496 | 10/2001 |
| WO | WO 2005/002628 | 1/2005 |
| WO | WO 2008/144029 | 11/2008 |

OTHER PUBLICATIONS

Mauri et al., "Light, A new Member of the TNF Superfamily and Lymphotoxin Alpha Are Ligands for Herpesvirus Entry Mediator," *Imm., Cell Press*, 8(21): 21-30 (1998).
Zhai et al., Light, A Novel Ligand for Lymphotoxin Beta Receptor and TR2/HVEM Induces Apoptosis and Suppresses In Vivo Tumor Formation Via Gene Transfer, *J. Clin. Investigat. Amer. Soc. Clin. Invest.*, 102(6): 1142-1151 (1998).
Search Report & Written Opinion issued in App. No. PCT/US2012/069013 (2013).
Morishige et al., "Creation of a LIGHT mutant with the capacity to evade the decoy receptor for cancer therapy," *Biomaterials*, 31(12): 3357-3363 (2010).
Office Action issued in application No. JP 2014-547350 issued Oct. 14, 2015.

* cited by examiner

*Primary Examiner* — Elly-Gerald Stoica
(74) *Attorney, Agent, or Firm* — Casimir Jones SC; David W. Staple

(57) ABSTRACT

Methods and compositions are disclosed to target tumor cells with embodiments of the LIGHT proteins linked fused or conjugated to a targeting agent. These compositions bind to both human and mouse receptors with affinity sufficient to conduct preclinical and clinical trials, and with increased affinity as compared to the wild type human LIGHT protein. The targeting of embodiments of LIGHT to tumor cells reduces tumor growth and reduces metastases.

4 Claims, 46 Drawing Sheets

FIG. 6

| | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 |
|---|---|---|---|---|---|---|---|---|---|---|---|---|---|---|---|---|---|---|---|---|---|---|---|---|---|---|---|---|---|
| hLIGHT | R | R | S | H | E | V | N | P | A | A | H | L | T | G | A | N | S | S | L | T | G | S | G | G | P | L | L | W | E |
| mLIGHT | Q | R | | H | | | | | | | | L | T | | A | N | A | S | L | | | | | | P | L | L | W | |
| m3-11 | R | R | S | H | E | V | N | P | A | A | H | L | T | G | A | N | S | S | L | T | G | S | G | G | P | L | L | W | E |
| m4-4 | R | R | S | H | E | V | N | P | A | A | H | L | T | G | A | N | S | S | L | T | G | S | G | G | P | L | L | W | E |
| m3-6 | R | R | S | H | E | V | N | P | A | A | H | L | T | G | A | N | F | S | L | T | G | S | G | G | P | V | L | W | E |
| m4-1 | R | R | S | H | E | V | N | P | A | A | H | L | T | G | A | N | F | S | L | T | G | S | G | G | P | V | L | W | E |
| m3-9 | R | R | S | H | E | V | N | P | A | A | H | L | T | G | A | N | S | S | L | T | G | S | G | G | P | L | L | W | E |
| m3-7 | R | R | S | H | E | V | N | P | A | A | H | L | T | G | A | N | S | S | S | T | G | S | G | G | P | L | L | W | E |
| m4-5 | R | R | S | H | E | V | N | P | A | A | H | L | T | G | A | N | S | S | L | T | G | S | G | G | P | L | L | W | E |
| | R | R | S | H | E | V | N | P | A | A | H | L | T | G | A | N | F | S | L | T | G | S | G | G | P | L | L | W | E |
| m4-2 | R | R | S | H | E | V | N | P | A | A | H | L | T | G | A | N | F | S | L | T | G | S | G | G | P | L | L | W | E |
| | R | R | S | H | E | V | N | P | A | A | H | L | T | G | A | N | S | S | L | T | G | S | G | G | P | L | L | W | E |
| m4-10 | R | R | S | H | E | V | N | P | A | A | H | L | T | G | A | N | S | S | L | T | G | S | G | G | P | L | L | W | E |
| m3-20 | R | R | S | H | E | V | N | P | A | A | H | L | T | G | A | N | S | S | L | T | G | S | G | G | P | L | L | W | E |
| m3-13 | R | R | S | H | E | V | N | P | A | A | H | L | T | G | A | N | S | S | L | T | G | S | G | G | P | L | L | W | E |
| m4-26 | R | R | S | H | E | V | N | P | A | A | H | L | T | G | A | N | S | S | L | T | G | S | G | G | P | L | L | W | E |
| WMH-2 | R | R | S | H | E | V | N | P | A | A | H | L | T | G | A | N | S | S | L | T | G | S | G | G | P | L | L | W | E |
| WMH-3 | R | R | S | H | E | V | N | P | A | A | H | L | T | G | A | N | S | S | L | T | G | S | G | G | P | L | L | W | E |
| WMH-5 | R | R | S | H | E | V | N | P | A | A | H | L | T | G | A | N | S | S | L | T | G | S | G | G | P | L | L | W | E |
| WMH-6 | R | R | S | H | E | V | N | P | A | A | H | L | T | G | A | N | S | S | L | T | G | S | G | G | P | L | L | W | E |
| WMH-7 | R | R | S | H | E | V | N | P | A | A | H | L | T | G | A | N | S | S | L | T | G | S | G | G | P | L | L | W | E |
| WMH-9 | R | R | S | H | E | V | N | P | A | A | H | L | T | G | A | N | S | S | L | T | G | S | G | G | P | L | L | W | E |
| WMH-10 | R | R | S | H | E | V | N | P | A | A | H | L | T | G | A | N | S | S | L | T | G | S | G | G | P | L | L | W | E |
| WMH-13 | R | R | S | H | E | V | N | P | A | A | H | L | T | G | A | N | S | S | L | T | G | S | G | G | P | L | L | W | E |
| WMH-14 | R | G | S | H | E | V | N | P | A | A | H | L | T | G | A | N | S | S | L | T | G | S | G | G | P | L | L | W | E |
| WMH-19 | R | R | S | H | E | V | N | P | A | A | H | L | T | G | A | S | S | N | L | T | G | S | G | G | P | L | L | W | E |
| WMH-21 | R | R | S | H | E | V | N | P | A | A | H | L | T | G | A | N | S | S | L | T | G | S | G | G | P | L | L | W | E |
| WMH-27 | R | R | S | H | E | V | N | P | A | A | H | L | T | G | A | N | S | S | L | T | G | S | G | G | P | L | L | W | E |
| WMH-29 | Q | R | S | H | E | V | N | P | A | A | H | L | T | G | A | N | S | S | P | T | G | S | G | G | P | L | L | W | E |

| Pos | SEQ ID NO:43 | SEQ ID NO:44 | SEQ ID NO:6 | SEQ ID NO:7 | SEQ ID NO:8 | SEQ ID NO:8 | SEQ ID NO:9 | SEQ ID NO:10 | SEQ ID NO:10 | SEQ ID NO:4 | SEQ ID NO:3 | SEQ ID NO:5 | SEQ ID NO:5 | SEQ ID NO:11 | SEQ ID NO:12 | SEQ ID NO:13 | SEQ ID NO:12 | SEQ ID NO:14 | SEQ ID NO:15 | SEQ ID NO:16 | SEQ ID NO:17 | SEQ ID NO:20 | SEQ ID NO:19 | SEQ ID NO:20 | SEQ ID NO:21 | SEQ ID NO:22 | SEQ ID NO:23 | SEQ ID NO:45 | SEQ ID NO:20 | SEQ ID NO:25 |
|---|---|---|---|---|---|---|---|---|---|---|---|---|---|---|---|---|---|---|---|---|---|---|---|---|---|---|---|---|---|---|
| 218 | R | R | R | R | R | R | R | R | R | R | R | R | R | R | R | R | R | R | R | R | R | R | R | R | R | R | R | R | R | R |
| 219 | V |  | V | V | V | V | V | V | V | V | V | V | V | V | V | V | V | V | V | V | V | V | V | V | V | V | V | V | V | V |
| 220 | L | P | L | L | L | L | L | L | L | L | L | L | P | L | L | L | L | Q | L | L | L | Q | L | L | Q | L | L | L | L | L |
| 221 | D | G | D | D | D | D | D | D | D | D | D | D | D | D | D | D | D | G | D | G | D | D | D | D | D | D | D | G | D | D |
| 222 | E | N | E | E | E | E | E | E | E | E | D | D | E | E | E | E | E | E | E | E | K | E | K | E | E | E | E | K | E | E |
| 223 | R |  | R | R | R | R | R | R | R | R | R | R | R | R | R | R | R | R | R | R | R | R | R | R | R | R | R | R | R | R |
| 224 | L |  | L | L | L | L | L | L | L | L | L | L | L | L | L | L | L | L | L | L | L | L | L | L | L | L | L | L | L | L |
| 225 | V | V | D | V | V | V | V | V | V | V | V | V | V | V | V | A | V | V | V | V | V | V | V | V | V | V | V | V | V | V |
| 226 | R |  | R | R | R | R | R | R | R | R | R | R | R | R | R | R | R | R | R | R | R | R | R | R | R | R | R | R | R | R |
| 227 | L | P | L | L | L | L | L | L | L | L | L | L | L | L | L | L | L | Q | L | L | L | L | L | L | L | L | L | L | L | P |
| 228 | R | R | R | R | R | R | R | R | R | R | R | R | R | R | R | R | R | G | R | R | R | R | M | R | R | R | M | R | R | R |
| 229 | D |  | D | D | D | D | D | D | D | D | D | D | D | D | D | D | D | D | D | D | D | D | D | D | D | D | D | D | D | D |
| 230 | G |  | G | G | G | G | G | G | G | G | G | G | G | G | G | G | G | G | G | G | G | G | G | G | G | G | G | G | G | G |
| 231 | T |  | T | T | T | T | T | T | T | T | T | T | T | T | T | T | T | T | T | T | T | T | T | T | T | T | T | T | T | T |
| 232 | R |  | R | R | R | R | R | R | R | R | R | R | R | R | R | R | R | R | R | R | R | R | R | R | R | R | R | R | R | R |
| 233 | S |  | S | S | S | S | S | S | S | S | S | S | S | S | S | S | S | S | S | S | S | S | S | S | S | S | S | S | S | S |
| 234 | Y |  | Y | Y | Y | Y | Y | Y | Y | Y | Y | Y | Y | Y | Y | Y | Y | Y | Y | Y | Y | Y | Y | Y | Y | Y | Y | Y | Y | Y |
| 235 | F |  | F | F | F | F | F | F | F | F | F | F | F | F | F | F | F | F | F | F | F | F | F | F | F | F | F | F | F | F |
| 236 | G |  | G | G | G | G | G | G | G | G | G | G | G | G | G | G | G | G | G | G | G | G | G | G | G | G | G | G | G | G |
| 237 | A | A | A | A | A | A | A | A | A | A | A | A | A | A | A | A | A | A | A | A | A | A | A | A | A | A | A | A | A | A |
| 238 | F |  | F | F | F | F | F | F | F | F | F | F | F | F | F | F | F | F | F | F | F | F | F | F | F | F | F | F | F | F |
| 239 | M |  | M | M | M | M | M | M | M | M | M | M | M | M | M | M | M | M | M | M | M | M | M | M | M | M | M | M | M | M |
| 240 | V |  | V | V | V | V | V | V | V | V | V | V | V | V | V | V | V | V | V | V | V | V | V | V | V | V | V | V | V | V |

New human LIGHT mutants m3-11 (SEQ ID NO: 6)
RRSHEVNPAAHLTGANSSLTGSGGPLLWETQLGLAFLRGLSYHDGALVVTKAGYYYIYSKVQLRGVGCPLALASTITHGL
YKRTPRYPEELELLVSQQSPCGRATSSSRVWWDSSFLGGVVHLEAGEEVVVRVLDERLDLRDGTRSYFGAFMV m4-4 (SEQ ID NO: 7)
RRSHEVNPAAHLTGANSSLTGSGGPLLWETQLGLAFLRGLSYHDGALVATKAGYYYIYSKVQLGGVGCPLGLASTITHGL
YKRTPRYPEELELMVSQQSPCGRATSSSRVWWDSSFLGGVVHLEAGEEVVVRVPDERLVRLRDGTRSYFGAFMV m3-6 (SEQ ID NO: 8)
RRSHEVNPAAHLTGANFSLTGSGGPVLWETQLGLAFLRGLSYHDGALVVTKAGYYYIYSKLQLGGVGCPLGLAGTITHG
LYKRTPRYPEELELLVSQQSPCGRATSSSRAWWDSSFLGGVVHLEAGEEVVVRVLDERLVRLRDGTRSYFGAFMV m4-1 (SEQ ID NO: 8)
RRSHEVNPAAHLTGANFSLTGSGGPVLWETQLGLAFLRGLSYHDGALVVTKAGYYYIYSKLQLGGVGCPLGLAGTITHG
LYKRTPRYPEELELLVSQQSPCGRATSSSRAWWDSSFLGGVVHLEAGEEVVVRVLDERLVRLRDGTRSYFGAFMV m3-9 (SEQ ID NO: 9)
RRSHEVNPAAHLTGANSSLTGSGGPLLWETQLGLAFLRGLSYHDGALVVTKAGYYYIYSKVQLRGVGCPLGLASTITHGL
YKRTPRYPEELELLVNQQSPCGRAPSSSRVWWDSSFLGGVVHLEAGEEVVVRVLDERLVRLRDGTRSYFGAFMV m3-7 (SEQ ID NO: 10)
RRSHEVNPAAHLTGANSSLTGSGGPLLWETQLGLAFLRGLSYHDGALVVTKAGYYYIYSKVQLRGVGCPLGLASTIAHGL
YKRTPRYPEELELLVSQQSPCGRATSGSRVWWDSSFLGGVVHLEAGEEVVVRVLDERLVRLRDGTRSYFGAFMV m4-5 (SEQ ID NO: 10)
RRSHEVNPAAHLTGANSSLTGSGGPLLWETQLGLAFLRGLSYHDGALVVTKAGYYYIYSKVQLRGVGCPLGLASTIAHGL
YKRTPRYPEELELLVSQQSPCGRATSGSRVWWDSSFLGGVVHLEAGEEVVVRVLDERLVRLRDGTRSYFGAFMV m4-16 (SEQ ID NO: 4)
RRSHEVNPAAHLTGANSSSTGSGGPLLWETQLGLAFLRGLSYHDGALVVTKAGYYYIYSKVQLRGVGCPLGLASTITHGL
YKRTPRYPEELELLVSQQSPCGRATSSSRVWWDSSFLGGVVHLEAGEEVVVRVLDERLVRLRDGTRSYFGAFMV m4-14 (SEQ ID NO: 3)
RRSHEVNPAAHLTGANSSLTGSGGPLLWETQLGLAFLSGLSYHDGALVVTKAGYYYIYSKVQLRGVGCPLGLASTITHGL
YKRTPRYPEELELLVSQQSPCGRATSSSRVWWDSSFLGGVVHLEAGEEVVVRVLGERLVRLRDGTRSYFGAFMV m4-2 (SEQ ID NO: 5)
RRSHEVNPAAHLTGANFSLTGSGGPLLWETQLGQAFLRGLSYHDGALVVTKAGYYYIYSKVQLGGVGCPLGLASTITHG
LYKRTPRYPEELELLVSQQSPCGRATSSSRVWWDSSFLGGVVHLEAGEEVVVRVLDDRLVRLRDGTRSYFGAFMV

FIG. 7 m4-7 (SEQ ID NO: 5)
RRSHEVNPAAHLTGANFSLTGSGGPLLWETQLGQAFLRGLSYHDGALVVTKAGYYYIYSKVQLGGVGCPLGLASTITHG
LYKRTPRYPEELELLVSQQSPCGRATSSSRVWWDSSFLGGVVHLEAGEEVVVRVLDDRLVRLRDGTRSYFGAFMV m4-10 (SEQ ID NO: 11)
RRSHEVNPAAHLTGANSSLTGSGGPLLWETQLGLAFLRGLSYHDGALVVTKAGFYYIYSKVQLGGVGCPLGRASTITHG
LYKRTPRYPEELELLVSQQSPCGRATSSSRVWWDSSFLGGVVHLEAGEEVVVRVLDERLVRLRDGTRSYFGAFMV m3-20 (SEQ ID NO: 12)
RRSHEVNPAAHLTGANSSLTGSGGPLLWETQLGLAFLRGLSYHDGALVATKAGYYYIYSKVQLGGVGCPLGLASTISHGL
YKRTPRYPEELELLVSLRSPCGRATSSSRVWWDSSFLGGVVHLEAGEEVVVRVLDERLVRLRDGTRSYFGAFMV m3-13 (SEQ ID NO: 13)
RRSHEVNPAAHLTGANSSLTGSGGPLLWETQLGLAFLRGLSYHDGALVVTKAGYYYIYSKVQLGGVGCPLGLASTITHGL
YKRTPRYPEELELLVNQQSPCGRATSSSRVWWDSSFLGGVVHLEAGEEVVVRVPDERLVRLRDGTRSYFGAFMV m4-26 (SEQ ID NO: 12)
RRSHEVNPAAHLTGANSSLTGSGGPLLWETQLGLAFLRGLSYHDGALVATKAGYYYIYSKVQLGGVGCPLGLASTISHGL
YKRTPRYPEELELLVSLRSPCGRATSSSRVWWDSSFLGGVVHLEAGEEVVVRVLDERLVRLRDGTRSYFGAFMV

WMH-2 (SEQ ID NO: 14)
RRSHEVNPAAHLTGANSSLTGSGGPLLWETQLGQAFLRGLSYHDGALVVTKAGYYYIYSKVQLRGVGCPLGLASTITHG
LYKRTPRYPEELELLVSQQSPCGRATSSSRVWWDSSFLGGVVHLEAGEKVVVRVLDERLARLRDGTRSYFGAFMV

WMH-3 (SEQ ID NO: 15)
RRSHEVNPAAHLTGANSSLTGSGGPLLWETQLGQAFLRGLSYHDGALVVTKAGYYYIYSKVQLGGVGCPLGLANTITHG
LYKRTPRYPEELELLVSQQSPCGRATSSSRMWWDSSFLGGVVHLEAGEKVVVRVLDERLVRLRDGTRSYFGAFMV

WMH-5 (SEQ ID NO: 16)
RRSHEVNPAAHLTGANSSLTGSGGPLLWETQLGLAFLRGLSYHDGALVVTKAGYYYIYSKVQLRGVGCPLGLASPITHGL
YKRTPRYPEELELLVSQQSPCGRATSSSRVWWDSSFLGGVVHLEAGEKVVVRVLDERLVRQGDGTRSYFGAFMV

WMH-6 (SEQ ID NO: 17)
RRSHEVNPAAHLTGANSSLTGSGGPLLWETQLGLAFLRGLSYHDGALVVTKAGYYYIYSKVQLGGVGCPLGLASTFTHG
LYKRTPRYPEELELLVSQQSPCGRASSSSRVWWDSSFLGGVVHLEAGEKVVVRVLDERLVRLRDGTRSYFGAFMV

WMH-7 (SEQ ID NO: 20)
RRSHEVNPAAHLTGANSSLTGSGGPLLWETQLGLAFLRGLSYHDGALVVTKTGYYYIYSKVQLGGVGCPLGLAGTITHGL
YKRTPRYPEELELLVSQQSPCGRATSSSRVWWDSSFLGGVVHLEAGEKVVVRVLGKRLVRLRDGTRSYFGAFMV

FIG. 7 (Cont.)

WMH-9 (SEQ ID NO: 19)
RRSHEVNPAAHLTGANSNLTGSGGPLLWETQLGLAFLRGLSYHDGALVVTKAGYYYIYSKVQLGGVGCPLGLASTITHG
LYKRTPRYPEELELLVSQQSPCGRATSSSRVWWDSSFLGGVVHLEAGEKVVVRVQDERLVRLRDGTRSYFGAFMV

WMH-10 (SEQ ID NO: 20)
RRSHEVNPAAHLTGANSSLTGSGGPLLWETQLGLAFLRGLSYHDGALVVTKTGYYYIYSKVQLGGVGCPLGLAGTITHGL
YKRTPRYPEELELLVSQQSPCGRATSSSRVWWDSSFLGGVVHLEAGEKVVVRVLGKRLVRLRDGTRSYFGAFMV

WMH-13 (SEQ ID NO: 21)
RRSHEVNPAAHLTGANSSLTGSGGPLLWEPQLGLAFLRGLSYHDGALVVTKAGYYYIYSKVQLRGVGCPLGLTRTITHGL
YKRTPRYPEELELLVSQQSPCGRATPSSRVWWDSSFLGGVVHLEAGEKVVVRVLDERLVRLMDGTRSYFGAFMV

WMH-14 (SEQ ID NO: 22)
RGSHEVNPAAHLTGASSSLTGSGGPLLWETQLGLAFLRGLSYHDGALVVTKAGYYYIYSKVQLRGVGCPLGLASTITHGL
YKRTPRYPEELELLVSQQSPCGRATSSSRVWWDSSFLGGVVHLEAGEEVVVRVLDERLVRLRDGTRSYFGAFMV

WMH-19 (SEQ ID NO: 23)
RRSHEVNPAAHLTGANSSLTGSGGPLLWETQLGLAFLRGLSYHDGALVVTKAGYYYIYSKVQLGGVGCPLGRASTITHG
LYKRTPRYPEELELLVSQQSPCGRATSSSRVWWDSSFLGGVVHLEAGEKVVVRVQDERLVRLRDGTRSYFGAFMV

WMH-21 (SEQ ID NO: 45)
RRSHEVNPAAHLTGANSSLTGSGGPLLWETQLGLSFLRGLSYHDGALVVTKAGYYYIYSKVQLRGVGCPLGLASTITHGL
YKRTPRYPEELELLVSQQSPCGRATSSSRVWWDSSSLGGVVHLEAGEKVVVRVLDERLVRLMDGTRSYFGAFMV

WMH-27 (SEQ ID NO: 20)
RRSHEVNPAAHLTGANSSLTGSGGPLLWETQLGLAFLRGLSYHDGALVVTKTGYYYIYSKVQLGGVGCPLGLAGTITHGL
YKRTPRYPEELELLVSQQSPCGRATSSSRVWWDSSFLGGVVHLEAGEKVVVRVLGKRLVRLRDGTRSYFGAFMV

WMH-29 (SEQ ID NO: 25)
QRSHEVNPAAHLTGANSSPTGSGGPLLWETQLGLAFLRGLSYHDGALVVTKAGYYYIYSKVQLGGVGCPLGLASTITHG
LYKRTPRYPEELELLVSLQSPCGRATSSSRVWWDSSFLGGVVHLEAGEKVVVRVLDERLVRPRDGTRSYFGAFMV

FIG. 7(Cont.)

4T1=poorly immunogenic mammary carcinoma, metastisizes ~day 9-10

|        | wt   | m4-7  | m4-14 | m4-16 | m4-52 |
|--------|------|-------|-------|-------|-------|
| mLTbR  | TLD  | 0.118 | 0.094 | 0.192 | 0.68  |
| hLTbR  | 1.3  | 0.157 | 0.16  | 0.13  | 1.12  |
| mHVEM  | TLD  | 5.03  | 0.290 | 2.22  | 2.44  |
| hHVEM  | 1.5  | 0.92  | 38.5  | 2.24  | 1.42  |
| DcR3   | 0.6  | 3.83  | 2.45  | 1.12  | 0.27  |

[nM]

TLD= too low to determine hLIGHT EC domain

CGAAGGTCTCACGAGGTCAACCCAGCAGGCATCTCACAGGGCCAACTCCAGCTTGACCGGCAGCGGG
GGGCCGGCTGTTATGGGAGACTCAGGGCCTGGGCCTGGCCTTCCTGAGGGCCTCAGCTACCACGATGGGGCC
CTTGTGGTCACCAAAGCTGGCTACTACTACATCTACCAAGGTGCAGCTGGGCGGTGTGGGCTGCCCGC
TGGGCCTGGCCAGCACCATCACCCACGGCCTCTACAAGGCACACCAGCTCCCGGTCTGGTGGGACAGCAGCTT
GTTGGTCAGCAGCAGTCACCCTGCGGAGGGCCACCAGCAGCTCCCGGGTCTGGTGGGACAGCAGCTT
CCTGGGTGGTGTACACCTGGAGGCTGGGGAGAAGGTGGTCGTGTGCTGGATGAACGCCTGG
TTCGACTGCGTGATGGTACCCGGTCTTACTTCGGGGCTTTCATGGTGTGA (SEQ ID NO: 46)

hLIGHT M4-14

CGAAGGTCTCACGAGGTCAACCCAGCAGGCATCTCACAGGGCCAACTCCAGCTTGACCGGCAGCGGG
GGGCCGGCTGTTATGGGAGACTCAGGGCCTGGGCCTGGCCTTCCTGAGGGCCTCAGCTACCACGATGGGGCC
CTTGTGGTCACCAAAGCTGGCTACTACTACATCTACCAAGGTGCAGCTGGGCGGTGTGGGCTGCCCGC
TGGGCCTGGCCAGCACCATCACCCACGGCCTCTACAAGGCACACCAGCTCCCGGTCTGGTGGGACAGCAGCTT
GTTGGTCAGCAGCAGTCACCCTGCGGAGGGCCACCAGCAGCTCCCGGGTCTGGTGGGACAGCAGCTT
CCTGGGTGGTGTACACCTGGAGGAGGCTGGGGGAGGTGGTCGTGTGTTGGGTGAACGACTGG
TTCGACTGCGTGATGGTACCCGGTCTTACTTCGGGGCTTTCATGGTGtga (SEQ ID NO: 46)

FIG. 28

SEQUENCE LISTING

<160> NUMBER OF SEQ ID NOS: 47

<210> SEQ ID NO 1
<211> LENGTH: 4
<212> TYPE: PRT
<213> ORGANISM: Homo sapiens

<400> SEQUENCE: 1

Glu Gln Leu Ile
1

<210> SEQ ID NO 2
<211> LENGTH: 182
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Gln Leu His Trp Arg Leu Gly Glu Met Val Thr Arg Leu Pro Asp Gly
1               5                   10                  15

Pro Ala Gly Ser Trp Glu Gln Leu Ile Gln Glu Arg Arg Ser His Glu
            20                  25                  30

Val Asn Pro Ala Ala His Leu Thr Gly Ala Asn Ser Ser Leu Thr Gly
        35                  40                  45

Ser Gly Gly Pro Leu Leu Trp Glu Thr Gln Leu Gly Leu Ala Phe Leu
    50                  55                  60

Arg Gly Leu Ser Tyr His Asp Gly Ala Leu Val Val Thr Lys Ala Gly
65                  70                  75                  80

Tyr Tyr Tyr Ile Tyr Ser Lys Val Gln Leu Gly Gly Val Gly Cys Pro
                85                  90                  95

Leu Gly Leu Ala Ser Thr Ile Thr His Gly Leu Tyr Ile Cys Arg Thr
            100                 105                 110

Pro Arg Tyr Pro Glu Glu Leu Glu Leu Leu Val Ser Gln Gln Ser Pro
        115                 120                 125

Cys Gly Arg Ala Thr Ser Ser Ser Arg Val Trp Trp Asp Ser Ser Phe
    130                 135                 140

Leu Gly Gly Val Val His Leu Glu Ala Gly Glu Lys Val Val Val Arg
145                 150                 155                 160

Val Leu Asp Glu Arg Leu Val Arg Leu Arg Asp Gly Thr Arg Ser Tyr
                165                 170                 175

Phe Gly Ala Phe Met Val
            180

<210> SEQ ID NO 3
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Arg Arg Ser His Glu Val Asn Pro Ala Ala His Leu Thr Gly Ala Asn
1               5                   10                  15

Ser Ser Leu Thr Gly Ser Gly Gly Pro Leu Leu Trp Glu Thr Gln Leu
            20                  25                  30

```
Gly Leu Ala Phe Leu Ser Gly Leu Ser Tyr His Asp Gly Ala Leu Val
            35                  40                  45

Val Thr Lys Ala Gly Tyr Tyr Ile Tyr Ser Lys Val Gln Leu Arg
 50                  55                  60

Gly Val Gly Cys Pro Leu Gly Leu Ala Ser Thr Ile Thr His Gly Leu
 65                  70                  75                  80

Tyr Lys Arg Thr Pro Arg Tyr Pro Glu Glu Leu Glu Leu Leu Val Ser
                85                  90                  95

Gln Gln Ser Pro Cys Gly Arg Ala Thr Ser Ser Ser Arg Val Trp Trp
               100                 105                 110

Asp Ser Ser Phe Leu Gly Gly Val Val His Leu Glu Ala Gly Glu Glu
           115                 120                 125

Val Val Val Arg Val Leu Gly Glu Arg Leu Val Arg Leu Arg Asp Gly
       130                 135                 140

Thr Arg Ser Tyr Phe Gly Ala Phe Met Val
145                 150
```

<210> SEQ ID NO 4
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

```
Arg Arg Ser His Glu Val Asn Pro Ala Ala His Leu Thr Gly Ala Asn
  1               5                  10                  15

Ser Ser Ser Thr Gly Ser Gly Gly Pro Leu Leu Trp Glu Thr Gln Leu
             20                  25                  30

Gly Leu Ala Phe Leu Arg Gly Leu Ser Tyr His Asp Gly Ala Leu Val
            35                  40                  45

Val Thr Lys Ala Gly Tyr Tyr Ile Tyr Ser Lys Val Gln Leu Arg
 50                  55                  60

Gly Val Gly Cys Pro Leu Gly Leu Ala Ser Thr Ile Thr His Gly Leu
 65                  70                  75                  80

Tyr Lys Arg Thr Pro Arg Tyr Pro Glu Glu Leu Glu Leu Leu Val Ser
                85                  90                  95

Gln Gln Ser Pro Cys Gly Arg Ala Thr Ser Ser Ser Arg Val Trp Trp
               100                 105                 110

Asp Ser Ser Phe Leu Gly Gly Val Val His Leu Glu Ala Gly Glu Glu
           115                 120                 125

Val Val Val Arg Val Leu Asp Glu Arg Leu Val Arg Leu Arg Asp Gly
       130                 135                 140

Thr Arg Ser Tyr Phe Gly Ala Phe Met Val
145                 150
```

<210> SEQ ID NO 5
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Arg Arg Ser His Glu Val Asn Pro Ala Ala His Leu Thr Gly Ala Asn

```
            1               5                  10                 15
          Phe Ser Leu Thr Gly Ser Gly Gly Pro Leu Leu Trp Glu Thr Gln Leu
                          20                 25                 30

Gly Gln Ala Phe Leu Arg Gly Leu Ser Tyr His Asp Gly Ala Leu Val
                          35                 40                 45

Val Thr Lys Ala Gly Tyr Tyr Tyr Ile Tyr Ser Lys Val Gln Leu Gly
                          50                 55                 60

Gly Val Gly Cys Pro Leu Gly Leu Ala Ser Thr Ile Thr His Gly Leu
           65                 70                 75                 80

Tyr Lys Arg Thr Pro Arg Tyr Pro Glu Glu Leu Glu Leu Leu Val Ser
                          85                 90                 95

Gln Gln Ser Pro Cys Gly Arg Ala Thr Ser Ser Ser Arg Val Trp Trp
                         100                105                110

Asp Ser Ser Phe Leu Gly Gly Val Val His Leu Glu Ala Gly Glu Glu
                         115                120                125

Val Val Val Arg Val Leu Asp Asp Arg Leu Val Arg Leu Arg Asp Gly
                         130                135                140

Thr Arg Ser Tyr Phe Gly Ala Phe Met Val
          145                150
```

```
<210> SEQ ID NO 6
<211> LENGTH: 153
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Arg Arg Ser His Glu Val Asn Pro Ala Ala His Leu Thr Gly Ala Asn
  1               5                  10                 15

Ser Ser Leu Thr Gly Ser Gly Gly Pro Leu Leu Trp Glu Thr Gln Leu
                 20                 25                 30

Gly Leu Ala Phe Leu Arg Gly Leu Ser Tyr His Asp Gly Ala Leu Val
                 35                 40                 45

Val Thr Lys Ala Gly Tyr Tyr Tyr Ile Tyr Ser Lys Val Gln Leu Arg
                 50                 55                 60

Gly Val Gly Cys Pro Leu Ala Leu Ala Ser Thr Ile Thr His Gly Leu
 65                 70                 75                 80

Tyr Lys Arg Thr Pro Arg Tyr Pro Glu Glu Leu Glu Leu Leu Val Ser
                 85                 90                 95

Gln Gln Ser Pro Cys Gly Arg Ala Thr Ser Ser Ser Arg Val Trp Trp
                100                105                110

Asp Ser Ser Phe Leu Gly Gly Val Val His Leu Glu Ala Gly Glu Glu
                115                120                125

Val Val Val Arg Val Leu Asp Glu Arg Leu Asp Leu Arg Asp Gly Thr
                130                135                140

Arg Ser Tyr Phe Gly Ala Phe Met Val
145                 150
```

```
<210> SEQ ID NO 7
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic polypeptide"

<400> SEQUENCE: 7

Arg Arg Ser His Glu Val Asn Pro Ala Ala His Leu Thr Gly Ala Asn
1               5                   10                  15

Ser Ser Leu Thr Gly Ser Gly Gly Pro Leu Leu Trp Glu Thr Gln Leu
            20                  25                  30

Gly Leu Ala Phe Leu Arg Gly Leu Ser Tyr His Asp Gly Ala Leu Val
        35                  40                  45

Ala Thr Lys Ala Gly Tyr Tyr Tyr Ile Tyr Ser Lys Val Gln Leu Gly
    50                  55                  60

Gly Val Gly Cys Pro Leu Gly Leu Ala Ser Thr Ile Thr His Gly Leu
65                  70                  75                  80

Tyr Lys Arg Thr Pro Arg Tyr Pro Glu Glu Leu Glu Leu Met Val Ser
                85                  90                  95

Gln Gln Ser Pro Cys Gly Arg Ala Thr Ser Ser Ser Arg Val Trp Trp
            100                 105                 110

Asp Ser Ser Phe Leu Gly Gly Val Val His Leu Glu Ala Gly Glu Glu
        115                 120                 125

Val Val Val Arg Val Pro Asp Glu Arg Leu Val Arg Leu Arg Asp Gly
    130                 135                 140

Thr Arg Ser Tyr Phe Gly Ala Phe Met Val
145                 150

<210> SEQ ID NO 8
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Arg Arg Ser His Glu Val Asn Pro Ala Ala His Leu Thr Gly Ala Asn
1               5                   10                  15

Phe Ser Leu Thr Gly Ser Gly Gly Pro Val Leu Trp Glu Thr Gln Leu
            20                  25                  30

Gly Leu Ala Phe Leu Arg Gly Leu Ser Tyr His Asp Gly Ala Leu Val
        35                  40                  45

Val Thr Lys Ala Gly Tyr Tyr Tyr Ile Tyr Ser Lys Leu Gln Leu Gly
    50                  55                  60

Gly Val Gly Cys Pro Leu Gly Leu Ala Gly Thr Ile Thr His Gly Leu
65                  70                  75                  80

Tyr Lys Arg Thr Pro Arg Tyr Pro Glu Glu Leu Glu Leu Leu Val Ser
                85                  90                  95

Gln Gln Ser Pro Cys Gly Arg Ala Thr Ser Ser Ser Arg Ala Trp Trp
            100                 105                 110

Asp Ser Ser Phe Leu Gly Gly Val Val His Leu Glu Ala Gly Glu Glu
        115                 120                 125

Val Val Val Arg Val Leu Asp Glu Arg Leu Val Arg Leu Arg Asp Gly
    130                 135                 140

Thr Arg Ser Tyr Phe Gly Ala Phe Met Val
145                 150

<210> SEQ ID NO 9
<211> LENGTH: 154

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Arg Arg Ser His Glu Val Asn Pro Ala Ala His Leu Thr Gly Ala Asn
1               5                   10                  15

Ser Ser Leu Thr Gly Ser Gly Gly Pro Leu Leu Trp Glu Thr Gln Leu
            20                  25                  30

Gly Leu Ala Phe Leu Arg Gly Leu Ser Tyr His Asp Gly Ala Leu Val
        35                  40                  45

Val Thr Lys Ala Gly Tyr Tyr Tyr Ile Tyr Ser Lys Val Gln Leu Arg
    50                  55                  60

Gly Val Gly Cys Pro Leu Gly Leu Ala Ser Thr Ile Thr His Gly Leu
65                  70                  75                  80

Tyr Lys Arg Thr Pro Arg Tyr Pro Glu Glu Leu Glu Leu Leu Val Asn
                85                  90                  95

Gln Gln Ser Pro Cys Gly Arg Ala Pro Ser Ser Arg Val Trp Trp
            100                 105                 110

Asp Ser Ser Phe Leu Gly Gly Val His Leu Glu Ala Gly Glu Glu
        115                 120                 125

Val Val Val Arg Val Leu Asp Glu Arg Leu Val Arg Leu Arg Asp Gly
    130                 135                 140

Thr Arg Ser Tyr Phe Gly Ala Phe Met Val
145                 150

<210> SEQ ID NO 10
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Arg Arg Ser His Glu Val Asn Pro Ala Ala His Leu Thr Gly Ala Asn
1               5                   10                  15

Ser Ser Leu Thr Gly Ser Gly Gly Pro Leu Leu Trp Glu Thr Gln Leu
            20                  25                  30

Gly Leu Ala Phe Leu Arg Gly Leu Ser Tyr His Asp Gly Ala Leu Val
        35                  40                  45

Val Thr Lys Ala Gly Tyr Tyr Tyr Ile Tyr Ser Lys Val Gln Leu Arg
    50                  55                  60

Gly Val Gly Cys Pro Leu Gly Leu Ala Ser Thr Ile Ala His Gly Leu
65                  70                  75                  80

Tyr Lys Arg Thr Pro Arg Tyr Pro Glu Glu Leu Glu Leu Leu Val Ser
                85                  90                  95

Gln Gln Ser Pro Cys Gly Arg Ala Thr Ser Gly Ser Arg Val Trp Trp
            100                 105                 110

Asp Ser Ser Phe Leu Gly Gly Val His Leu Glu Ala Gly Glu Glu
        115                 120                 125

Val Val Val Arg Val Leu Asp Glu Arg Leu Val Arg Leu Arg Asp Gly
    130                 135                 140

Thr Arg Ser Tyr Phe Gly Ala Phe Met Val
```

```
145                 150

<210> SEQ ID NO 11
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Arg Arg Ser His Glu Val Asn Pro Ala Ala His Leu Thr Gly Ala Asn
1               5                   10                  15

Ser Ser Leu Thr Gly Ser Gly Gly Pro Leu Leu Trp Glu Thr Gln Leu
            20                  25                  30

Gly Leu Ala Phe Leu Arg Gly Leu Ser Tyr His Asp Gly Ala Leu Val
        35                  40                  45

Val Thr Lys Ala Gly Phe Tyr Tyr Ile Tyr Ser Lys Val Gln Leu Gly
    50                  55                  60

Gly Val Gly Cys Pro Leu Gly Arg Ala Ser Thr Ile Thr His Gly Leu
65                  70                  75                  80

Tyr Lys Arg Thr Pro Arg Tyr Pro Glu Glu Leu Glu Leu Leu Val Ser
                85                  90                  95

Gln Gln Ser Pro Cys Gly Arg Ala Thr Ser Ser Ser Arg Val Trp Trp
            100                 105                 110

Asp Ser Ser Phe Leu Gly Gly Val Val His Leu Glu Ala Gly Glu Glu
        115                 120                 125

Val Val Val Arg Val Leu Asp Glu Arg Leu Val Arg Leu Arg Asp Gly
    130                 135                 140

Thr Arg Ser Tyr Phe Gly Ala Phe Met Val
145                 150

<210> SEQ ID NO 12
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Arg Arg Ser His Glu Val Asn Pro Ala Ala His Leu Thr Gly Ala Asn
1               5                   10                  15

Ser Ser Leu Thr Gly Ser Gly Gly Pro Leu Leu Trp Glu Thr Gln Leu
            20                  25                  30

Gly Leu Ala Phe Leu Arg Gly Leu Ser Tyr His Asp Gly Ala Leu Val
        35                  40                  45

Ala Thr Lys Ala Gly Tyr Tyr Tyr Ile Tyr Ser Lys Val Gln Leu Gly
    50                  55                  60

Gly Val Gly Cys Pro Leu Gly Leu Ala Ser Thr Ile Ser His Gly Leu
65                  70                  75                  80

Tyr Lys Arg Thr Pro Arg Tyr Pro Glu Glu Leu Glu Leu Leu Val Ser
                85                  90                  95

Leu Arg Ser Pro Cys Gly Arg Ala Thr Ser Ser Ser Arg Val Trp Trp
            100                 105                 110

Asp Ser Ser Phe Leu Gly Gly Val Val His Leu Glu Ala Gly Glu Glu
        115                 120                 125
```

```
Val Val Val Arg Val Leu Asp Glu Arg Leu Val Arg Leu Arg Asp Gly
        130                 135                 140

Thr Arg Ser Tyr Phe Gly Ala Phe Met Val
145                 150

<210> SEQ ID NO 13
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Arg Arg Ser His Glu Val Asn Pro Ala Ala His Leu Thr Gly Ala Asn
1               5                   10                  15

Ser Ser Leu Thr Gly Ser Gly Gly Pro Leu Leu Trp Glu Thr Gln Leu
            20                  25                  30

Gly Leu Ala Phe Leu Arg Gly Leu Ser Tyr His Asp Gly Ala Leu Val
        35                  40                  45

Val Thr Lys Ala Gly Tyr Tyr Tyr Ile Tyr Ser Lys Val Gln Leu Gly
    50                  55                  60

Gly Val Gly Cys Pro Leu Gly Leu Ala Ser Thr Ile Thr His Gly Leu
65                  70                  75                  80

Tyr Lys Arg Thr Pro Arg Tyr Pro Glu Glu Leu Glu Leu Leu Val Asn
                85                  90                  95

Gln Gln Ser Pro Cys Gly Arg Ala Thr Ser Ser Ser Arg Val Trp Trp
            100                 105                 110

Asp Ser Ser Phe Leu Gly Gly Val Val His Leu Glu Ala Gly Glu Glu
        115                 120                 125

Val Val Val Arg Val Pro Asp Glu Arg Leu Val Arg Leu Arg Asp Gly
    130                 135                 140

Thr Arg Ser Tyr Phe Gly Ala Phe Met Val
145                 150

<210> SEQ ID NO 14
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Arg Arg Ser His Glu Val Asn Pro Ala Ala His Leu Thr Gly Ala Asn
1               5                   10                  15

Ser Ser Leu Thr Gly Ser Gly Gly Pro Leu Leu Trp Glu Thr Gln Leu
            20                  25                  30

Gly Gln Ala Phe Leu Arg Gly Leu Ser Tyr His Asp Gly Ala Leu Val
        35                  40                  45

Val Thr Lys Ala Gly Tyr Tyr Tyr Ile Tyr Ser Lys Val Gln Leu Arg
    50                  55                  60

Gly Val Gly Cys Pro Leu Gly Leu Ala Ser Thr Ile Thr His Gly Leu
65                  70                  75                  80

Tyr Lys Arg Thr Pro Arg Tyr Pro Glu Glu Leu Glu Leu Leu Val Ser
                85                  90                  95
```

```
Gln Gln Ser Pro Cys Gly Arg Ala Thr Ser Ser Ser Arg Val Trp Trp
            100                 105                 110

Asp Ser Ser Phe Leu Gly Gly Val Val His Leu Glu Ala Gly Glu Lys
        115                 120                 125

Val Val Val Arg Val Leu Asp Glu Arg Leu Ala Arg Leu Arg Asp Gly
    130                 135                 140

Thr Arg Ser Tyr Phe Gly Ala Phe Met Val
145                 150

<210> SEQ ID NO 15
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Arg Arg Ser His Glu Val Asn Pro Ala Ala His Leu Thr Gly Ala Asn
1               5                   10                  15

Ser Ser Leu Thr Gly Ser Gly Gly Pro Leu Leu Trp Glu Thr Gln Leu
            20                  25                  30

Gly Gln Ala Phe Leu Arg Gly Leu Ser Tyr His Asp Gly Ala Leu Val
        35                  40                  45

Val Thr Lys Ala Gly Tyr Tyr Tyr Ile Tyr Ser Lys Val Gln Leu Gly
    50                  55                  60

Gly Val Gly Cys Pro Leu Gly Leu Ala Asn Thr Ile Thr His Gly Leu
65                  70                  75                  80

Tyr Lys Arg Thr Pro Arg Tyr Pro Glu Glu Leu Glu Leu Leu Val Ser
                85                  90                  95

Gln Gln Ser Pro Cys Gly Arg Ala Thr Ser Ser Ser Arg Met Trp Trp
            100                 105                 110

Asp Ser Ser Phe Leu Gly Gly Val Val His Leu Glu Ala Gly Glu Lys
        115                 120                 125

Val Val Val Arg Val Leu Asp Glu Arg Leu Val Arg Leu Arg Asp Gly
    130                 135                 140

Thr Arg Ser Tyr Phe Gly Ala Phe Met Val
145                 150

<210> SEQ ID NO 16
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Arg Arg Ser His Glu Val Asn Pro Ala Ala His Leu Thr Gly Ala Asn
1               5                   10                  15

Ser Ser Leu Thr Gly Ser Gly Gly Pro Leu Leu Trp Glu Thr Gln Leu
            20                  25                  30

Gly Leu Ala Phe Leu Arg Gly Leu Ser Tyr His Asp Gly Ala Leu Val
        35                  40                  45

Val Thr Lys Ala Gly Tyr Tyr Tyr Ile Tyr Ser Lys Val Gln Leu Arg
    50                  55                  60

Gly Val Gly Cys Pro Leu Gly Leu Ala Ser Pro Ile Thr His Gly Leu
```

```
                65                  70                  75                  80
Tyr Lys Arg Thr Pro Arg Tyr Pro Glu Glu Leu Glu Leu Leu Val Ser
                    85                  90                  95

Gln Gln Ser Pro Cys Gly Arg Ala Thr Ser Ser Ser Arg Val Trp Trp
                100                 105                 110

Asp Ser Ser Phe Leu Gly Gly Val Val His Leu Glu Ala Gly Glu Lys
                115                 120                 125

Val Val Val Arg Val Leu Asp Glu Arg Leu Val Arg Gln Gly Asp Gly
        130                 135                 140

Thr Arg Ser Tyr Phe Gly Ala Phe Met Val
145                 150

<210> SEQ ID NO 17
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Arg Arg Ser His Glu Val Asn Pro Ala Ala His Leu Thr Gly Ala Asn
1               5                   10                  15

Ser Ser Leu Thr Gly Ser Gly Gly Pro Leu Leu Trp Glu Thr Gln Leu
                20                  25                  30

Gly Leu Ala Phe Leu Arg Gly Leu Ser Tyr His Asp Gly Ala Leu Val
            35                  40                  45

Val Thr Lys Ala Gly Tyr Tyr Tyr Ile Tyr Ser Lys Val Gln Leu Gly
        50                  55                  60

Gly Val Gly Cys Pro Leu Gly Leu Ala Ser Thr Phe Thr His Gly Leu
65                  70                  75                  80

Tyr Lys Arg Thr Pro Arg Tyr Pro Glu Glu Leu Glu Leu Leu Val Ser
                    85                  90                  95

Gln Gln Ser Pro Cys Gly Arg Ala Ser Ser Ser Ser Arg Val Trp Trp
                100                 105                 110

Asp Ser Ser Phe Leu Gly Gly Val Val His Leu Glu Ala Gly Glu Lys
                115                 120                 125

Val Val Val Arg Val Leu Asp Glu Arg Leu Val Arg Leu Arg Asp Gly
        130                 135                 140

Thr Arg Ser Tyr Phe Gly Ala Phe Met Val
145                 150

<210> SEQ ID NO 18
<211> LENGTH: 153
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Arg Ser His Glu Val Asn Pro Ala Ala His Leu Thr Gly Ala Asn Ser
1               5                   10                  15

Ser Leu Thr Gly Ser Gly Gly Pro Leu Leu Trp Glu Thr Gln Leu Gly
                20                  25                  30

Leu Ala Phe Leu Arg Gly Leu Ser Tyr His Asp Gly Ala Leu Val Val
            35                  40                  45
```

```
Thr Lys Thr Gly Tyr Tyr Tyr Ile Tyr Ser Lys Val Gln Leu Gly Gly
        50                  55                  60

Val Gly Cys Pro Leu Gly Leu Ala Gly Thr Ile Thr His Gly Leu Tyr
 65                  70                  75                  80

Lys Arg Thr Pro Arg Tyr Pro Glu Glu Leu Glu Leu Leu Val Ser Gln
                 85                  90                  95

Gln Ser Pro Cys Gly Arg Ala Thr Ser Ser Arg Val Trp Trp Asp
                100                 105                 110

Ser Ser Phe Leu Gly Gly Val Val His Leu Glu Ala Gly Glu Lys Val
            115                 120                 125

Val Val Arg Val Leu Gly Lys Arg Leu Val Arg Leu Arg Asp Gly Thr
        130                 135                 140

Arg Ser Tyr Phe Gly Ala Phe Met Val
145                 150

<210> SEQ ID NO 19
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Arg Arg Ser His Glu Val Asn Pro Ala Ala His Leu Thr Gly Ala Asn
 1               5                  10                  15

Ser Asn Leu Thr Gly Ser Gly Gly Pro Leu Leu Trp Glu Thr Gln Leu
            20                  25                  30

Gly Leu Ala Phe Leu Arg Gly Leu Ser Tyr His Asp Gly Ala Leu Val
        35                  40                  45

Val Thr Lys Ala Gly Tyr Tyr Tyr Ile Tyr Ser Lys Val Gln Leu Gly
    50                  55                  60

Gly Val Gly Cys Pro Leu Gly Leu Ala Ser Thr Ile Thr His Gly Leu
 65                 70                  75                  80

Tyr Lys Arg Thr Pro Arg Tyr Pro Glu Glu Leu Glu Leu Leu Val Ser
                85                  90                  95

Gln Gln Ser Pro Cys Gly Arg Ala Thr Ser Ser Arg Val Trp Trp
                100                 105                 110

Asp Ser Ser Phe Leu Gly Gly Val Val His Leu Glu Ala Gly Glu Lys
            115                 120                 125

Val Val Val Arg Val Gln Asp Glu Arg Leu Val Arg Leu Arg Asp Gly
        130                 135                 140

Thr Arg Ser Tyr Phe Gly Ala Phe Met Val
145                 150

<210> SEQ ID NO 20
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Arg Arg Ser His Glu Val Asn Pro Ala Ala His Leu Thr Gly Ala Asn
 1               5                  10                  15
```

```
Ser Ser Leu Thr Gly Ser Gly Gly Pro Leu Leu Trp Glu Thr Gln Leu
            20                  25                  30

Gly Leu Ala Phe Leu Arg Gly Leu Ser Tyr His Asp Gly Ala Leu Val
            35                  40                  45

Val Thr Lys Thr Gly Tyr Tyr Tyr Ile Tyr Ser Lys Val Gln Leu Gly
 50                  55                  60

Gly Val Gly Cys Pro Leu Gly Leu Ala Gly Thr Ile Thr His Gly Leu
65                  70                  75                  80

Tyr Lys Arg Thr Pro Arg Tyr Pro Glu Glu Leu Glu Leu Leu Val Ser
                85                  90                  95

Gln Gln Ser Pro Cys Gly Arg Ala Thr Ser Ser Ser Arg Val Trp Trp
                100                 105                 110

Asp Ser Ser Phe Leu Gly Gly Val Val His Leu Glu Ala Gly Glu Lys
            115                 120                 125

Val Val Val Arg Val Leu Gly Lys Arg Leu Val Arg Leu Arg Asp Gly
130                 135                 140

Thr Arg Ser Tyr Phe Gly Ala Phe Met Val
145                 150

<210> SEQ ID NO 21
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Arg Arg Ser His Glu Val Asn Pro Ala Ala His Leu Thr Gly Ala Asn
1               5                   10                  15

Ser Ser Leu Thr Gly Ser Gly Gly Pro Leu Leu Trp Glu Pro Gln Leu
            20                  25                  30

Gly Leu Ala Phe Leu Arg Gly Leu Ser Tyr His Asp Gly Ala Leu Val
            35                  40                  45

Val Thr Lys Ala Gly Tyr Tyr Tyr Ile Tyr Ser Lys Val Gln Leu Arg
 50                  55                  60

Gly Val Gly Cys Pro Leu Gly Leu Thr Arg Thr Ile Thr His Gly Leu
65                  70                  75                  80

Tyr Lys Arg Thr Pro Arg Tyr Pro Glu Glu Leu Glu Leu Leu Val Ser
                85                  90                  95

Gln Gln Ser Pro Cys Gly Arg Ala Thr Pro Ser Ser Arg Val Trp Trp
                100                 105                 110

Asp Ser Ser Phe Leu Gly Gly Val Val His Leu Glu Ala Gly Glu Lys
            115                 120                 125

Val Val Val Arg Val Leu Asp Glu Arg Leu Val Arg Leu Met Asp Gly
130                 135                 140

Thr Arg Ser Tyr Phe Gly Ala Phe Met Val
145                 150

<210> SEQ ID NO 22
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 22

Arg Gly Ser His Glu Val Asn Pro Ala Ala His Leu Thr Gly Ala Ser
1               5                   10                  15

Ser Ser Leu Thr Gly Ser Gly Gly Pro Leu Leu Trp Glu Thr Gln Leu
            20                  25                  30

Gly Leu Ala Phe Leu Arg Gly Leu Ser Tyr His Asp Gly Ala Leu Val
        35                  40                  45

Val Thr Lys Ala Gly Tyr Tyr Tyr Ile Tyr Ser Lys Val Gln Leu Arg
    50                  55                  60

Gly Val Gly Cys Pro Leu Gly Leu Ala Ser Thr Ile Thr His Gly Leu
65                  70                  75                  80

Tyr Lys Arg Thr Pro Arg Tyr Pro Glu Glu Leu Glu Leu Leu Val Ser
                85                  90                  95

Gln Gln Ser Pro Cys Gly Arg Ala Thr Ser Ser Ser Arg Val Trp Trp
            100                 105                 110

Asp Ser Ser Phe Leu Gly Gly Val Val His Leu Glu Ala Gly Glu Glu
        115                 120                 125

Val Val Val Arg Val Leu Asp Glu Arg Leu Val Arg Leu Arg Asp Gly
    130                 135                 140

Thr Arg Ser Tyr Phe Gly Ala Phe Met Val
145                 150

<210> SEQ ID NO 23
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Arg Arg Ser His Glu Val Asn Pro Ala Ala His Leu Thr Gly Ala Asn
1               5                   10                  15

Ser Ser Leu Thr Gly Ser Gly Gly Pro Leu Leu Trp Glu Thr Gln Leu
            20                  25                  30

Gly Leu Ala Phe Leu Arg Gly Leu Ser Tyr His Asp Gly Ala Leu Val
        35                  40                  45

Val Thr Lys Ala Gly Tyr Tyr Tyr Ile Tyr Ser Lys Val Gln Leu Gly
    50                  55                  60

Gly Val Gly Cys Pro Leu Gly Arg Ala Ser Thr Ile Thr His Gly Leu
65                  70                  75                  80

Tyr Lys Arg Thr Pro Arg Tyr Pro Glu Glu Leu Glu Leu Leu Val Ser
                85                  90                  95

Gln Gln Ser Pro Cys Gly Arg Ala Thr Ser Ser Ser Arg Val Trp Trp
            100                 105                 110

Asp Ser Ser Phe Leu Gly Gly Val Val His Leu Glu Ala Gly Glu Lys
        115                 120                 125

Val Val Val Arg Val Gln Asp Glu Arg Leu Val Arg Leu Arg Asp Gly
    130                 135                 140

Thr Arg Ser Tyr Phe Gly Ala Phe Met Val
145                 150

<210> SEQ ID NO 24
<211> LENGTH: 153
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 24

Arg Ser His Glu Val Asn Pro Ala Ala His Leu Thr Gly Ala Asn Ser
1               5                   10                  15

Ser Leu Thr Gly Ser Gly Gly Pro Leu Leu Trp Glu Thr Gln Leu Gly
            20                  25                  30

Leu Ser Phe Leu Arg Gly Leu Ser Tyr His Asp Gly Ala Leu Val Val
        35                  40                  45

Thr Lys Ala Gly Tyr Tyr Tyr Ile Tyr Ser Lys Val Gln Leu Arg Gly
50                  55                  60

Val Gly Cys Pro Leu Gly Leu Ala Ser Thr Ile Thr His Gly Leu Tyr
65                  70                  75                  80

Lys Arg Thr Pro Arg Tyr Pro Glu Glu Leu Glu Leu Val Ser Gln
                85                  90                  95

Gln Ser Pro Cys Gly Arg Ala Thr Ser Ser Arg Val Trp Trp Asp
            100                 105                 110

Ser Ser Leu Gly Gly Val Val His Leu Glu Ala Gly Glu Lys Val
            115                 120                 125

Val Val Arg Val Leu Asp Glu Arg Leu Val Arg Leu Met Asp Gly Thr
130                 135                 140

Arg Ser Tyr Phe Gly Ala Phe Met Val
145                 150

<210> SEQ ID NO 25
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gln Arg Ser His Glu Val Asn Pro Ala Ala His Leu Thr Gly Ala Asn
1               5                   10                  15

Ser Ser Pro Thr Gly Ser Gly Gly Pro Leu Leu Trp Glu Thr Gln Leu
            20                  25                  30

Gly Leu Ala Phe Leu Arg Gly Leu Ser Tyr His Asp Gly Ala Leu Val
        35                  40                  45

Val Thr Lys Ala Gly Tyr Tyr Tyr Ile Tyr Ser Lys Val Gln Leu Gly
    50                  55                  60

Gly Val Gly Cys Pro Leu Gly Leu Ala Ser Thr Ile Thr His Gly Leu
65                  70                  75                  80

Tyr Lys Arg Thr Pro Arg Tyr Pro Glu Glu Leu Glu Leu Leu Val Ser
                85                  90                  95

Leu Gln Ser Pro Cys Gly Arg Ala Thr Ser Ser Arg Val Trp Trp
            100                 105                 110

Asp Ser Ser Phe Leu Gly Gly Val Val His Leu Glu Ala Gly Glu Lys
            115                 120                 125

Val Val Val Arg Val Leu Asp Glu Arg Leu Val Arg Pro Arg Asp Gly
    130                 135                 140

Thr Arg Ser Tyr Phe Gly Ala Phe Met Val
145                 150
```

<210> SEQ ID NO 26
<211> LENGTH: 181
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 26

Gln Leu His Trp Arg Leu Gly Glu Met Val Thr Arg Leu Pro Asp Gly
1               5                   10                  15
Pro Ala Gly Ser Trp Glu Gln Leu Ile Gln Glu Arg Arg Ser His Glu
            20                  25                  30
Val Asn Pro Ala Ala His Leu Thr Gly Ala Asn Ser Ser Leu Thr Gly
        35                  40                  45
Ser Gly Gly Pro Leu Leu Trp Glu Thr Gln Leu Gly Leu Ala Phe Leu
    50                  55                  60
Arg Gly Leu Ser Tyr His Asp Gly Ala Leu Val Val Thr Lys Ala Gly
65                  70                  75                  80
Tyr Tyr Tyr Ile Tyr Ser Lys Val Gln Leu Gly Gly Val Gly Cys Pro
                85                  90                  95
Leu Gly Leu Ala Ser Thr Ile Thr His Gly Leu Tyr Lys Arg Thr Pro
            100                 105                 110
Arg Tyr Pro Glu Glu Leu Glu Leu Leu Val Ser Gln Gln Ser Pro Cys
        115                 120                 125
Gly Arg Ala Thr Ser Ser Ser Arg Val Trp Trp Asp Ser Ser Phe Leu
    130                 135                 140
Gly Gly Val Val His Leu Glu Ala Gly Glu Lys Val Val Val Arg Val
145                 150                 155                 160
Leu Asp Glu Arg Leu Val Arg Leu Arg Asp Gly Thr Arg Ser Tyr Phe
                165                 170                 175
Gly Ala Phe Met Val
            180

<210> SEQ ID NO 27
<211> LENGTH: 723
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 27
atggaggaga gtgtcgtacg gccctcagtg tttgtggtgg atggacagac cgacatccca    60
ttcacgaggc tgggacgaag ccaccggaga cagtcgtgca gtgtggcccg ggtgggtctg   120
ggtctcttgc tgttgctgat ggggctgggc tggccgtcc aaggctggtt cctcctgcag    180
ctgcactggc gtctaggaga gatggtcacc cgcctgcctg acggacctgc aggctcctgg   240
gagcagctga tacaagagcg aaggtctcac gaggtcaacc cagcagcgca tctcacaggg   300
gccaactcca gcttgaccgg cagcgggggg ccgctgttat gggagactca gctgggcctg   360
gccttcctga ggggcctcag ctaccacgat ggggcccttg tggtcaccaa agctggctac   420
tactacatct actccaaggt gcagctgggc ggtgtgggct gccgctgggc cctggccagc   480
accatcaccc acggcctcta caagcgcaca ccccgctacc ccgaggagct ggagctgttg   540
gtcagccagc agtcaccctg cggacgggcc accagcagct cccgggtctg gtgggacagc   600

```
agcttcctgg gtggtgtggt acacctggag gctggggaga aggtggtcgt ccgtgtgctg      660
gatgaacgcc tggttcgact gcgtgatggt acccggtctt acttcggggc tttcatggtg      720
tga                                                                    723
```

<210> SEQ ID NO 28
<211> LENGTH: 12
<212> TYPE: DNA
<213> ORGANISM: Homo sapiens

<400> SEQUENCE: 28

```
gagcagctga ta                                                           12
```

<210> SEQ ID NO 29
<211> LENGTH: 723
<212> TYPE: DNA
<213> ORGANISM: Homo sapiens

<400> SEQUENCE: 29

```
atggaggaga gtgtcgtacg gccctcagtg tttgtggtgg atggacagac cgacatccca       60
ttcacgaggc tgggacgaag ccaccggaga cagtcgtgca gtgtggcccg ggtgggtctg      120
ggtctcttgc tgttgctgat gggggctggg ctggccgtcc aaggctggtt cctcctgcag      180
ctgcactggc gtctaggaga gatggtcacc cgcctgcctg acggacctgc aggtcctgg       240 gagcagctga tacaagagcg aaggtctcac gaggtcaacc cagcagcgca tctcacaggg      300
gccaactcca gcttgaccgg cagcgggggg ccgctgttat gggagactca gctgggcctg      360
gccttcctga ggggcctcag ctaccacgat ggggcccttg tggtcaccaa agctggctac      420
tactacatct actccaaggt gcagctgggc ggtgtgggct gccgctgggg cctggccagc      480
accatcaccc acggcctcta caagcgcaca ccccgctacc ccgaggagct ggagctgttg      540
gtcagccagc agtcaccctg cggacgggcc accagcagct cccgggtctg gtgggacagc      600
agcttcctgg gtggtgtggt acacctggag gctggggaga aggtggtcgt ccgtgtgctg      660
gatgaacgcc tggttcgact gcgtgatggt acccggtctt acttcggggc tttcatggtg      720
tga                                                                    723
```

<210> SEQ ID NO 30
<211> LENGTH: 240
<212> TYPE: PRT
<213> ORGANISM: Homo sapiens

<400> SEQUENCE: 30

```
Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110
```

Leu Trp Glu Thr Gln Leu Gly Leu Ala Phe Leu Arg Gly Leu Ser Tyr
            115                 120                 125

His Asp Gly Ala Leu Val Val Thr Lys Ala Gly Tyr Tyr Ile Tyr
    130                 135                 140

Ser Lys Val Gln Leu Gly Gly Val Gly Cys Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
                180                 185                 190

Ser Ser Arg Val Trp Trp Asp Ser Ser Phe Leu Gly Val Val His
            195                 200                 205

Leu Glu Ala Gly Glu Lys Val Val Arg Val Leu Asp Glu Arg Leu
            210                 215                 220

Val Arg Leu Arg Asp Gly Thr Arg Ser Tyr Phe Gly Ala Phe Met Val
225                 230                 235                 240

<210> SEQ ID NO 31
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
                20                  25                  30

Cys Ser Val Ala Arg Val Gly Leu Gly Leu Leu Leu Leu Met Gly
            35                  40                  45

Ala Gly Leu Ala Val Gln Gly Trp Phe Leu Leu Gln Leu His Trp Arg
 50                 55                  60

Leu Gly Glu Met Val Thr Arg Leu Pro Asp Gly Pro Ala Gly Ser Trp
65                  70                  75                  80

Gln Glu Arg Arg Ser His Glu Val Asn Pro Ala Ala His Leu Thr Gly
                85                  90                  95

Ala Asn Ser Ser Leu Thr Gly Ser Gly Gly Pro Leu Leu Trp Glu Thr
            100                 105                 110

Gln Leu Gly Leu Ala Phe Leu Arg Gly Leu Ser Tyr His Asp Gly Ala
            115                 120                 125

Leu Val Val Thr Lys Ala Gly Tyr Tyr Ile Tyr Ser Lys Val Gln
    130                 135                 140

Leu Gly Gly Val Gly Cys Pro Leu Gly Leu Ala Ser Thr Ile Thr His
145                 150                 155                 160

Gly Leu Tyr Lys Arg Thr Pro Arg Tyr Pro Glu Glu Leu Glu Leu Leu
                165                 170                 175

Val Ser Gln Gln Ser Pro Cys Gly Arg Ala Thr Ser Ser Arg Val
            180                 185                 190

Trp Trp Asp Ser Ser Phe Leu Gly Val Val His Leu Glu Ala Gly
        195                 200                 205

Glu Lys Val Val Val Arg Val Leu Asp Glu Arg Leu Val Arg Leu Arg
            210                 215                 220

Asp Gly Thr Arg Ser Tyr Phe Gly Ala Phe Met Val
225                 230                 235

<210> SEQ ID NO 32
<211> LENGTH: 814
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32

| | | | | | |
|---|---|---|---|---|---|
| gggcgaattg | ggtaccggat | ccgccaccat | ggagagcgtg | gtgcagccca | gcgtgttcgt | 60 |
| ggtggacggc | cagaccgaca | tccccttcag | gaggctggag | cagaaccaca | ggcggaggag | 120 |
| atgtggcacc | gtgcaggtgt | ccctggccct | ggtgctgctg | ctgggcgctg | gcctggccac | 180 |
| ccagggctgg | tttctgctga | ggctgcacca | gaggctgggc | gacatcgtgg | cccacctgcc | 240 |
| cgatggcggc | aagggcagct | ggcaggacca | gaggagccac | caggccaacc | ctgccgccca | 300 |
| cctgacaggc | gccaacgcca | gcctgatcgg | catcggcgga | ccctgctgt | gggagaccag | 360 |
| gctgggcctg | gctttcctga | ggggcctgac | ctaccacgac | ggcgccctgg | tgaccatgga | 420 |
| gcccggctac | tactacgtgt | acagcaaggt | gcagctgtcc | ggagtgggct | gccctcaggg | 480 |
| cctggccaac | ggcctgccca | tcacccacgc | cctgtacaag | aggaccagca | gataccccaa | 540 |
| ggagctggag | ctgctggtct | ccaggcggag | cccctgtggc | agggccaaca | gcagccgagt | 600 |
| gtggtgggac | agcagcttcc | tgggcggcgt | ggtgcacctg | gaggcggcg | aggaggtggt | 660 |
| ggtgagggtg | cccggcaaca | ggctggtgag | gcccagggac | ggcaccagga | gctacttcgg | 720 |
| cgccttcatg | gtgtgatgag | cggccgcgag | ctccagcttt | gttcccgcg | aagtaccac | 780 |
| actactcgcc | ggcgctcgag | gtcgaaaaca | aggg | | | 814 |

<210> SEQ ID NO 33
<211> LENGTH: 814
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33

| | | | | | |
|---|---|---|---|---|---|
| gaattcgagc | tcggtacccg | acacggtacc | ggatccgcca | ccatggagga | gagcgttgtg | 60 |
| aggcccagcg | tgttcgtggt | ggacggccag | accgacatcc | ccttcacccg | gctgggccgg | 120 |
| agccaccgga | ggcagagctg | ctccgtggcc | agagtggggc | tgggcctgct | gctcctgctg | 180 |
| atgggagccg | gctggccgt | gcaggctgg | ttcctgctgc | agctgcactg | gcggctgggc | 240 |
| gagatggtga | cccggctgcc | cgatggccct | gccggcagct | ggcaggagcg | gcggagccac | 300 |
| gaggtgaacc | ctgccgccca | cctgaccggc | gccaacagca | gcctgaccgg | cagcggcgga | 360 |
| cccctgctgt | gggagaccca | gctgggcctg | gccttcctga | ggggcctgag | ctaccacgac | 420 |
| ggcgccctgg | tggtgaccaa | ggccggctac | tactacatct | acagcaaggt | gcagctgggc | 480 |
| ggagtgggct | gccctctggg | gctggccagc | accatcaccc | acggcctgta | caagcggacc | 540 |
| cccagatacc | ccgaggagct | ggagctgctg | gtgtcccagc | agagcccctg | tggcagggcc | 600 |
| acctccagca | gccgggtgtg | gtgggacagc | agcttcctgg | gcggcgtggt | gcacctggag | 660 |
| gccggcgaga | agtggttgt | gagggtgctg | gacgagcggc | ttgtgaggct | gagggacggc | 720 |

```
acccggagct acttcggcgc cttcatggtg tgatgagcgg ccgcgagctc gtctcgggga        780
tcctctagag tcgacctgca ggcatgcaag cttg                                   814
```

<210> SEQ ID NO 34
<211> LENGTH: 9
<212> TYPE: PRT
<213> ORGANISM: Murine cytomegalovirus

<400> SEQUENCE: 34

Tyr Pro His Phe Met Pro Thr Asn Leu
1               5

<210> SEQ ID NO 35
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Gln Leu Ser Pro Phe Pro Phe Asp Leu
1               5

<210> SEQ ID NO 36
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36

```
catggatcca agaccatgga gagtgtggta ca                                     32
```

<210> SEQ ID NO 37
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37

```
agatcgttga tcttgccagg agcctttgcc                                        30
```

<210> SEQ ID NO 38
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38

```
ggcaaaggct cctggcaaga tcaacgatct                                        30
```

<210> SEQ ID NO 39
<211> LENGTH: 29
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 39
acctctagat cagaccatga aagctccga                                            29

<210> SEQ ID NO 40
<211> LENGTH: 181
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40
```

Gln Leu His Trp Arg Leu Gly Glu Met Val Thr Arg Leu Pro Asp Gly
1               5                   10                  15

Pro Ala Gly Ser Trp Glu Gln Leu Ile Gln Glu Arg Arg Ser His Glu
            20                  25                  30

Val Asn Pro Ala Ala His Leu Thr Gly Ala Asn Ser Ser Leu Thr Gly
        35                  40                  45

Ser Gly Gly Pro Leu Leu Trp Glu Thr Gln Leu Gly Leu Ala Phe Leu
    50                  55                  60

Arg Gly Leu Ser Tyr His Asp Gly Ala Leu Val Val Thr Lys Ala Gly
65                  70                  75                  80

Tyr Tyr Tyr Thr Tyr Ser Lys Val Gln Leu Gly Gly Val Gly Cys Pro
                85                  90                  95

Leu Gly Leu Ala Ser Thr Ile Thr His Gly Leu Tyr Lys Arg Thr Pro
            100                 105                 110

Arg Tyr Pro Glu Glu Leu Glu Leu Leu Val Ser Gln Gln Ser Pro Cys
        115                 120                 125

Gly Arg Ala Thr Ser Ser Ser Arg Val Trp Trp Asp Ser Ser Phe Leu
    130                 135                 140

Gly Gly Val Val His Leu Glu Ala Gly Glu Lys Val Val Val Arg Val
145                 150                 155                 160

Leu Asp Glu Arg Leu Val Arg Leu Arg Asp Gly Thr Arg Ser Tyr Phe
                165                 170                 175

Gly Ala Phe Met Val
            180

```
<210> SEQ ID NO 41
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41
```

Arg Thr Val Ala Ala
1               5

```
<210> SEQ ID NO 42
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 42

Gly Gly Gly Gly Ser Gly Gly Gly Ser Gly Gly Gly Gly Ser
1               5                   10                  15

<210> SEQ ID NO 43
<211> LENGTH: 154
<212> TYPE: PRT
<213> ORGANISM: Homo sapiens

<400> SEQUENCE: 43

Arg Arg Ser His Glu Val Asn Pro Ala Ala His Leu Thr Gly Ala Asn
1               5                   10                  15

Ser Ser Leu Thr Gly Ser Gly Gly Pro Leu Leu Trp Glu Thr Gln Leu
            20                  25                  30

Gly Leu Ala Phe Leu Arg Gly Leu Ser Tyr His Asp Gly Ala Leu Val
        35                  40                  45

Val Thr Lys Ala Gly Tyr Tyr Tyr Ile Tyr Ser Lys Val Gln Leu Gly
    50                  55                  60

Gly Val Gly Cys Pro Leu Gly Leu Ala Ser Thr Ile Thr His Gly Leu
65                  70                  75                  80

Tyr Lys Arg Thr Pro Arg Tyr Pro Glu Glu Leu Glu Leu Leu Val Ser
                85                  90                  95

Gln Gln Ser Pro Cys Gly Arg Ala Thr Ser Ser Ser Arg Val Trp Trp
            100                 105                 110

Asp Ser Ser Phe Leu Gly Gly Val Val His Leu Glu Ala Gly Glu Lys
        115                 120                 125

Val Val Val Arg Val Leu Asp Glu Arg Leu Val Arg Leu Arg Asp Gly
    130                 135                 140

Thr Arg Ser Tyr Phe Gly Ala Phe Met Val
145                 150

<210> SEQ ID NO 44
<211> LENGTH: 43
<212> TYPE: PRT
<213> ORGANISM: Mus sp.

<400> SEQUENCE: 44

Gln Arg His Thr Asn Ala Ser Leu Pro Leu Thr Leu Ala Arg Thr Tyr
1               5                   10                  15

Val Ser Gly Leu Ala Leu Pro Ile Thr Lys Leu Ser Arg Arg Pro Asn
            20                  25                  30

Ser Ser Val Phe Glu Pro Gly Asn Val Pro Arg
        35                  40

<210> SEQ ID NO 45
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Arg Arg Ser His Glu Val Asn Pro Ala Ala His Leu Thr Gly Ala Asn
1               5                   10                  15

Ser Ser Leu Thr Gly Ser Gly Gly Pro Leu Leu Trp Glu Thr Gln Leu
            20                  25                  30

Gly Leu Ser Phe Leu Arg Gly Leu Ser Tyr His Asp Gly Ala Leu Val
            35                  40                  45

Val Thr Lys Ala Gly Tyr Tyr Tyr Ile Tyr Ser Lys Val Gln Leu Arg
 50                  55                  60

Gly Val Gly Cys Pro Leu Gly Leu Ala Ser Thr Ile Thr His Gly Leu
 65                  70                  75                  80

Tyr Lys Arg Thr Pro Arg Tyr Pro Glu Glu Leu Glu Leu Leu Val Ser
                85                  90                  95

Gln Gln Ser Pro Cys Gly Arg Ala Thr Ser Ser Ser Arg Val Trp Trp
            100                 105                 110

Asp Ser Ser Leu Gly Gly Val Val His Leu Glu Ala Gly Glu Lys
            115                 120                 125

Val Val Val Arg Val Leu Asp Glu Arg Leu Val Arg Leu Met Asp Gly
130                 135                 140

Thr Arg Ser Tyr Phe Gly Ala Phe Met Val
145                 150

<210> SEQ ID NO 46
<211> LENGTH: 465
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 46
cgaaggtctc acgaggtcaa cccagcagcg catctcacag gggccaactc cagcttgacc        60
ggcagcgggg ggccgctgtt atgggagact cagctgggcc tggccttcct gagggggcctc      120 agctaccacg atggggccct tgtggtcacc aaagctggct actactacat ctactccaag      180
gtgcagctgg gcggtgtggg ctgcccgctg gcctggcca gcaccatcac ccacggcctc       240
tacaagcgca caccccgcta ccccgaggag ctggagctgt tggtcagcca gcagtcaccc      300
tgcggacggg ccaccagcag ctcccgggtc tggtgggaca gcagcttcct gggtggtgtg      360
gtacacctgg aggctgggga aaggtggtc gtccgtgtgc tggatgaacg cctggttcga       420
ctgcgtgatg gtaccggtc ttacttcggg gctttcatgg tgtga                       465

<210> SEQ ID NO 47
<211> LENGTH: 465
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 47
cgaaggtctc acgaggtcaa cccagcagcg catctcacag gggccaactc cagcttgacc        60
ggcagcgggg ggccgctgtt atgggagact cagctgggcc tggccttcct gagcggcctc      120
agctaccacg atggggccct tgtggtcacc aaagctggct actactacat ctactccaag      180
gtgcagctgc gcggtgtggg ctgcccgctg gcctggcca gcaccatcac ccacggcctc       240
tacaagcgca caccccgcta ccccgaggag ctggagctgt tggtcagcca gcagtcaccc      300
tgcggacggg ccaccagcag ctcccgggtc tggtgggaca gcagcttcct gggtggtgtg      360

```
gtacacctgg aggctgggga ggaggtggtc gtccgtgtgt tgggtgaacg actggttcga     420
ctgcgtgatg gtacccggtc ttacttcggg gctttcatgg tgtga                    465
```

COMPOSITIONS FOR CANCER THERAPY USING MUTANT LIGHT MOLECULES WITH INCREASED AFFINITY TO RECEPTORS

CROSS REFERENCE TO RELATED APPLICATIONS

This application is a U.S. nationalization under 35 U.S.C. §371 of International Application No. PCT/US2012/069013, filed Dec. 11, 2012, which claims the benefit of priority under 35 U.S.C. §119(e) to U.S. Provisional Patent Application No. 61/576,222, filed Dec. 15, 2011. The disclosures set forth in the referenced applications are incorporated herein by reference in their entireties, including all information as originally submitted to the United States Patent and Trademark Office.

SEQUENCE LISTING

The instant application contains a Sequence Listing which has been submitted in ASCII format via EFS-Web and is hereby incorporated by reference in its entirety. Said ASCII copy, created on Dec. 5, 2012, is named 700286_SEQ_ST25.txt and is 54,899 bytes in size.

BACKGROUND

Methods and compositions are disclosed to target tumor cells with embodiments of the LIGHT proteins linked, fused or conjugated to a targeting agent. These compositions bind to both human and mouse receptors with affinity sufficient to conduct preclinical and clinical trials, and with increased affinity as compared to the wild type human LIGHT protein. The targeting of embodiments of LIGHT to tumor cells reduces tumor growth and reduces metastases.

The paucity of activated T cells infiltrating established tumors in immunocompetent hosts helps to explain the inability of hosts to dispose of tumors. Experiments in animal models as well as clinical studies indicate that the immune system can recognize and kill individual tumor cells, but a host cannot generally eradicate established solid tumors. There may be several explanations for the failure of the host to respond effectively to established tumors: 1) lack of early T cell priming due to poor direct or indirect presentation in lymphoid tissues because of an inadequate number of tumor cells (especially those of non-hemopoietic origin) migrating to the lymphoid tissue; 2) inadequate numbers of immune cells migrating to tumor sites due to biological barriers around tumor tissues; 3) exhausted or short-lived activated antigen-specific T cells that fail to combat tumor growth due to limited repertoires; 4) unresponsiveness or ignorance of T cells to tumors; 5) an inhibitory microenvironment or lack of stimulation inside tumors to activate the immune system.

Clinically, an increase in the infiltration of T cells to the tumor site is closely associated with better prognosis. There are reports that preventive vaccinations were effective in inducing the rejection of inoculated tumor cells. After tumor growth has been established, however, the therapeutic vaccinations usually fail to reject tumors. Surgical reduction of a tumor does not boost the immune response to tumors. Furthermore, it was reported that even the expression of a strong antigen on tumor cells was insufficient in promoting the rejection of an established tumor, despite the presence of excessive numbers of antigen-specific T cells in the lymphoid tissues. Lack of T cells priming and/or infiltrating an established tumor is one of the major obstacles for either natural or therapeutic approaches against antigenic cancers. In addition, insufficient expression of costimulatory molecules inside tumor tissues may fail to activate infiltrating T cells and result in the anergy of tumor-reactive T cells.

The lack of early T cell priming is possibly attributed to only a few tumor cells that migrated from solid tissue to lymphoid tissues for direct presentation. Genetic analysis using bone marrow chimeras has revealed two modes of antigen presentation for priming MHC-1-restricted CD8$^+$ T cells. Direct-priming is mediated by the engagement of T cells with the cells that synthesize the protein with antigenic epitopes, whereas cross-priming is mediated by the host antigen-presenting cells that take up antigens synthesized by other cells. The mechanisms by which tumor-specific T cells are primed has been vigorously debated and so far remains inconclusive. Understanding how and where tumor antigens are presented to T cells would help find a therapeutic action against tumors.

LIGHT (homologous to lymphotoxin, exhibits inducible expression, and competes with HSV glycoprotein D for herpes virus entry mediator, a receptor expressed by T lymphocytes) is a type II transmembrane glycoprotein of the TNF ligand superfamily. LIGHT (TNFSF14) is a tumor-necrosis factor (TNF) family member that interacts with Lymphotoxin β Receptor (LTβR) and herpes virus entry mediator (HVEM), which are mainly expressed on stromal cells and T cells, respectively. LTβR signaling is required for the formation of organized lymphoid structures, which can be attributed, at least in part, to its ability to induce the expression of chemokines and adhesion molecules that attract naive T cells and dendritic cells (DC) in lymphoid organs. Stimulation of LTβR on stromal cells by LIGHT in vivo leads to the expression of CCL21, which attracts naive T cells in the T cell area of the spleen in the absence of LTαβ, another ligand for LTβR. These results demonstrate that LIGHT is able to interact with LTβR to regulate CCL21 chemokine expression. In addition, LIGHT exhibits a potent, CD28-independent co-stimulatory activity for T cell priming and expansion leading to enhanced T cell immunity against tumors and/or increased autoimmunity. Signaling via LTβR is required for the formation of organized lymphoid tissues. Lymphotoxin β Receptor (LTβR) plays an important role in the formation of lymphoid structures. LTβR is activated by two members of the TNF family, membrane lymphotoxinα β and LIGHT. LTβR plays pivotal roles in the formation of lymph nodes (LNs) and the distinct organization of T, B zones in secondary lymphoid organs. Signaling via LTβR regulates the expression of chemokines and adhesion molecules within secondary lymphoid organs. Chemokines and adhesion molecules control the migration and positioning of DCs and lymphocytes in the spleen. Overexpression of soluble LT or TNF in non-lymphoid tissues was sufficient to promote functional lymphoid neogenesis.

LIGHT has also been called HVEM-L and LT-γ. Under the new TNF nomenclature, it is called TNFSF14. LIGHT is a 240 amino acid (aa) protein that contains a 37 aa cytoplasmic domain, a 22 aa transmembrane region, and a 181 aa extracellular domain. Similar to other TNF ligand family members, LIGHT is predicted to assemble as a homotrimer. LIGHT is produced by activated T cells and was first identified by its ability to compete with HSV glycoprotein D for HVEM binding. LIGHT has also been shown to bind to the Lymphotoxin β Receptor (LTβR) and the decoy receptor (DcR3TR6).

LIGHT plays a unique role in T cell activation and the formation of lymphoid tissue. Interactions between LIGHT and LTβR restore lymphoid structures in the spleen of LTα$^{-/-}$ mice. In addition, the upregulation of LIGHT causes T cell activation and migration into non-lymphoid tissues providing for the formation of lymphoid-like structures. Conversely, LIGHT$^{-/-}$ mice showed impaired T cell activation and delayed cardiac rejection. Therefore, LIGHT is a potent costimulatory molecule that also promotes the formation of lymphoid tissues to enhance local immune responses. Lack of efficient priming of naive T cells in draining lymphoid tissues and the inability to expand tumor-specific T cells within tumors prevent the eradication of cancer.

Micrometastases (small aggregates of cancer cells visible microscopically) can become established at a very early stage in the development of heterogeneous primary tumors, and seed distal tissue sites prior to their clinical detection. For example, the detectable metastasis in breast cancer can be observed when the primary tumor size is very small. Therefore, at the time of diagnosis, many cancer patients already have microscopic metastases, an observation that has led to the development of post-surgical adjuvant therapy for patients with solid tumors. Despite these advances, success has been limited, and optimal treatment of metastatic disease continues to pose a significant challenge in cancer therapy.

A variety of human and murine cancers have been proven to be antigenic and able to be recognized by T cells. Tumor-reactive T cells could theoretically seek out and destroy tumor antigen-positive cancer cells and spare the surrounding healthy tissues. However, the naturally existing T cell responses against malignancies in human are often not sufficient to cause regression of the tumors, primary ones or metastases. It has been reported that sporadic spontaneous, but immunogenic tumors, avoid destruction by inducing T cell tolerance. However, the activation of tumor antigen-specific T cells may completely prevent the development of spontaneous tumors. Thus, breaking tolerance and generating such T cells capable of rejecting tumors around the time of treatment of the primary tumor represents a potential approach to clearing metastatic tumor cells. Because antigen-lost variants can escape under immunological pressure, immunotherapy should be applicable independent of knowledge of specific tumor antigens.

From an immunological perspective, present clinical strategies hinder the immune defense against malignancies and further diminish the effectiveness of immunotherapy. Although removal of a tumor may reverse tumor-induced immune suppression, surgical excision of the primary tumor before immunotherapy also removes the major source of antigen, which may lead to a reduction of the activation of cytotoxic T-lymphocytes (CTL) since the efficiency of priming is correlated with the tumor antigen load. In addition, current adjuvant treatments, which include chemotherapy and radiation therapy, that are meant to kill residual tumor cells may in fact impair anti-tumor immune responses by destroying or inhibiting T cells.

Metastatic disease is the major cause of morbidity and mortality in cancer. While surgery, chemotherapy, or radiation can often control primary tumor growth, successful eradication of disseminated metastases remains rare. One unsolved problem is whether such response allows incoming CTL to be educated and then exit the tumor site. Another unsolved problem is whether these CTL can then patrol and effectively eliminate spontaneously metastasized tumor cells in the periphery. Local treatment of tumors with LIGHT generates plenty of tumor specific CTL that exit the primary tumor and infiltrate distal tumors to completely eradicate preexisting spontaneous metastases.

As indicated above, the naturally occurring T cell responses against malignancies in humans are often not sufficient to cause regression of tumors, primary ones or metastatic cells. Immunotherapy would potentially elicit tumor-reactive T cells that can seek and destroy disseminated tumor antigen-positive cancer cells while sparing the surrounding healthy tissues, but active vaccination for tumor bearing host only shows limited benefit. Lack of well-defined antigens in most tumors limits either active vaccination or adoptive transfer therapy. Immunotherapy that is effective even without determination of specific tumor antigens would be more applicable and more therapeutically feasible. However, it is still unclear when and how to boost active immune responses against tumor tissues.

Naive or effector-memory T cells can leave the periphery and enter the draining lymph nodes through an active process. It is not yet known if sufficient number of tumor-specific CTLs recruited to the primary tumor can survive and exit the microenvironment to patrol peripheral tissues and eradicate disseminated metastases. In addition, a challenge in developing an effective immunotherapy is to devise an approach to increase the number of, or enhance the function of, circulating tumor-specific T cells that may detect and destroy microscopic metastatic cells before they become clinically meaningful. The delivery of LIGHT into the primary tumor can help generate CTL which can then exit out of the local tumor and patrol periphery tissue to eradicate metastases before they are clinically meaningful.

Approved breast cancer therapies include surgery, radiation, chemotherapy, (e.g. doxorubicin, paclitaxel), signaling inhibitors (e.g., Lapatinib, Neratinib), and monoclonal antibodies (e.g. Trastuzumab, Pertuzumab). Herceptin (Trastuzumab) is an approved anti-Her2 antibody therapy for breast cancer. Her2 (human epidermal growth factor receptor 2 (c-erbB2 or neu), is amplified in 25-30% of human breast cancers. Overexpression of Her2 is associated with poorer prognosis.

Humanized monoclonal antibody targeting Her2 employing murine antigen binding residues on human IgG framework, was approved in 1998 by FDA for monotherapy. Overall response rates are between 11.6-35% for monotherapy.

However, there are problems with anti-Her2 antibody therapy. There are lower than desired success of treatment and large non-responsive rate with anti-Her2/neu therapy. Anti-Her2/neu therapy requires prolonged treatment together with chemotherapy to be effective. A majority of patients develop resistance and relapse within a year, and treatment can cost over $100,000 USD.

Several strategies can improve therapeutic antibody efficacy:
  a. cytotoxic or immunomodulatory immunocytokines (IL-2, LIGHT etc.);
  b. drug-conjugates (chemo drugs);
  c. modifying Fc mediated effects, e.g., changing antibody isotypes; modifying affinity or changing Fc receptor binding; and increasing half-life.

Improvements to antigen-antibody binding or design may be sought by:
  a. higher affinity
  b. increased or decreased internalization
  c. increased antibody stability
  d. bi-specific, tri-specific antibodies.

In the present disclosure targeting tumors not just with wild type LIGHT, but with various embodiments of LIGHT generates strong immunity against primary tumor and metastases compared to previous results with wild type LIGHT.

SUMMARY

Targeting tumor cells with embodiments of LIGHT, e.g., mutant LIGHT proteins, peptides or fragments thereof, linked, fused or conjugated to a targeting agent against a tumor reduces the growth of tumors and also reduces metastasis including micro-metastasis. Targeting agents include antibodies. Further, cytokines linked to an antibody against tumor antigens are useful against micrometastasis.

LIGHT, a TNF family member is part of a complex molecular network, and is an excellent candidate for use as an immunocytokine. (FIG. 8)

LIGHT (TNFSF14) is expressed as a trimer on lymphoid tissue, immature DCs and activated T cells.

LIGHT binds LTbR and HVEM on target cells.

LIGHT also binds soluble Decoy Receptor 3 in humans, which is secreted by many tumors.

The interplay of TNF family members controls immune regulation. The three pronged activity of LIGHT makes it an excellent candidate for use as an immunocytokine: LIGHT binds both LTβR and HVEM for immune modulation; interacts with LTβR to increase chemokines and adhesion molecules; and attracts T cells. It activates T cells and NK cells through HVEM for increased immune function and tumor immunity; and directs apoptosis of LTβR or HVEM expressing tumors. (FIG. 9)

Delivery of LIGHT to tumors using an adenoviral approach and in the form of a fusion protein was effective at reducing tumor size and controlling metastases. (FIGS. 10, 11) (Table 1) However, production of fusion constructs using LIGHT has been problematic. There were aggregation and low production problems with scFV(neu)-mLIGHT fusion. Additionally, it was difficult to show effectiveness in murine models because human LIGHT constructs, such as anti-neu(Fab)-hLIGHT had decreased binding affinity to the mouse receptors is compared to wild type LIGHT or mouse LIGHT.

Therefore, a LIGHT molecule with increased stability and affinity was engineered that could be used to generate a scFV(neu)-LIGHT fusion protein or other fusion proteins that could be tested in vitro and in vivo in both mouse models of disease and in humans.

Furthermore, new mutant human LIGHT molecules are disclosed which bind to the mouse receptors of LIGHT with greater affinity than wild type human LIGHT (hLIGHT), and have equal or greater binding to the human receptors of LIGHT, as compared with wild type human LIGHT. Improvements to antibody-mediated cancer therapy and to immunotherapy for the treatment of cancer are disclosed. "Wild type" as used herein refers to amino acid or nucleic acid sequences characteristic of sequences in source mammals, e.g., humans, mouse.

Solutions to producing improved LIGHT and improved LIGHT-targeting agent fusion constructs were achieved in part by the following steps: Human LIGHT (hLIGHT) ("wild type") was used as platform for engineering because it is more stable than mouse LIGHT. A hLIGHT was engineered to have equivalent or greater binding to murine LTbR and HVEM (mLTbR and mHVEM) and human LTbR and HVEM (hLTbR and hHVEM) as well as improved expression and stability, to ease production and increase therapeutic efficacy (FIGS. 17, 18). In that sense, engineered LIGHT molecules were "derived" from LIGHT.

hLIGHT was engineered, and clones were identified with, increased mouse LTβR and mouse HVEM binding (FIG. 21) and favorable binding to human LTβR and human HVEM. (FIG. 23). Confirmation of binding to the mouse and human receptors was conducted in scFV-LIGHT fusions produced in CHO cells (FIG. 23). The human mutant LIGHT constructs were tested in vitro as a fusion protein. 7164-m4-14LIGHT, which is one of the new higher-affinity human mutant LIGHT molecules fused to scFV(neu), slowed the growth of TUBO cells significantly better in comparison to the 7164 antibody alone or human LIGHT alone, as measured by cell count and MTS. (FIGS. 25, 26)

The human mutant LIGHT constructs were tested in vitro and in vivo in an adenoviral construct for its potential function to stimulate host immune responses (FIG. 29). Human LIGHT mutant m4-14 extracellular domain was delivered along with a single-chain fragment (scFv) encoding an anti-neu antibody fragment (ad-neu-mutant LIGHT). Ad-neu-mutant LIGHT improves the CD8+ CTL response to neu both in vitro and in vivo, as compared with a construct containing the unmodified human LIGHT extracellular domain (ad-neu-human LIGHT) (FIGS. 30-32, 35). Ad-neu-mutant LIGHT also stimulates production of increased numbers of anti-neu antibodies, as compared with the construct containing ad-neu-human LIGHT (FIG. 33). When tested as an anti-cancer vaccine, ad-neu-mutant LIGHT is more effective in preventing tumors than a vaccine containing only neu (FIG. 34), and has increased neu-specific cell killing (FIG. 36). LIGHT can stimulate NK cells to produce IFN via the HVEM receptor while stimulating MEFs to produce IL-6 via LTbR. FIG. 37 demonstrates that mutant LIGHT induced much higher IFN-γ production in Rag-1-splenocytes than Wt LIGHT. FIG. 38 demonstrates that mutant LIGHT induced higher IL-6 production in MEF cells than Wt human LIGHT. Therefore, mutant LIGHT is a stronger stimulator than Wt LIGHT.

Inducing an immune response in tumor tissues via an antibody-human-mutant LIGHT fusion, adenoviral delivery of human mutant LIGHT, or a conjugated composition prior to surgery generates sufficient primed antigen-specific effector T cells that exit the tumor and eradicate metastasis. An antibody specific to a cancer antigen and LIGHT that is resistant to protease digestion (e.g., a form of mutant LIGHT in the position 81-84 region of LIGHT) can also be administered separately. Targeting the primary tumor with TNFSF14 (LIGHT) prior to surgical excision is a new strategy to elicit better immune response for the eradication of spontaneous metastases. Treatment with human mutant LIGHT treatment slows down the growth of aggressive tumors.

A composition suitable for cancer therapy includes a tumor specific antibody linked, fused or conjugated to a fragment of a human LIGHT protein, wherein the LIGHT fragment is resistant to protease digestion in a tumor environment and is sufficient to stimulate cytotoxic T lymphocytes against tumor cells.

A suitable composition includes a tumor specific targeting agent and mutant LIGHT amino acid sequences with mutations relative to the human wild type sequence (FIGS. 6 and 7), or a tumor specific targeting agent linked to a fragment of a human mutant LIGHT protein. The targeting agent and the fragment of the human mutant LIGHT protein may form a fusion protein, or the fragment of the LIGHT protein may be chemically conjugated or linked otherwise to the targeting agent or a fragment of the targeting agent.

A composition includes the ability to be delivered to a tumor by suitable methods such as direct injection, adenoviral vectors, microspheres or nanoparticles.

Any peptide fragment derived from LIGHT proteins including recombinant peptides, synthetic peptides, recombinant LIGHT proteins, mutant LIGHT proteins, truncated LIGHT proteins, extracellular domains of LIGHT, conserved domains of LIGHT, peptide mimetics that resemble a LIGHT domain, LIGHT proteins or peptides thereof with modified amino acids are suitable for use in inducing immune response by linking, fusing or conjugating them a tumor specific agent, such as, for example, an antibody or a fragment thereof, provided the LIGHT fragment is capable of being stably present on a tumor cell surface and has increased affinity for mouse and human receptors of LIGHT.

A suitable composition includes a humanized monoclonal antibody or a chimeric antibody or a heterominibody or a single chain antibody.

An antibody fragment used in conjunction with LIGHT is sufficient to recognize a tumor antigen. The fragment is sufficient to stimulate cytotoxic T lymphocytes.

A fragment of LIGHT may include about 100-150 amino acids of LIGHT. A fragment of LIGHT may have an amino acid sequence corresponding to positions about 85-240 of LIGHT. A fragment of LIGHT may also include about 100-150 amino acids of LIGHT. A fragment of LIGHT may include an amino acid sequence from positions about 90-240 of LIGHT. A fragment of LIGHT may include an amino acid sequence from positions about 84-240 or 83-240 or 82-240 of LIGHT.

A fragment of LIGHT may also include about 100-150 amino acids of LIGHT, provided the fragment is capable of inducing an immune response against tumor cells. A fragment of LIGHT may include an amino acid sequence from positions about 90-235 of LIGHT.

A fragment of LIGHT includes a protease resistant fragment. A fragment of LIGHT may include a mutation in a protease recognition sequence EQLI (SEQ ID NO: 1).

Compositions that include the novel human mutant LIGHT extracellular domains, are suitable for cancer treatment. A composition is disclosed wherein the LIGHT fragment includes an extracellular domain with at least one of the following an amino acid sequences:

```
                                                 (SEQ ID NO: 2)
QLHWRLGEMVTRLPDGPAGSWEQLIQERRSHEVNPAAHLTGANSSLTG

SGGPLLWETQLGLAFLRGLSYHDGALVVTKAGYYYIYSKVQLGGVGCP

LGLASTITHGLYICRTPRYPEELELLVSQQSPCGRATSSSRVWWDSSF

LGGVVHLEAGEKVVVRVLDERLVRLRDGTRSYFGAFMV.
```

A composition is disclosed wherein the LIGHT fragment includes an extracellular domain with an amino acid sequence:

```
                                                 (SEQ ID NO: 3)
RRSHEVNPAAHLTGANSSLTGSGGPLLWETQLGLAFLSGLSYHDGALV

VTKAGYYYIYSKVQLRGVGCPLGLASTITHGLYKRTPRYPEELELLVS

QQSPCGRATSSSRVWWDSSFLGGVVHLEAGEEVVVRVLGERLVRLRDG

TRSYFGAFMV
```

A composition is disclosed wherein the LIGHT fragment includes an extracellular domain with an amino acid sequence:

```
                                                 (SEQ ID NO: 4)
RRSHEVNPAAHLTGANSSSTGSGGPLLWETQLGLAFLRGLSYHDGALV

VTKAGYYYIYSKVQLRGVGCPLGLASTITHGLYKRTPRYPEELELLVS

QQSPCGRATSSSRVWWDSSFLGGVVHLEAGEEVVVRVLDERLVRLRDG

TRSYFGAFMV
```

A composition is disclosed wherein the LIGHT fragment includes an extracellular domain with an amino acid sequence:

```
                                                 (SEQ ID NO: 5)
RRSHEVNPAAHLTGANFSLTGSGGPLLWETQLGQAFLRGLSYHDGALV

VTKAGYYYIYSKVQLGGVGCPLGLASTITHGLYKRTPRYPEELELLVS

QQSPCGRATSSSRVWWDSSFLGGVVHLEAGEEVVVRVLDDRLVRLRDG

TRSYFGAFMV
```

A composition is disclosed wherein the LIGHT fragment includes an extracellular domain with an amino acid sequence:

```
                                                 (SEQ ID NO: 6)
RRSHEVNPAAHLTGANSSLTGSGGPLLWETQLGLAFLRGLSYHDGALV

VTKAGYYYIYSKVQLRGVGCPLALASTITHGLYKRTPRYPEELELLVS

QQSPCGRATSSSRVWWDSSFLGGVVHLEAGEEVVVRVLDERLDLRDGT

RSYFGAFMV
```

A composition is disclosed wherein the LIGHT fragment includes an extracellular domain with an amino acid sequence:

```
                                                 (SEQ ID NO: 7)
RRSHEVNPAAHLTGANSSLTGSGGPLLWETQLGLAFLRGLSYHDGALV

ATKAGYYYIYSKVQLGGVGCPLGLASTITHGLYKRTPRYPEELELMVS

QQSPCGRATSSSRVWWDSSFLGGVVHLEAGEEVVVRVPDERLVRLRDG

TRSYFGAFMV
```

A composition is disclosed wherein the LIGHT fragment includes an extracellular domain with an amino acid sequence:

```
                                                 (SEQ ID NO: 8)
RRSHEVNPAAHLTGANFSLTGSGGPVLWETQLGLAFLRGLSYHDGAL

VVTKAGYYYIYSKLQLGGVGCPLGLAGTITHGLYKRTPRYPEELELL

VSQQSPCGRATSSSRAWWDSSFLGGVVHLEAGEEVVVRVLDERLVRL

RDGTRSYFGAFMV
```

A composition is disclosed wherein the LIGHT fragment includes an extracellular domain with an amino acid sequence:

```
                                                 (SEQ ID NO: 8)
RRSHEVNPAAHLTGANFSLTGSGGPVLWETQLGLAFLRGLSYHDGALV

VTKAGYYYIYSKLQLGGVGCPLGLAGTITHGLYKRTPRYPEELELLVS
```

QQSPCGRATSSSRAWWDSSFLGGVVHLEAGEEVVVRVLDERLVRLRDG

TRSYFGAFMV

A composition is disclosed wherein the LIGHT fragment includes an extracellular domain with an amino acid sequence:

(SEQ ID NO: 9)
RRSHEVNPAAHLTGANSSLTGSGGPLLWETQLGLAFLRGLSYHDGALV

VTKAGYYYIYSKVQLRGVGCPLGLASTITHGLYKRTPRYPEELELLVN

QQSPCGRAPSSSRVWWDSSFLGGVVHLEAGEEVVVRVLDERLVRLRDG

TRSYFGAFMV

A composition is disclosed wherein the LIGHT fragment includes an extracellular domain with an amino acid sequence:

(SEQ ID NO: 10)
RRSHEVNPAAHLTGANSSLTGSGGPLLWETQLGLAFLRGLSYHDGALV

VTKAGYYYIYSKVQLRGVGCPLGLASTIAHGLYKRTPRYPEELELLVS

QQSPCGRATSGSRVWWDSSFLGGVVHLEAGEEVVVRVLDERLVRLRDG

TRSYFGAFMV

A composition is disclosed wherein the LIGHT fragment includes an extracellular domain with an amino acid sequence:

(SEQ ID NO: 10)
RRSHEVNPAAHLTGANSSLTGSGGPLLWETQLGLAFLRGLSYHDGALV

VTKAGYYYIYSKVQLRGVGCPLGLASTIAHGLYKRTPRYPEELELLVS

QQSPCGRATSGSRVWWDSSFLGGVVHLEAGEEVVVRVLDERLVRLRDG

TRSYFGAFMV

A composition is disclosed wherein the LIGHT fragment includes an extracellular domain with an amino acid sequence:

(SEQ ID NO: 5)
RRSHEVNPAAHLTGANFSLTGSGGPLLWETQLGQAFLRGLSYHDGALV

VTKAGYYYIYSKVQLGGVGCPLGLASTITHGLYKRTPRYPEELELLVS

QQSPCGRATSSSRVWWDSSFLGGVVHLEAGEEVVVRVLDDRLVRLRDG

TRSYFGAFMV

A composition is disclosed wherein the LIGHT fragment includes an extracellular domain with an amino acid sequence:

(SEQ ID NO: 11)
RRSHEVNPAAHLTGANSSLTGSGGPLLWETQLGLAFLRGLSYHDGALV

VTKAGFYYIYSKVQLGGVGCPLGRASTITHGLYKRTPRYPEELELLVS

QQSPCGRATSSSRVWWDSSFLGGVVHLEAGEEVVVRVLDERLVRLRDG

TRSYFGAFMV

A composition is disclosed wherein the LIGHT fragment includes an extracellular domain with an amino acid sequence:

(SEQ ID NO: 12)
RRSHEVNPAAHLTGANSSLTGSGGPLLWETQLGLAFLRGLSYHDGALV

ATKAGYYYIYSKVQLGGVGCPLGLASTISHGLYKRTPRYPEELELLVS

LRSPCGRATSSSRVWWDSSFLGGVVHLEAGEEVVVRVLDERLVRLRDG

TRSYFGAFMV

A composition is disclosed wherein the LIGHT fragment includes an extracellular domain with an amino acid sequence:

(SEQ ID NO: 13)
RRSHEVNPAAHLTGANSSLTGSGGPLLWETQLGLAFLRGLSYHDGALV

VTKAGYYYIYSKVQLGGVGCPLGLASTITHGLYKRTPRYPEELELLVN

QQSPCGRATSSSRVWWDSSFLGGVVHLEAGEEVVVRVPDERLVRLRDG

TRSYFGAFMV

A composition is disclosed wherein the LIGHT fragment includes an extracellular domain with an amino acid sequence:

(SEQ ID NO: 12)
RRSHEVNPAAHLTGANSSLTGSGGPLLWETQLGLAFLRGLSYHDGALV

ATKAGYYYIYSKVQLGGVGCPLGLASTISHGLYKRTPRYPEELELLVS

LRSPCGRATSSSRVWWDSSFLGGVVHLEAGEEVVVRVLDERLVRLRDG

TRSYFGAFMV

A composition is disclosed wherein the LIGHT fragment includes an extracellular domain with an amino acid sequence:

(SEQ ID NO: 14)
RRSHEVNPAAHLTGANSSLTGSGGPLLWETQLGQAFLRGLSYHDGALV

VTKAGYYYIYSKVQLRGVGCPLGLASTITHGLYKRTPRYPEELELLVS

QQSPCGRATSSSRVWWDSSFLGGVVHLEAGEKVVVRVLDERLARLRDG

TRSYFGAFMV

A composition is disclosed wherein the LIGHT fragment includes an extracellular domain with an amino acid sequence:

(SEQ ID NO: 15)
RRSHEVNPAAHLTGANSSLTGSGGPLLWETQLGQAFLRGLSYHDGALV

VTKAGYYYIYSKVQLGGVGCPLGLANTITHGLYKRTPRYPEELELLVS

QQSPCGRATSSSRMWWDSSFLGGVVHLEAGEKVVVRVLDERLVRLRDG

TRSYFGAFMV

A composition is disclosed wherein the LIGHT fragment includes an extracellular domain with an amino acid sequence:

(SEQ ID NO: 16)
RRSHEVNPAAHLTGANSSLTGSGGPLLWETQLGLAFLRGLSYHDGALV

VTKAGYYYIYSKVQLRGVGCPLGLASPITHGLYKRTPRYPEELELLVS

A composition is disclosed wherein the LIGHT fragment includes an extracellular domain with an amino acid sequence:

(SEQ ID NO: 17)
RRSHEVNPAAHLTGANSSLTGSGGPLLWETQLGLAFLRGLSYHDGALVV

TKAGYYYIYSKVQLGGVGCPLGLASTFTHGLYKRTPRYPEELELLVSQQ

SPCGRASSSRVWWDSSFLGGVVHLEAGEKVVVRVLDERLVRLRDGTRS

YFGAFMV

A composition is disclosed wherein the LIGHT fragment includes an extracellular domain with an amino acid sequence:

(SEQ ID NO: 18)
RSHEVNPAAHLTGANSSLTGSGGPLLWETQLGLAFLRGLSYHDGALVVT

KTGYYYIYSKVQLGGVGCPLGLAGTITHGLYKRTPRYPEELELLVSQQS

PCGRATSSSRVWWDSSFLGGVVHLEAGEKVVVRVLGKRLVRLRDGTRSY

FGAFMV

A composition is disclosed wherein the LIGHT fragment includes an extracellular domain with an amino acid sequence:

(SEQ ID NO: 19)
RRSHEVNPAAHLTGANSNLTGSGGPLLWETQLGLAFLRGLSYHDGALV

VTKAGYYYIYSKVQLGGVGCPLGLASTITHGLYKRTPRYPEELELLVS

QQSPCGRATSSSRVWWDSSFLGGVVHLEAGEKVVVRVQDERLVRLRDG

TRSYFGAFMV

A composition is disclosed wherein the LIGHT fragment includes an extracellular domain with an amino acid sequence:

(SEQ ID NO: 20)
RRSHEVNPAAHLTGANSSLTGSGGPLLWETQLGLAFLRGLSYHDGALV

VTKTGYYYIYSKVQLGGVGCPLGLAGTITHGLYKRTPRYPEELELLVS

QQSPCGRATSSSRVWWDSSFLGGVVHLEAGEKVVVRVLGKRLVRLRDG

TRSYFGAFMV

A composition is disclosed wherein the LIGHT fragment includes an extracellular domain with an amino acid sequence:

A composition is disclosed wherein the LIGHT fragment includes an extracellular domain with an amino acid sequence:

(SEQ ID NO: 21)
RRSHEVNPAAHLTGANSSLTGSGGPLLWEPQLGLAFLRGLSYHDGALV

VTKAGYYYIYSKVQLRGVGCPLGLTRTITHGLYKRTPRYPEELELLVS

QQSPCGRATPSSRVWWDSSFLGGVVHLEAGEKVVVRVLDERLVRLMDG

TRSYFGAFMV

A composition is disclosed wherein the LIGHT fragment includes an extracellular domain with an amino acid sequence:

(SEQ ID NO: 22)
RGSHEVNPAAHLTGASSSLTGSGGPLLWETQLGLAFLRGLSYHDGALV

VTKAGYYYIYSKVQLRGVGCPLGLASTITHGLYKRTPRYPEELELLVS

QQSPCGRATSSSRVWWDSSFLGGVVHLEAGEEVVVRVLDERLVRLRDG

TRSYFGAFMV

A composition is disclosed wherein the LIGHT fragment includes an extracellular domain with an amino acid sequence:

(SEQ ID NO: 23)
RRSHEVNPAAHLTGANSSLTGSGGPLLWETQLGLAFLRGLSYHDGALV

VTKAGYYYIYSKVQLGGVGCPLGRASTITHGLYKRTPRYPEELELLVS

QQSPCGRATSSSRVWWDSSFLGGVVHLEAGEKVVVRVQDERLVRLRDG

TRSYFGAFMV

A composition is disclosed wherein the LIGHT fragment includes an extracellular domain with an amino acid sequence:

(SEQ ID NO: 24)
RSHEVNPAAHLTGANSSLTGSGGPLLWETQLGLSFLRGLSYHDGALVV

TKAGYYYIYSKVQLRGVGCPLGLASTITHGLYKRTPRYPEELELLVSQ

QSPCGRATSSSRVWWDSSSLGGVVHLEAGEKVVVRVLDERLVRLMDGT

RSYFGAFMV

A composition is disclosed wherein the LIGHT fragment includes an extracellular domain with an amino acid sequence:

(SEQ ID NO: 20)
RRSHEVNPAAHLTGANSSLTGSGGPLLWETQLGLAFLRGLSYHDGALV

VTKTGYYYIYSKVQLGGVGCPLGLAGTITHGLYKRTPRYPEELELLVS

QQSPCGRATSSSRVWWDSSFLGGVVHLEAGEKVVVRVLGKRLVRLRDG

TRSYFGAFMV

A composition is disclosed wherein the LIGHT fragment includes an extracellular domain with an amino acid sequence:

(SEQ ID NO: 25)
QRSHEVNPAAHLTGANSSPTGSGGPLLWETQLGLAFLRGLSYHDGALV

VTKAGYYYIYSKVQLGGVGCPLGLASTITHGLYKRTPRYPEELELLVS

LQSPCGRATSSSRVWWDSSFLGGVVHLEAGEKVVVRVLDERLVRPRDG

TRSYFGAFMV

Novel human LIGHT extracellular domains that binds to human and mouse receptors are listed in FIGS. 6, 7 and 28.

The LIGHT mutants disclosed herein are unexpected in both their biological properties and their efficacy. As shown in FIG. 21 ("hLIGHT mutants have increased binding affinity to mLTbR and mHVEM") these new mutants not only have an increased binding affinity for the mouse LIGHT receptors, but also have significantly increased binding affinity for the human LIGHT receptors, as compared with wild-type human LIGHT. In addition, these mutants have increased stability, as compared with the wild type human LIGHT. In addition to their significantly improved cross-species affinity, these mutants are also substantially more efficacious in cell killing than the wild-type human LIGHT, as shown in FIGS. 31 and 32 (Super LIGHT can improve CD8 CTL response to neu—in vivo killing"). It could not have been predicted by one of skill in the art at the time of this invention that mutants of LIGHT could be generated that would possess these properties. FIGS. 6 and 7 shows that many of the mutants have the K at 214 mutated to E, which is also what is in the mouse sequence. Of particular interest are mutants m4-14, m4-7, and m4-16.

A method of reducing the growth of primary tumor and/or cancer metastasis, includes the steps of:

administering a pharmaceutical composition comprising a tumor-specific antibody linked to at least one of the embodiments of LIGHT, e.g., to a fragment; and reducing the growth of primary tumor and/or cancer metastasis by stimulating activation of tumor-specific T-cells against the tumor.

The antibody recognizes a surface tumor antigen and the antibody may be conjugated to the LIGHT fragment chemically or recombinantly fused or linked otherwise to the LIGHT fragment.

The pharmaceutical composition including the antibody-LIGHT may be administered intravenously or by other methods known to those of skill or disclosed herein.

A method of reducing the growth of primary tumor and/or cancer metastasis, includes the steps of:

(a) administering a pharmaceutical composition comprising a tumor-specific antibody linked to at least one embodiment of LIGHT;

(b) introducing a nucleic acid molecule encoding the LIGHT embodiment thereof into an individual at a tumor site, wherein the LIGHT is protease resistant; and (c) reducing the growth of primary tumor cancer metastasis by stimulating activation of tumor-specific T-cells against the tumor.

The nucleic acid may be delivered to a pre-existing tumor site or to a site distal to a pre-existing tumor site.

A chemotherapeutic agent may also be administered during or prior to or after an antibody-LIGHT therapy.

Radiotherapy may also be administered during or prior to or after LIGHT therapy.

Embodiments of the antibody specific to a tumor antigen may be selected from the group consisting of HER2, HER4, HERB, STEAP, c-MET, EGFR, alphafetoprotein (AFP), carcinoembryonic antigen (CEA), CA-125, MUC-1, epithelial tumor antigen (ETA), tyrosinase, melanoma-associated antigen (MAGE), abnormal products of ras, or p53, DcR3 and any other anti-cancer antigen.

A method of reducing the growth of primary tumor and/or cancer metastasis, includes the steps of:

(a) administering a pharmaceutical composition comprising a tumor-specific antibody;

(b) introducing a nucleic acid molecule encoding a LIGHT protein or a fragment thereof at a tumor site, wherein the LIGHT is protease resistant;

(c) expressing the LIGHT protein or a fragment thereof on the surface of a tumor cell; and (d) reducing the growth of the tumor and/or cancer metastasis by stimulating activation of tumor-specific T-cells against the tumor.

A chimeric protein including a peptide region that recognizes a tumor antigen and a fragment of a LIGHT protein is disclosed. The agent may be a ligand that binds a tumor surface receptor.

A composition is described including a fragment of a LIGHT protein and an agent that specifically recognizes a tumor cell.

A pharmaceutical composition includes a LIGHT peptide fragment coupled with a tumor specific component. The tumor specific component may include a ligand to a receptor in a tumor cell surface or a receptor that recognizes a ligand on tumor cell surface.

A novel method to treat tumors (solid tumors in particular) is to create lymphoid-like microenvironments that express chemokines, adhesion molecules, and costimulatory molecules required for priming naive T cells and expanding activated T cells by the use of mutant LIGHT molecules. Broader T cells are generated against tumors. Direct delivery of antibody-LIGHT fusion or conjugates are effective against tumors and metastasis. Tumor volume is reduced in vivo when antibody-LIGHT conjugates or fusion products are targeted to tumors as compared to tumors treated with controls.

In various embodiments, the mutant human LIGHT has an amino acid change in a proteolytic site including an amino acid sequence EQLI (SEQ ID NO: 1) from positions 81-84 of native LIGHT protein. In an embodiment, the mutant LIGHT does not have the proteolytic site, an amino acid sequence EQLI (SEQ ID NO: 1) from positions 81-84 of native LIGHT protein.

In various embodiments, the mutant human LIGHT has an amino acid change at position 214 wherein the lysine at position 214 is changed to a glutamic acid.

The nucleic acid molecule disclosed encodes a recombinant LIGHT including an extracellular domain:

```
                                              (SEQ ID NO: 26)
QLHWRLGEMVTRLPDGPAGSWEQLIQERRSHEVNPAAHLTGANSSLTG

SGGPLLWETQLGLAFLRGLSYHDGALVVTKAGYYYIYSKVQLGGVGCP

LGLASTITHGLYKRTPRYPEELELLVSQQSPCGRATSSSRVWWDSSFL

GGVVHLEAGEKVVVRVLDERLVRLRDGTRSYFGAFMV.
```

Cancer metastasis is reduced by stimulation of cytotoxic T-lymphocytes, and/or by stimulation of chemokines, adhesion molecules, and costimulatory molecules for priming naive T-cells. T-cells are activated within a tumor site, and may circulate in blood. Circulating T-cells are preferably cancer specific. The T-cell generation may be CD8+ dependent.

An isolated recombinant nucleic acid includes a nucleotide sequence encoding a protease digestion resistant mutant LIGHT. An embodiment of the nucleotide sequence is:

```
                                              (SEQ ID NO: 27)
ATGGAGGAGAGTGTCGTACGGCCCTCAGTGTTTGTGGTGGATGGACAG

ACCGACATCCCATTCACGAGGCTGGGACGAAGCCACCGGAGACAGTCG

TGCAGTGTGGCCCGGGTGGGTCTGGGTCTCTTGCTGTTGCTGATGGGG
```

-continued

```
GCTGGGCTGGCCGTCCAAGGCTGGTTCCTCCTGCAGCTGCACTGGCGT

CTAGGAGAGATGGTCACCCGCCTGCCTGACGGACCTGCAGGCTCCTGG

GAGCAGCTGATACAAGAGCGAAGGTCTCACGAGGTCAACCCAGCAGCG

CATCTCACAGGGGCCAACTCCAGCTTGACCGGCAGCGGGGGCCGCTG

TTATGGGAGACTCAGCTGGGCCTGGCCTTCCTGAGGGGCCTCAGCTAC

CACGATGGGCCCTTGTGGTCACCAAAGCTGGCTACTACTACATCTAC

TCCAAGGTGCAGCTGGGCGGTGTGGGCTGCCCGCTGGGCCTGGCCAGC

ACCATCACCCACGGCCTCTACAAGCGCACACCCCGCTACCCCGAGGAG

CTGGAGCTGTTGGTCAGCCAGCAGTCACCCTGCGGACGGGCCACCAGC

AGCTCCCGGGTCTGGTGGGACAGCAGCTTCCTGGGTGGTGTGGTACAC

CTGGAGGCTGGGGAGAAGGTGGTCGTCCGTGTGCTGGATGAACGCCTG

GTTCGACTGCGTGATGGTACCCGGTCTTACTTCGGGGCTTTCATGGTG

TGA,
``` wherein the sequence encoding the protease digestion site GAGCAGCTGATA (SEQ ID NO: 28) is mutated.

Wild type human LIGHT DNA sequence (sequence encoding a protease site EQLI (SEQ ID NO: 1) is shown in bold):

(SEQ ID NO: 29)
```
ATGGAGGAGAGTGTCGTACGGCCCTCAGTGTTTGTGGTGGATGGACAG

ACCGACATCCCATTCACGAGGCTGGGACGAAGCCACCGGAGACAGTCG

TGCAGTGTGGCCCGGGTGGGTCTGGGTCTCTTGCTGTTGCTGATGGGG

GCTGGGCTGGCCGTCCAAGGCTGGTTCCTCCTGCAGCTGCACTGGCGT

CTAGGAGAGATGGTCACCCGCCTGCCTGACGGACCTGCAGGCTCCTGG

GAGCAGCTGATACAAGAGCGAAGGTCTCACGAGGTCAACCCAGCAGCG

CATCTCACAGGGGCCAACTCCAGCTTGACCGGCAGCGGGGGCCGCTG

TTATGGGAGACTCAGCTGGGCCTGGCCTTCCTGAGGGGCCTCAGCTAC

CACGATGGGCCCTTGTGGTCACCAAAGCTGGCTACTACTACATCTAC

TCCAAGGTGCAGCTGGGCGGTGTGGGCTGCCCGCTGGGCCTGGCCAGC

ACCATCACCCACGGCCTCTACAAGCGCACACCCCGCTACCCCGAGGAG

CTGGAGCTGTTGGTCAGCCAGCAGTCACCCTGCGGACGGGCCACCAGC

AGCTCCCGGGTCTGGTGGGACAGCAGCTTCCTGGGTGGTGTGGTACAC

CTGGAGGCTGGGGAGAAGGTGGTCGTCCGTGTGCTGGATGAACGCCTG

GTTCGACTGCGTGATGGTACCCGGTCTTACTTCGGGGCTTTCATGGTG

TGA-3'.
```

Native human LIGHT amino acid sequence (protease digestion site is bold underlined):

(SEQ ID NO: 30)
MEESVVRPSVFVVDGQTDIPFTRLGRSHRRQSCSVARVGLGLLLLLMG

AGLAVQGWFLLQLHWRLGEMVTRLPDGPAGSWEQLIQERRSHEVNPAA

HLTGANSSLTGSGGPLLWETQLGLAFLRGLSYHDGALVVTKAGYYYIY

SKVQLGGVGCPLGLASTITHGLYKRTPRYPEELELLVSQQSPCGRATS

SSRVWWDSSFLGGVVHLEAGEKVVVRVLDERLVRLRDGTRSYFGAFMV

One aspect of a mutant human LIGHT amino acid sequence (EQLI (SEQ ID NO: 1) is absent, indicated by dots): MEESVVRPSVFVVDGQTDIPFTRLGR-SHRRQSCSVARVGLGLLLLLMG AGLAVQGWFLLQL-HWRLGEMVTRLPDGPAGSW . . . QERRSHEVN PAAHLTGANSSLTGSGGPLLWETQLGLAFLRGLSYH-DGALVVTKAGYY YIYSKVQLGGVGCPLGLASTITH-GLYKRTPRYPEELELLVSQQSPCGR ATSSSRVW-WDSSFLGGVVHLEAGEKVVVRVLDERLVRLRDGTR-SYFGA FMV (SEQ ID NO: 31).

Codon optimized nucleotide sequence for mouse mutant LIGHT, starting ATG is highlighted in bold:

(SEQ ID NO: 32)
```
GGGCGAATTGGGTACCGGATCCGCCACCATGGAGAGCGTGGTGCAGCCCAGCGTGTTCGT
1---------+---------+---------+---------+---------+---------+

GGTGGACGGCCAGACCGACATCCCCTTCAGGAGGCTGGAGCAGAACCACAGGCGGAGGAG
61--------+---------+---------+---------+---------+----------+

ATGTGGCACCGTGCAGGTGTCCCTGGCCCTGGTGCTGCTGCTGGGCGCTGGCCTGGCCAC
121-------+---------+---------+---------+---------+----------+

CCAGGGCTGGTTTCTGCTGAGGCTGCACCAGAGGCTGGGCGACATCGTGGCCCACCTGCC
181-------+---------+---------+---------+---------+----------+

CGATGGCGGCAAGGGCAGCTGGCAGGACCAGAGGAGCCACCAGGCCAACCCTGCCGCCCA
241-------+---------+---------+---------+---------+----------+

CCTGACAGGCGCCAACGCCAGCCTGATCGGCATCGGCGGACCCCTGCTGTGGGAGACCAG
301-------+---------+---------+---------+---------+----------+

GCTGGGCCTGGCTTTCCTGAGGGGCCTGACCTACCACGACGGCGCCCTGGTGACCATGGA
361-------+---------+---------+---------+---------+----------+
```

```
GCCCGGCTACTACTACGTGTACAGCAAGGTGCAGCTGTCCGGAGTGGGCTGCCCTCAGGG
421---------+---------+---------+---------+---------+---------+

CCTGGCCAACGGCCTGCCCATCACCCACGGCCTGTACAAGAGGACCAGCAGATACCCCAA
481---------+---------+---------+---------+---------+---------+

GGAGCTGGAGCTGCTGGTCTCCAGGCGGAGCCCCTGTGGCAGGGCCAACAGCAGCCGAGT
591---------+---------+---------+---------+---------+---------+

GTGGTGGGACAGCAGCTTCCTGGGCGGCGTGGTGCACCTGGAGGCCGGCGAGGAGGTGGT
601---------+---------+---------+---------+---------+---------+

GGTGAGGGTGCCCGGCAACAGGCTGGTGAGGCCCAGGGACGGCACCAGGAGCTACTTCGG
661---------+---------+---------+---------+---------+---------+

CGCCTTCATGGTGTGATGAGCGGCCGCGAGCTCCAGCTTTTGTTCCC
721---------+---------+---------+---------+-------

GCGGAAGTACCACACTACTCGCCGGCGCTCGAGGTCGAAAACAAGGG
```

Codon optimized nucleotide sequence for human mutant LIGHT, starting ATG is highlighted in bold.

(SEQ ID NO: 33)
```
GAATTCGAGCTCGGTACCCGACACGGTACCGGATCCGCCACCATGGAG
GAGAGCGTTGTGAGGCCCAGCGTGTTCGTGGTGGACGGCCAGACCGAC
ATCCCCTTCACCCGGCTGGGCCGGAGCCACCGGAGGCAGAGCTGCTCC
GTGGCCAGAGTGGGGCTGGGCCTGCTGCTCCTGCTGATGGGAGCCGGC
CTGGCCGTGCAGGGCTGGTTCCTGCTGCAGCTGCACTGGCGGCTGGGC
GAGATGGTGACCCGGCTGCCCGATGGCCCTGCCGGCAGCTGGCAGGAG
CGGCGGAGCCACGAGGTGAACCCTGCCGCCCACCTGACCGGCGCCAAC
AGCAGCCTGACCGGCAGCGGCGGACCCCTGCTGTGGGAGACCCAGCTG
GGCCTGGCCTTCCTGAGGGGCCTGAGCTACCACGACGGCGCCCTGGTG
GTGACCAAGGCCGGCTACTACTACATCTACAGCAAGGTGCAGCTGGGC
GGAGTGGGCTGCCCTCTGGGGCTGGCCAGCACCATCACCCACGGCCTG
TACAAGCGGACCCCCAGATACCCCGAGGAGCTGGAGCTGCTGGTGTCC
CAGCAGAGCCCCTGTGGCAGGGCCACCTCCAGCAGCCGGGTGTGGTGG
GACAGCAGCTTCCTGGGCGGCGTGGTGCACCTGGAGGCCGGCGAGAAA
GTGGTTGTGAGGGTGCTGGACGAGCGGCTTGTGAGGCTGAGGGACGGC
ACCCGGAGCTACTTCGGCGCCTTCATGGTGTGATGAGCGGCCGCGAGC
TCGTCTCGGGGATCCTCTAGAGTCGACCTGCAGGCATGCAAGCTTG
```

BRIEF DESCRIPTION OF THE DRAWINGS

FIG. 3 discloses the "SL: Short linker" and "LL: Long linker" sequences as SEQ ID NOS 41 and 42, respectively.

FIG. 6 shows the protein sequences of the new human light mutants. The mutated amino acids are noted in bold, italics and underlining. Many of the mutants relative to human wild type LIGHT have K mutated to E at position 214-similar to the mouse sequence. FIG. 6 discloses SEQ ID NOS 43-44, 6-8, 8-10, 10, 4, 3, 5, 5, 11-13, 12, 14-17, 20, 19-23, 45, 20, and 25, respectively, in order of appearance.

FIG. 7 lists amino acid sequences for novel human LIGHT mutants. Of particular interest are m4-14, m4-7 and m4-16. FIG. 7 discloses SEQ ID NOS 6-8, 8-10, 10, 4, 3, 5, 5, 11-13, 12, 14-17, 20, 19-23, 45, 20, and 25, respectively, in order of appearance.

FIG. 12 discloses SEQ ID NO: 35.

FIG. 28 shows nucleic acid sequence of the human LIGHT extracellular domain (SEQ ID NO: 46) and the human LIGHT m4-14 (SEQ ID NO: 47) nucleic acid sequence.

DETAILED DESCRIPTION

Figure 1:
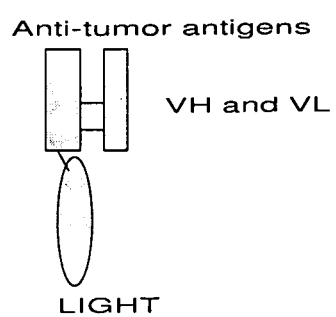
FIG. 1 shows schematic illustrations of the AG 104A tumor specific heterodireic constructs. Human C.kappa. was fused via the flexible upper hinge region of human IgG3 to the C-terminus of a scFv-fragment that was derived from a cancer antigen.

Metastatic disease is a major cause of mortality among cancer patients. Initial dormancy of metastasis or small primary tumors may be attributed to the insufficient levels of antigens available to prime CD8+ T cells. Therapeutic methods that utilize LIGHT and mutants of human LIGHT can effectively target CD8+ T cells. Combining LIGHT or human mutant LIGHT with an antibody that recognizes an antigen expressed by tumor cells (antibody-LIGHT) can specifically and effectively target migrant tumor cells after such Antibody-LIGHT is introduced systemically by intravenous (i.v.) injection.

As an example, in a mouse model, a high-affinity monoclonal antibody against tumor cells accumulates inside tumors in vivo with high concentration after intravenous injection. The heterominibody LIGHT (by conjugation or genetic linkage) allows LIGHT to be specifically delivered into tumor tissue at various distal sites after its systemic introduction.

A LIGHT fusion protein (e.g., antibody-LIGHT couple) selectively accumulates inside tumor tissues and specifically binds to tumors in vitro.

Therapeutic methods that utilize an antibody recognizing an antigen expressed by tumor cells coupled with LIGHT (antibody-LIGHT) are designed to specifically and effectively target migrant tumor cells after the Antibody-LIGHT is introduced systemically by intravenous injection. Any tumor antigen that is expressed on the surface of the tumor cell or is capable of being recognized by a tumor-specific antibody is suitable to be coupled with LIGHT or a functional fragment thereof.

Local delivery of a protease resistant LIGHT (e.g., a mutant LIGHT or an extracellular domain of LIGHT) enhances direct presentation of tumor antigens to antigen-specific T cells and prevents anergy of infiltrated T cells within the tumor microenvironment. In addition, LIGHT may enhance tumor apoptosis in vivo.

Successful eradication of metastasis by currently available cancer treatments remains rare. Generating immune responses in primary tumor tissues prior to surgical resection produces tumor-specific effector T cells sufficient to eradicate distant metastases. Priming of tumor-specific CD8+ T cells, for example by antibody-LIGHT delivery in the primary tumor promotes subsequent exit of cytotoxic T lymphocytes (CTL) that home to distal tumors. Targeting primary tumor prior to surgical excision elicits immune-mediated eradication of spontaneous metastasis.

Metastasis is often a fatal step in the progression of solid malignancies. Disseminated metastatic tumor cells can remain dormant and clinically undetectable for months or even years following surgical resection of the primary tumor, leading to subsequent clinical disease recurrence. Immunotherapeutic strategies are suitable to eliminate this micrometastatic disease. As an example, delivery of antibody-LIGHT into the primary tumor reduces the formation of metastasis and rejects the established metastasis in peripheral tissues. For example, direct delivery of LIGHT in the form of an antibody-LIGHT fusion protein to tumors (e.g., primary tumor) generates sufficient number of effector/memory T cells from the tumor tissues that move to a distal site, leading to an overall increase in the intensity of the immune response, greater inflammatory cytokine production, and the eradication of spontaneous metastasis. Immunotherapy using primary tumor tissues aimed to provoke and sustain a tumor specific immune response in the presence of endogenous tumor antigens generates the necessary CTL to clear already disseminated tumor cells.

In the presence of LIGHT on the surface of a tumor, CTLs are efficiently primed and subsequently circulate to infiltrate LIGHT-negative distal tumors. Without the benefits of LIGHT being present in the primary tumor, few activated T cells are expected at a secondary tumor site. It is likely that these effector/memory T cells generated in the local tumor site in the presence of LIGHT are able to exit the tumor and patrol the periphery and identify metastatic tumor cells. Chemokine receptor (CCR7) has been recently shown to be a key molecule for T cells to exit the peripheral tissues, including the inflammatory site, and traffic to the draining LN. The 2C T cells exiting LIGHT-expressing tumors may be controlled by CCR7.

Figure 2:
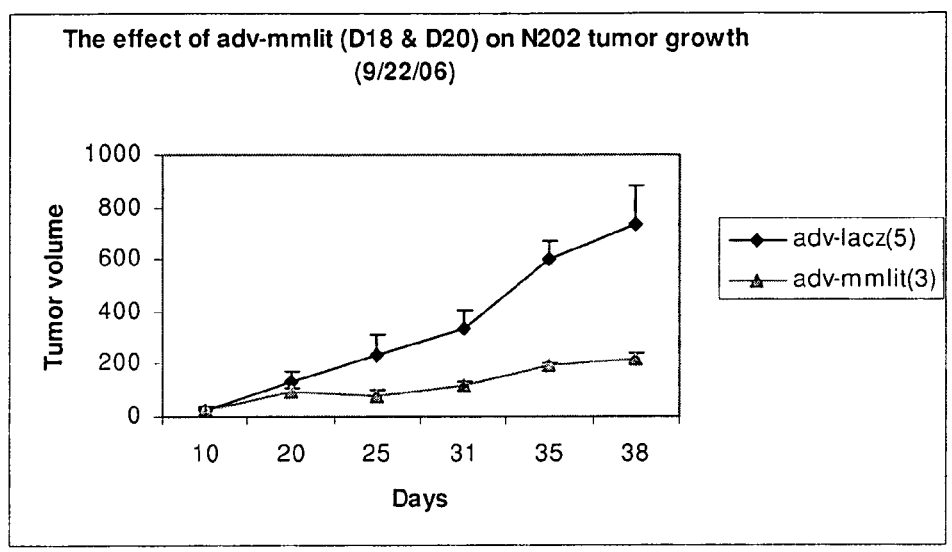
FIG. 2 demonstrates that Adv-mmlit inhibits neu+N202 tumor growth. About 8×10⁵ N202 1A cells were injected (i.c.). Intratumoral injections of about 2×10¹⁰ vp adv-lacz or adv-mmlit were performed at day 18 and day 20. The size of tumor was monitored twice a week.
Figure 3:
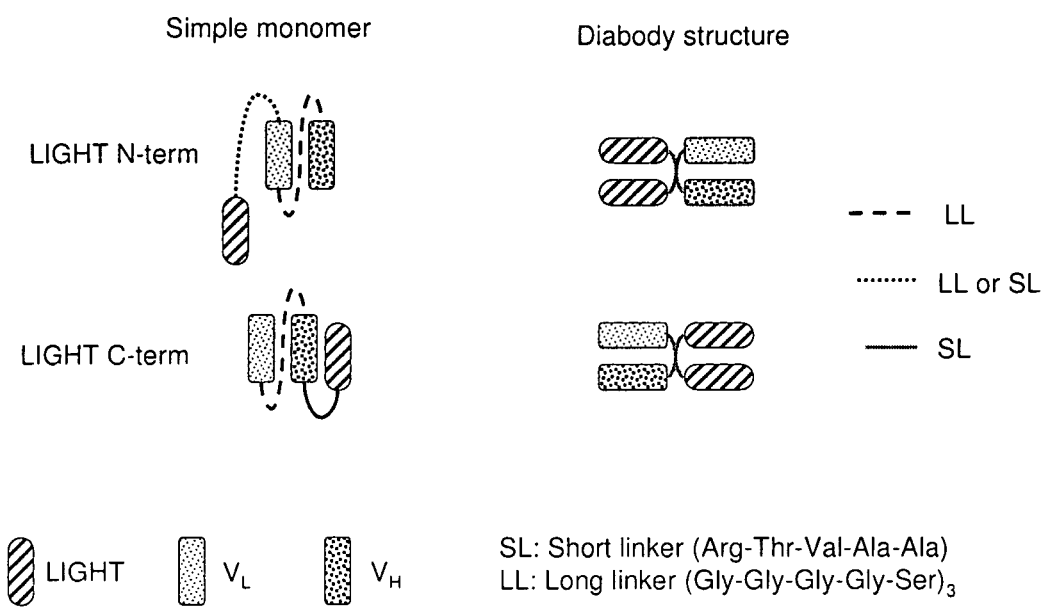
FIG. 3 shows the scFv-LIGHT fusion protein structure design.

For example, an extracellular domain of LIGHT molecule can be recombinantly expressed such that either the recombinant form does not have the proteolytic site all together or has one or more amino acid changes that renders the recombinant form protease digestion resistant (mutant LIGHT). In addition, the extracellular domain or a functional equivalent derivative of the extracellular domain of LIGHT can be linked to a tether or linker or spacer sequence to anchor the extracellular domain in the membrane of tumor cells. FIGS. 2-3 illustrate some aspects of an antibody-LIGHT fusion or conjugation.

The extracellular domain of LIGHT refers to a form of the LIGHT polypeptide which is essentially free of the transmembrane and cytoplasmic domains. The extracellular domain of LIGHT has less than 1% of such transmembrane and/or cytoplasmic domains and preferably, will have less than 0.5% of such domains. It is to be understood that any transmembrane domains identified for the LIGHT polypeptides are identified pursuant to criteria routinely employed in the art for identifying that type of hydrophobic domain. The exact boundaries of a transmembrane domain may vary but most likely by no more than about 2-5 amino acids at either end of the domain as initially identified herein. An extracellular domain of a LIGHT polypeptide may contain from about 5 or fewer amino acids on either side of the transmembrane domain/extracellular domain boundary as identified herein.

Suitable LIGHT protein, protein and peptide fragments thereof, include for example, amino acid positions 1-240 of LIGHT without one or more of the amino acids representing the proteolytic site EQLI (81-84) (SEQ ID NO: 1); amino acid positions 1-240 of LIGHT with one or more of the amino acids representing the proteolytic site EQLI (81-84) (SEQ ID NO: 1) is mutated or otherwise inactivate; 82-240 of LIGHT; 83-240 of LIGHT; 84-240 of LIGHT; 85-240 of LIGHT; 90-240 of LIGHT; 95-240 of LIGHT; 100-240 of LIGHT; 85-235 of LIGHT; 85-230 of LIGHT; 85-225 of LIGHT; 85-220 of LIGHT; 85-215 of LIGHT; 85-200 of LIGHT; LIGHT fragment without the intracellular and membrane domain; and any fragment that is about 100-150 amino acids in length of LIGHT that is resistant to protease digestion.

"Antibody-LIGHT" refer to an antibody or a fragment thereof specific against a tumor antigen, which is either fused or conjugated to a fragment of LIGHT protein that is sufficient to trigger an immune response against tumor cells and is capable of being stably present on a tumor cell surface by being resistant to protease digestion compared to a native LIGHT protein.

Figure 6:
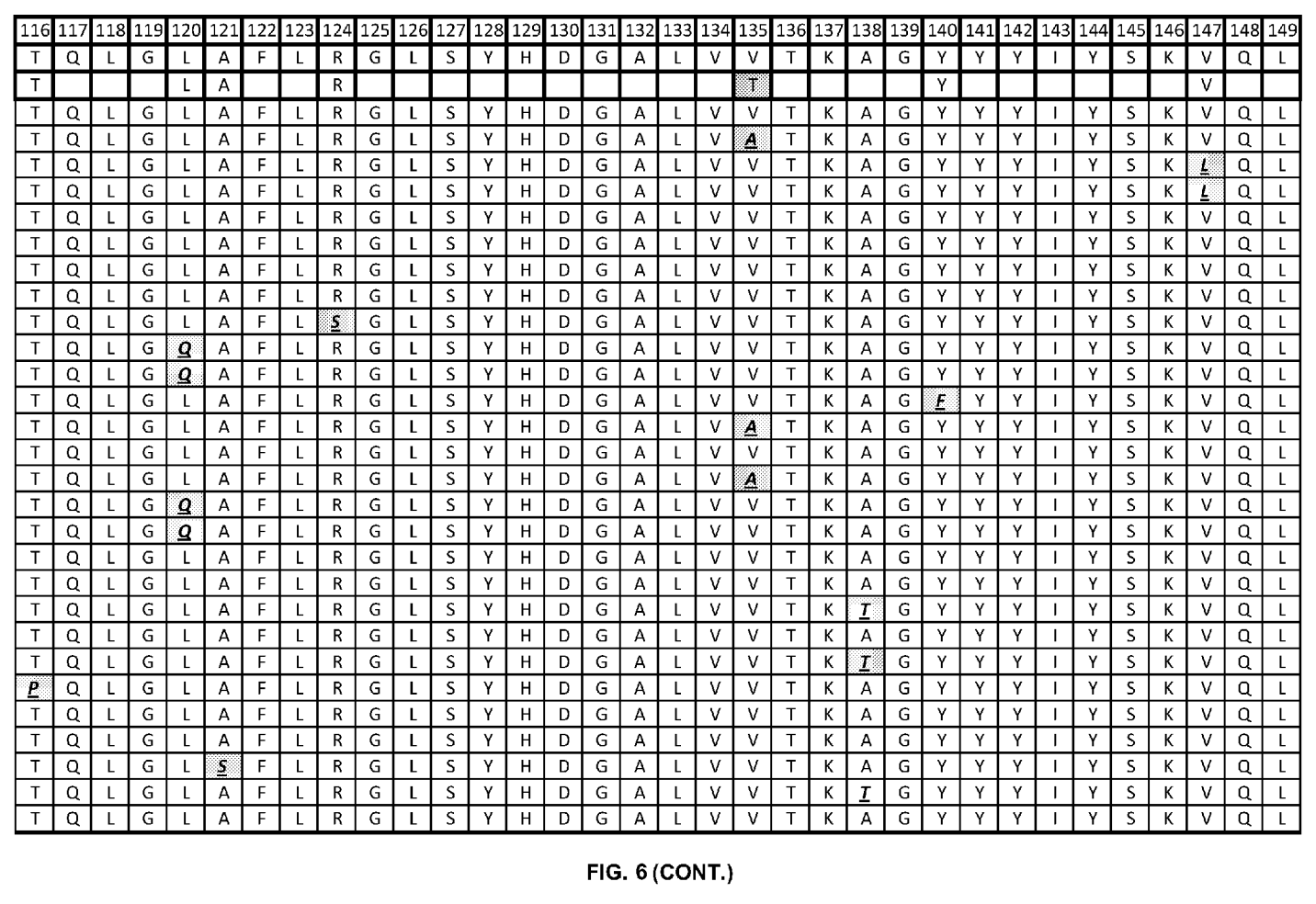
Figure 6:
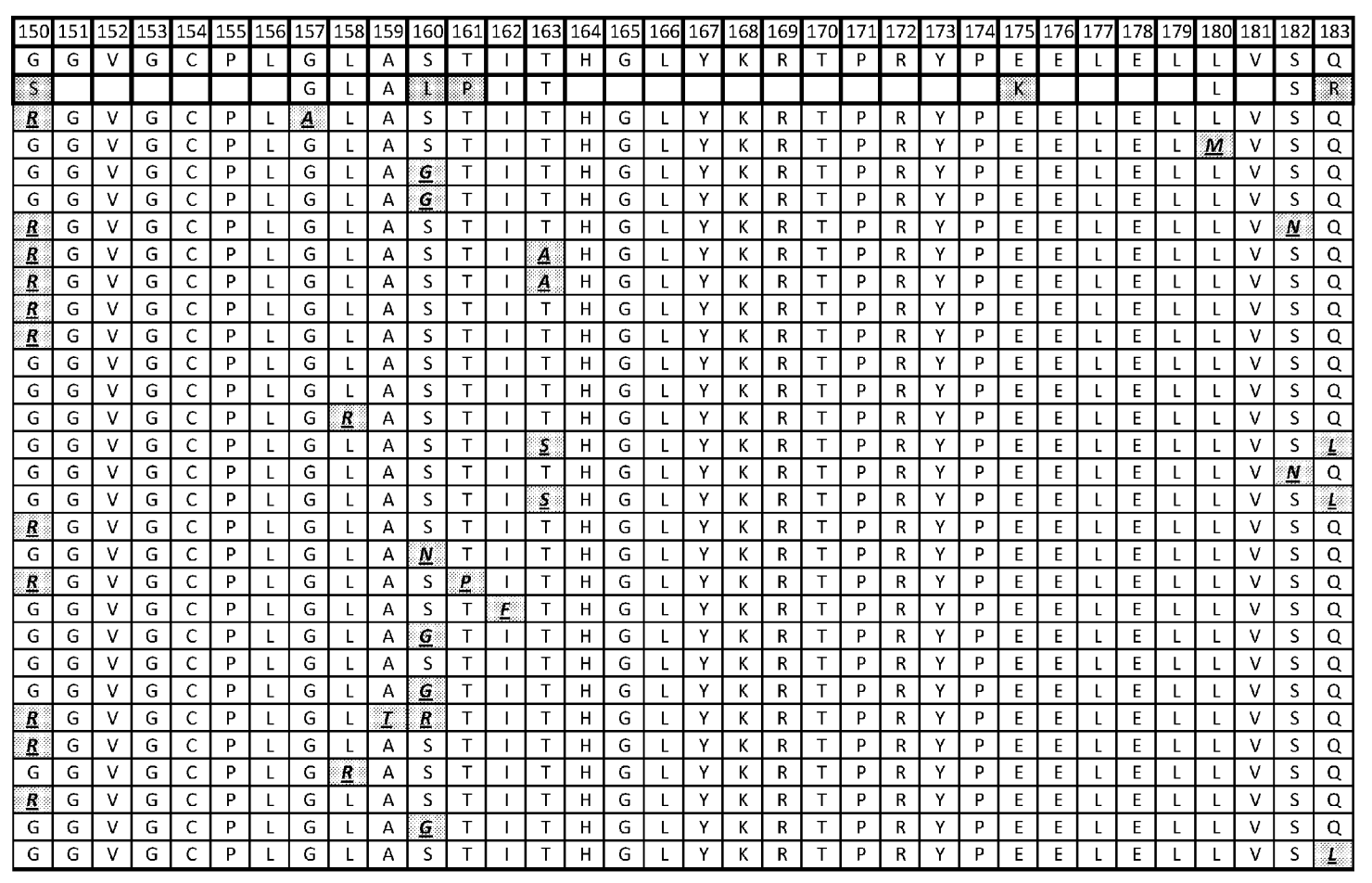
Figure 6:
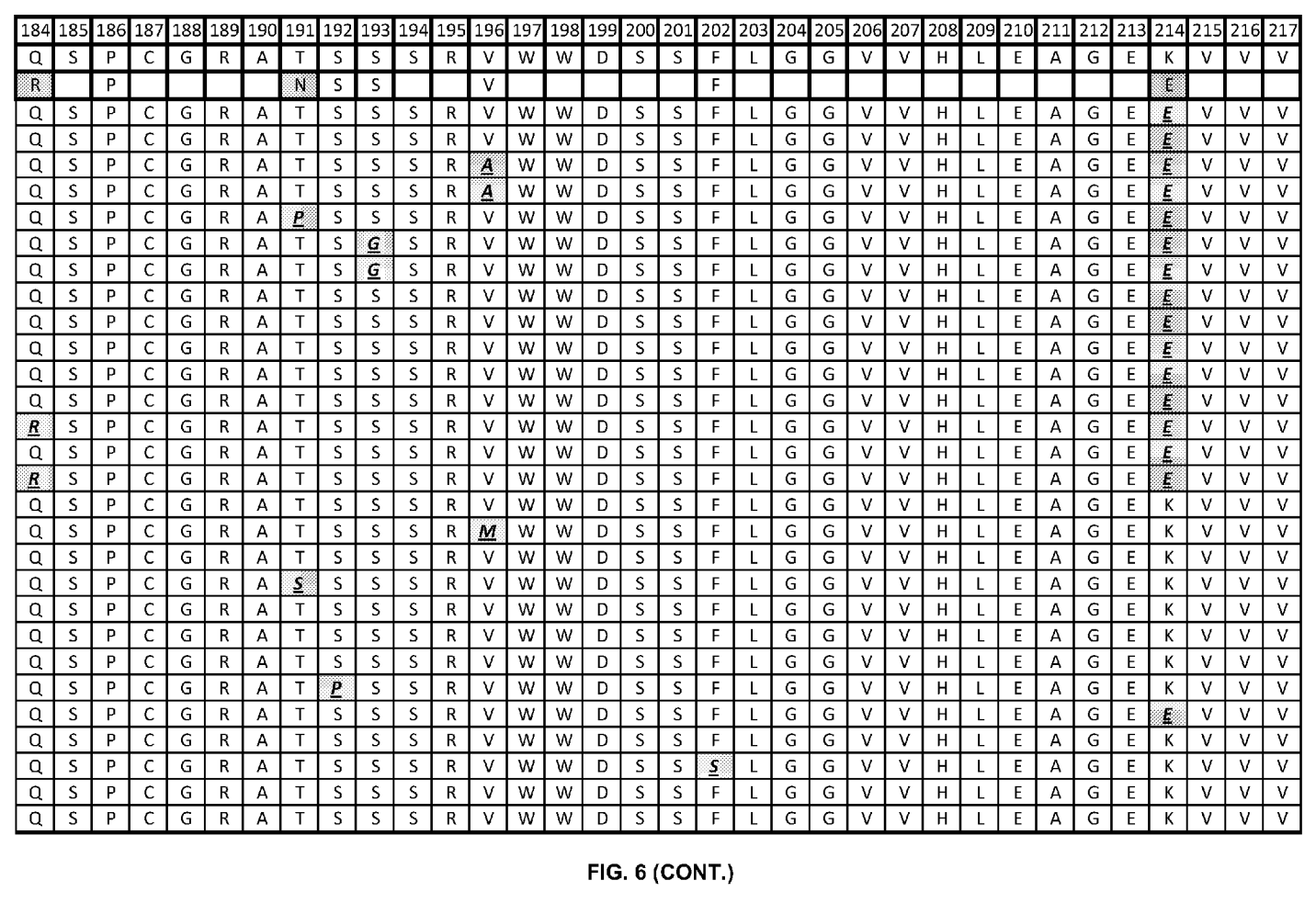

As used herein, the term "LIGHT" in an antibody-LIGHT couple refers to either an extracellular domain of LIGHT that does not contain a protease recognition sequence, or a mutant LIGHT wherein the protease site (EQLI) (SEQ ID NO: 1) is inactivated by entire deletion or a mutation at one or more amino acids that render the protease site insensitive or inactive or a truncated form of LIGHT that is resistant to protease digestion and capable of stimulating T-cells. LIGHT may also refer to a novel sequence in FIGS. 6 and 7.

"Mutant LIGHT" refers to a LIGHT protein or a LIGHT-derived peptide that is resistant to proteolytic cleavage, capable of being stably expressed in the surface of tumor cells, and exhibits increased activation of tumor specific T-cells, compared to normal or native LIGHT protein. The "mutant LIGHT" relates to a LIGHT protein or LIGHT protein-derived peptides or fragments that are resistant to protease digestion or otherwise are capable of being stably expressed on the surface of cells including tumor cells because of a mutation that renders the proteolytic site EQLI (SEQ ID NO: 1) inactive. There are several ways to generate mutant LIGHT. For example, the protease site (e.g., EQLI) (SEQ ID NO: 1) can be mutated either to remove the protease site in toto or to render the site resistant to protease digestion by changing (e.g., insertion, deletion, substitution) one or more amino acids at the protease site.

"Truncated LIGHT" protein refers to a LIGHT fragment that is not full length when compared to a native LIGHT, is resistant to protease digestion and is capable of stimulating T-cells against tumor cells. For example, the extracellular domain of LIGHT (about 85-240) is a suitable truncated LIGHT. Truncated LIGHT includes fragments/derivatives of LIGHT protein that are resistant to protease digestion thereby exhibiting the ability to be present on the cell surface for an extended period of time compared to native LIGHT protein.

To generate protease resistant LIGHT protein (e.g., mutant LIGHT) or fragments or LIGHT protein or LIGHT peptides with the protease site inactivated, for example, the amino acid glutamic acid (E), can be deleted or substituted within the protease recognition sequence EQLI (SEQ ID NO: 1). Similarly, the amino acid glutamine (Q) is deleted or substituted with another amino acid within the protease recognition sequence EQLI (SEQ ID NO: 1). Similarly, amino acid L or I can be deleted or substituted with other amino acids. Protease resistant amino acid analogs can also be used to generate synthetic LIGHT fragments that protease resistant. For example, using the incorporation of β-amino acids into peptides decreases proteolysis and can be used to substitute the protease sensitive site EQLI (SEQ ID NO: 1). Rational incorporation of β-amino acids within the protease site and near the protease site can be performed and the resulting mutants tested for protease resistance. A variety of techniques including site directed mutagenesis can be used to generate LIGHT fragments that are resistant to protease digestion.

The term "inactivated" means that the LIGHT protein or its fragments thereof is resistant to protease digestion in a tumor environment because the protease recognition site has been selectively silenced either by mutation in one or more amino acids or by deletion of EQLI (SEQ ID NO: 1) or by substitution of one or more amino acids with α- or β-amino acids or by any suitable way.

The term "resistant" means that the LIGHT protein or its fragments thereof is not sensitive to protease digestion in a tumor environment because the protease recognition site has been inactivated/mutated either by mutation in one or more amino acids or by deletion of EQLI (SEQ ID NO: 1) or by substitution of one or more amino acids with α- or β-amino acids or by any suitable way.

The term "tumor environment" refers to the presence and expression and activity of cellular proteases including extracellular proteases that may co-operatively influence matrix degradation and tumor cell invasion through proteolytic cascades, with individual proteases having distinct roles in tumor growth, invasion, migration, angiogenesis, metastasis and expansion of tumors.

"Ad-LIGHT" or "Ad-mutant LIGHT" refers to recombinant adenoviral vector system that contains mutant LIGHT encoding nucleic acids and is suitable for delivering the nucleic acid sequences to a tumor site or capable of infecting tumor cells. "Metastasis or metastases" refers to the process by which cancer spreads from the location at which the cancer initiated as a tumor to one or more distant locations in the body by migration of one or more cancerous cells. These terms also include micro-metastasis wherein the formation of tumors at distal locations corresponds to small aggregates of cancer cells that are visible microscopically. These terms also refer to the secondary cancerous growth resulting from the spread of the primary tumor from the original location.

"Reducing or controlling metastasis" refers to a reduction in the number of metastatic tumor sites as compared to a control.

"Adoptive transfer" refers to the transfer of T cells into recipients.

"Tumor site" means a location in vivo or ex vivo that contains or is suspected of containing tumor cells. Tumor site includes solid tumors and also the locations that are adjacent or immediately near a tumor growth.

"Tumor-specific" refers to antibody or any other ligand/receptor that shows preference to tumor cells over normal cells. For example, an antibody targeted to an antigen present on tumor cells is considered tumor-specific. A tumor-specific antibody may also bind to a normal cell if the target antigen is present, albeit to a lesser degree.

As used herein, the term "administration" refers to systemic and/or local administration. The term "systemic administration" refers to non-localized administration such that an administered substance may affect several organs or tissues throughout the body or such that an administered substance may traverse several organs or tissues throughout the body in reaching a target site. For example, administration into a subject's circulation may result in expression of a therapeutic product from an administered vector in more than one tissue or organ, or may result in expression of a therapeutic product from an administered vector at a specific site, e.g., due to natural tropism or operable linkage of tissue-specific promoter elements. One of skill in the art would understand that various forms of administration are encompassed by systemic administration, including those forms of administration encompassed by parenteral administration such as intravenous, intramuscular, intraperitoneal, and subcutaneous administration. In some embodiments, systemic administration can be used to elicit a systemic effect associated with treatment of a local or systemic disease or condition. A systemic effect may be desirable for a local disease or condition, for example, to prevent spread of said disease or condition. The term "local administration" refers to administration at or near a specific site. One of skill in the art would understand that various forms of administration are encompassed by local administration, such as direct injection into or near a specific site. In some embodiments, local administration is associated with treatment of a disease or condition where a local effect is desired (e.g. administration to the lung for the treatment of lung cancer). A local effect may be desired in association with either local or systemic diseases or conditions. A local effect may be desired in association with a systemic disease or condition to treat a local aspect of a systemic disease or condition.

An "effective amount" of LIGHT, LIGHT polypeptide or peptide, or a fragment thereof, LIGHT fusion products, or LIGHT conjugates, and the like, refers to an amount sufficient to carry out a specifically stated purpose. An "effective amount" may be determined empirically and in a routine manner, in relation to the stated purpose. For example, a suitable purpose for an antibody-LIGHT construct is reducing tumor size or growth and/or reduce metastases.

The term "therapeutically effective amount" refers to an amount of LIGHT, LIGHT polypeptide or peptide or a fragment thereof, LIGHT fusion products or conjugates, effective to treat a specific disease or disorder in a subject or mammal. In the case of cancer, the therapeutically effective amount of the compositions disclosed herein may reduce the number of cancer cells; reduce the tumor size; inhibit (i.e., slow and/or stop) cancer cell infiltration into peripheral organs; inhibit (i.e., slow and/or stop) tumor metastasis; inhibit tumor growth; and/or relieve one or more of the symptoms associated with the cancer.

The term "antibody" covers, for example, monoclonal antibodies, polyclonal antibodies, single chain antibodies, fragments of antibodies (see below) as long as they exhibit the desired biological or immunological activity. The term "immunoglobulin" (Ig) is used interchangeable with antibody herein. The antibodies may specifically target a tumor antigen, e.g., surface tumor antigen such as for example Her2/neu and CD20.

An "isolated antibody" is one which has been identified and separated and/or recovered from a component of its natural environment. The antibody is purified to greater than 95% by weight of antibody as determined by the Lowry method, and more than 99% by weight.

The term "monoclonal antibody" as used herein refers to an antibody obtained from a population of substantially homogeneous antibodies, i.e., the individual antibodies of the population are identical except for possible naturally occurring mutations that may be present in minor amounts. Monoclonal antibodies are highly specific, being directed against a single antigenic site or an epitope. For example, the monoclonal antibodies may be prepared by the hybridoma methodology first described by Kohler et al., Nature, 256: 495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate, and human constant region sequences.

"Antibody fragments" include a portion of an intact antibody, for example the antigen binding or variable region of the intact antibody. Examples of antibody fragments include Fab, Fab$^1$, F(ab$^1$)$_2$, single chain F$_v$ and F$_v$ fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may include residues that are not found in the recipient antibody or in the donor antibody. These modifications are made to further refine antibody performance. In general, the humanized antibody includes substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also includes at least a portion of an immunoglobulin constant region (Fc), typically that of a human immunoglobulin.

The terms "cancer" and "cancerous" refer to or describe the physiological condition in mammals that is typically characterized by unregulated cell growth. Examples of cancer include carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

Suitable surface tumor antigens that can be targeted using a antibody-LIGHT fusion or conjugate includes epidermal growth factor receptor family (EGFR) including HER1, HER2, HER4, and HER8 (Nam, N. H., & Parang, K. (2003), Current targets for anti-cancer drug discovery. Current Drug Targets, 4(2), 159-179), STEAP (six-transmembrane epithelial antigen of the prostate; Hubert et al., STEAP: a prostate-specific cell-surface antigen highly expressed in human prostate tumors, Proc Natl Acad Sci USA. 1999; 96(25): 14523-8.), CD55 (Hsu et al., Generation and characterization of monoclonal antibodies directed against the surface antigens of cervical cancer cells, Hybrid Hybridomics. 2004; 23(2):121-5.). Other suitable antibodies include Rituximab (Rituxan™, a chimeric anti-CD20 antibody), Campath-1H (anti-CD52 antibody), and any cancer specific cell-surface antigens. The following is an exemplary list of approved monoclonal antibody drugs against specific cancer types that are suitable for use with LIGHT protein: Alemtuzumab (Campath™) for chronic lymphocytic leukemia; Bevacizumab (Avastin™) for colon cancer and Lung cancer; Cetuximab (Erbitux™) for colon cancer and head and neck cancer; Gemtuzumab (Mylotarg™) for Acute myelogenous leukemia; Ibritumomab (Zevalin™) for non-Hodgkin's lymphoma; Panitumumab (Vectibix™) for colon cancer; Rituximab (Rituxan™) for Non-Hodgkin's lymphoma; Tositumomab (Bexxar™) for non-Hodgkin's lymphoma; and Trastuzumab (Herceptin™) for breast cancer.

EXAMPLES

The following examples are for illustrative purposes only and are not intended to limit the scope of the disclosure.

Example 1

Coupling or Conjugating Light to a Tumor Targeting Agent

To enable delivery of a mutant LIGHT delivery system or an equivalent delivery system, mutant LIGHT can be coupled or conjugated to a tumor targeting agent such as a tumor specific antibody. For example, a tumor specific antibody conjugated to LIGHT or mutant LIGHT can be used to selectively deliver the fusion protein to the tumor site. In addition, a tumor specific antibody can be designed to be coupled with a viral delivery system or a liposome vehicle delivery system. The delivery vehicle expressing the mutant LIGHT and harboring the tumor targeting agent will first target the specific tumor cell and then transform the tumor cell to express mutant LIGHT on the surface of the cell. This targeted mutant LIGHT expression on the surface of the tumor cells will induce chemokines on stromal cells surrounding the tumor to attract and initiate priming of T-cells. Such treatments are suitable for all tumors, including solid tumors. 4T1, MC38, B16, and mastocytoma were treated with Ad-LIGHT and showed a reduction of primary and/or secondary tumors. Therefore, antibody-LIGHT can be used to target various tumors, especially metastases that form as a result of cells of the primary tumor migrating to distant sites. For example, through systemic injection, anti-her2/neu antibody with LIGHT can carry LIGHT to metastatic tumor that expresses her2/neu and then can generate a local immune response to clear tumor. Therefore, the fusion protein can be delivered through any systemic and local route and the fusion protein will be more localized to tumors due to the specificity of antibody or another agent to tumor antigens.

Example 2

Functional Activities of a LIGHT Conjugated Antibody

The ability of antibody-LIGHT to bind to the receptors of LIGHT, LTβR and HVEM, is determined by flow cytometry with LTβR-Ig and HVEM-Ig, respectively. The functional activity of antibody-LIGHT is tested first in vitro for its ability to costimulate T cells in the presence of suboptimal doses of plate-bound anti-CD3. The functionality of antibody-LIGHT seems comparable with that of anti-CD28.

To test whether Antibody-LIGHT fusion protein inhibits tumor growth in vivo, mice are injected s.c. with $5 \times 10^4$ tumor cells for ten days and then treated with 10 µg of the fusion protein. The inhibition of tumor growth is demonstrated with a small dose of fusion protein, i.e. 10 µg, which allows strong immunity against tumor.

This example demonstrates the ability of antibody-LIGHT to bind to the receptors of LIGHT, LTβR and HVEM by flow cytometry with LTβR-Ig and HVEM-Ig, respectively, and that a tumor specific antibody coupled with LIGHT stimulates immunity to reduce tumor growth.

Example 3

Combination Treatment of Antibody-LIGHT Couple and Local Delivery of Adenovirus Expressing LIGHT An important utility of an antibody-LIGHT fusion protein or conjugate is that such targeting reagents may be very potent to clear small numbers of metastastic tumor cells or residual cancer cells that do not effectively stimulate the immune system. A combination therapy that includes antibody-LIGHT and adenovirus expressing LIGHT, or Ad-LIGHT, are tested.

Tumor cells are inoculated at two sites, one with $10^6$ and the other side with $1 \times 10^4$. Two weeks later, the larger tumor ($10^6$) is treated with Ad-LIGHT and surgically removed two weeks after treatment. Mice are treated systemically with Antibody-LIGHT at doses described herein. This model determines whether Antibody-LIGHT in combination with local delivery of Ad-LIGHT to primary tumor is a potent reagent for treating distal tumors. 2C T cells, which are readily identified by the clonotypic antibody (1B2), can be adoptively transferred to the tumor bearing mice as a model for tumor antigen-specific $CD8^+$ T cells. The trafficking, proliferation, and activation of adoptively transferred 2C T cells is monitored and compared with different therapeutic strategies.

Two clinically relevant delivery systems, Ad-LIGHT and Antibody-LIGHT, are expected to effectively target LIGHT to the tumor tissue and subsequently destroy not only the primary tumors but also distal metastases. The sustained expression of LIGHT long enough to create a LIGHT-mediated lymphoid-like structure induces the desired antitumor $CD8^+$ T cell responses.

Example 4

Anti-Her2/neu Antibody-LIGHT Therapy for Breast Cancer

One fifth of breast cancer and colon cancer patients express Her2/neu. Generally, antibody to Her2 slows down the growth of these tumors but does not eradicate them. Anti-Her2/neu antibody coupled with LIGHT targets LIGHT to the site of metastatic tumors. The anti-Her2/neu antibody slows down the growth of tumor and induces apoptosis, which allows the coupled LIGHT to induce LIGHT-mediated recruiting and activating of T cells to occur inside tumor. Additionally, LIGHT also recruits FcR+ cells to enhance the therapeutic effect of anti-neu antibody. In an experimental model, doses as low as 10 µg of a tumor antibody linked with LIGHT slowed down the growth of tumor in mice. Other lower or higher doses are contemplated. Anti-Her2/neu antibody-LIGHT is a novel treatment for breast cancer metastases. FIG. 2 shows that Adv-mmlit inhibits neu+N202 tumor growth.

Example 5

Use of Chemotherapy Drugs in Combination with Antibody-LIGHT Fusion or Conjugates A tumor-specific antibody-LIGHT fusion protein or conjugate is further coupled with an anti-tumor agent such as for example, doxorubicin, paclitaxel, docetaxel, cisplatin, methotrexate, cyclophosphamide, 5-fluoro uridine, Leucovorin, Irinotecan (CAMPTOSAR™ or CPT-11 or Camptothecin-11 or Campto), Carboplatin, fluorouracil carboplatin, edatrexate, gemcitabine, or vinorelbine or a combination thereof. These drugs can either be administered separately or co-administered by conjugation or coupling with the Antibody-LIGHT fusion protein or conjugate.

This combination therapy may also be co-administered with gene therapy whereby a nucleic acid capable of expressing a protease resistant LIGHT is delivered inside a tumor. Adeno-viral vectors harboring LIGHT nucleic acid sequences, or Ad-LIGHT, are suitable.

Example 6

Synergistic Suppression of Tumors by Anti-Her2 Antibody and Ad-LIGHT Treatment

Figure 4:
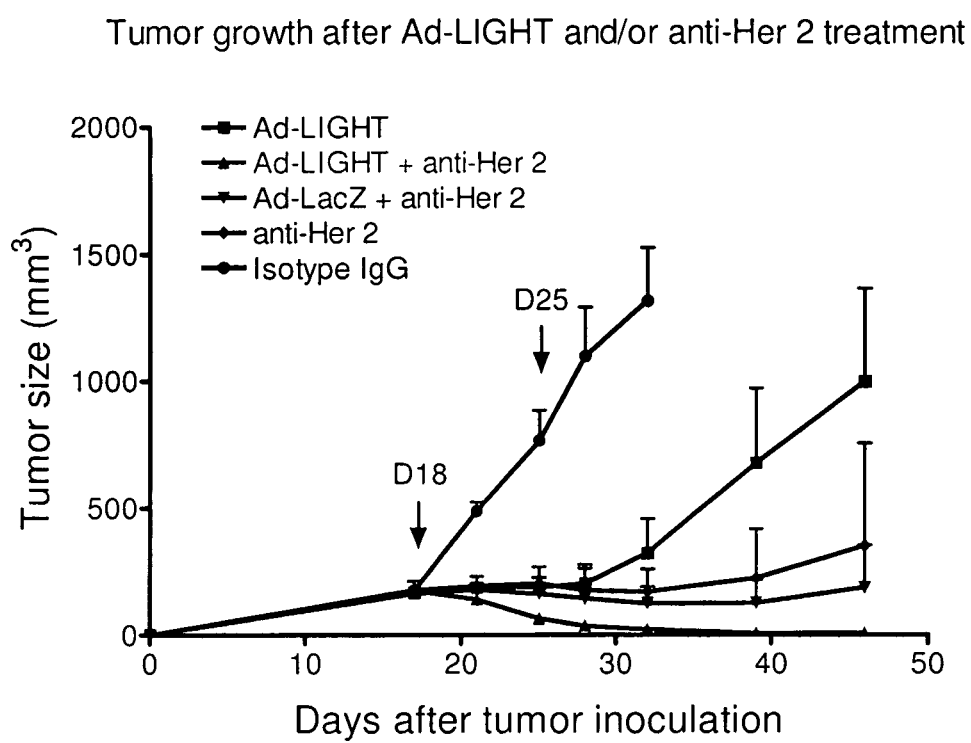
FIG. 4 shows suppression of tumor growth after anti-Her2 and Ad-LIGHT treatment that 10⁶ TUBO tumor cells were inoculated to BABL/c mice s.c. 10¹⁰ VP of Ad-LIGHT or Ad-LacZ was injected intratumorally at Day 18 after tumor inoculation. 50 μg anti-Her 2 antibody or isotype IgG was injected i.p. at Day 18 and 25 after tumor inoculation. Tumor growth was monitored at indicated time points. All of the treated groups have significant difference compared with isotype IgG group after Day 21. Ad-LIGHT and anti-Her2 combination treatment group has significant synergistic difference compared with either Ad-LIGHT alone or anti-Her2 alone group after Day 25. Statistic analysis was performed with two-tail student's test. Data shown were means+SEM. p<0.05 was regarded as significant difference.
Figure 5:
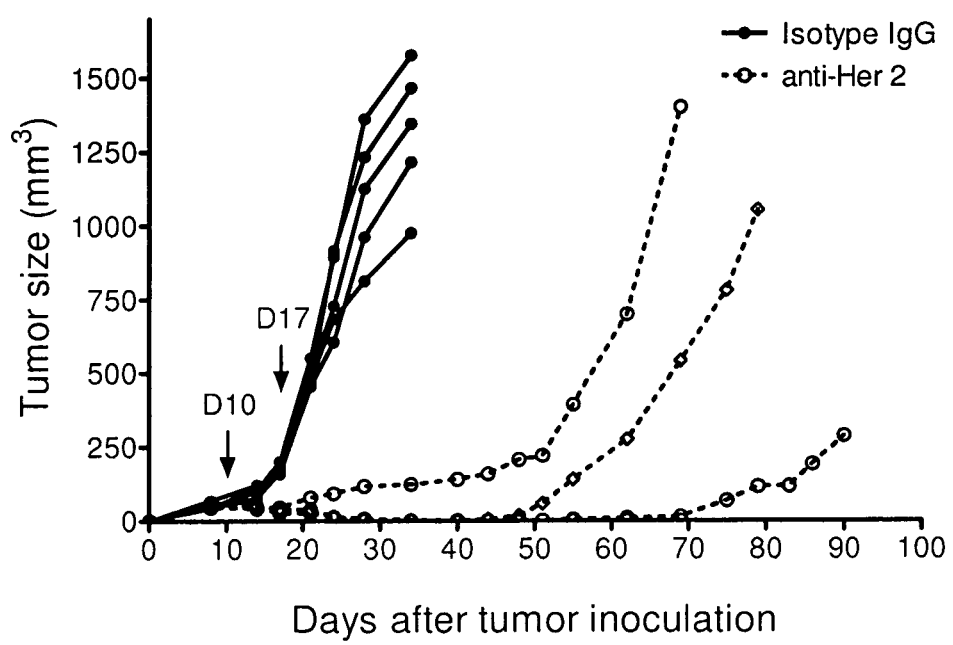
FIG. 5 shows suppression of tumor growth after anti-Her2 treatment. 10⁶ TUBO tumor cells were inoculated to BALB/c mice s.c. 100 μg anti-Her 2 antibody or isotype IgG was injected i.p. at Day 10 and 17 after tumor inoculation. Tumor growth was monitored at indicated time points. Tumor regrew in three out of five mice treated with anti-Her 2.
Figure 8:
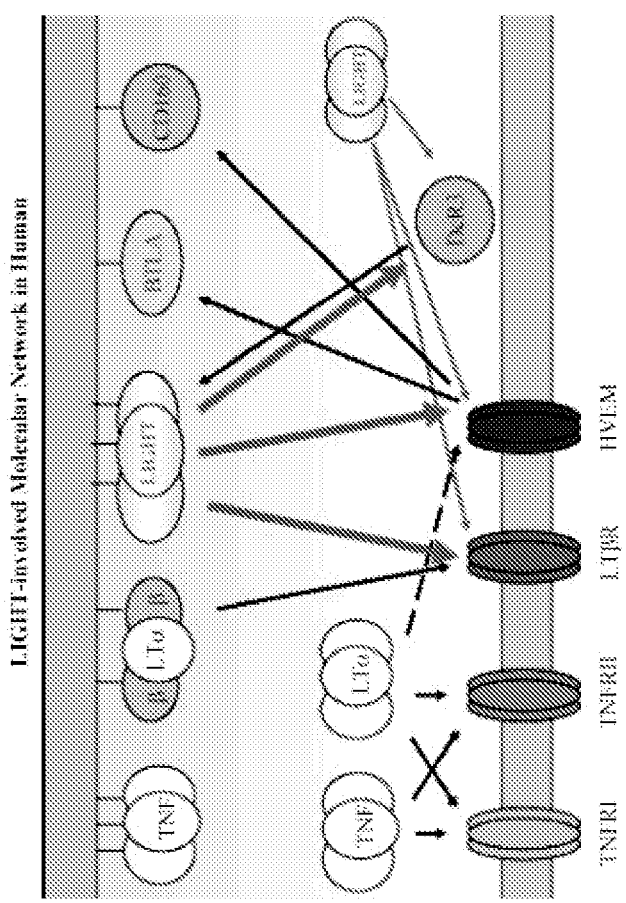
FIG. 8 illustrates the LIGHT network in humans. LIGHT (TNFSF14) is expressed as a trimer on lymphoid tissue, immature DCs and activated T cells, and binds LTbR and HVEM on target cells. LIGHT also binds soluble Decoy Receptor 3 (DcR3) in humans, which is secreted by a number of cancers, including gastrointestinal, bone, lung, and soft tissue tumors. The interplay of TNF family members as shown controls immune regulation.
Figure 9:
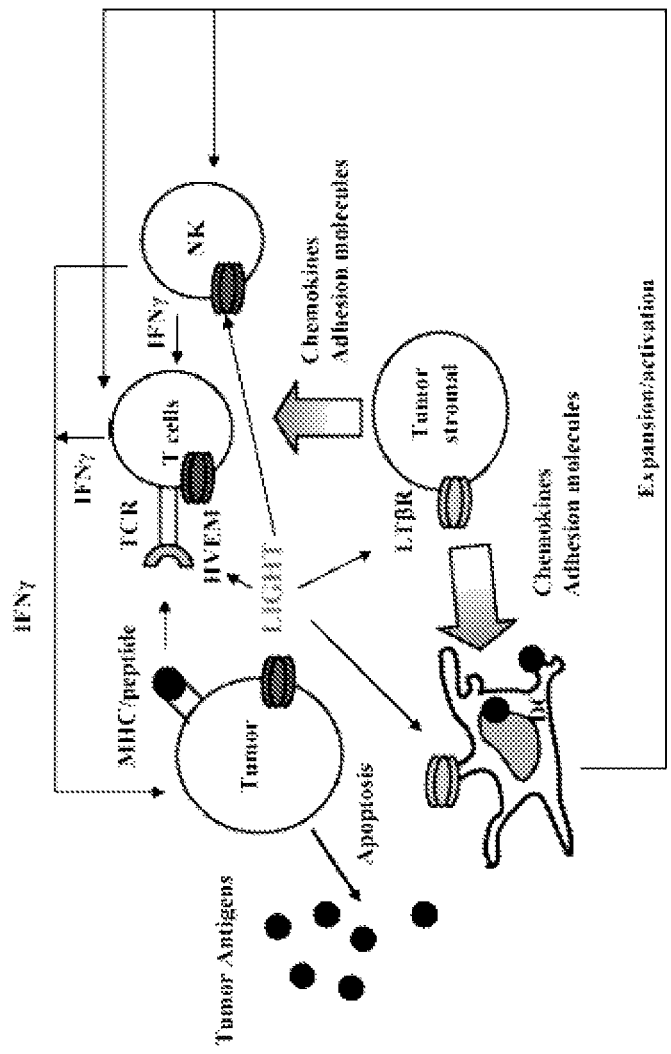
FIG. 9 illustrates the 3-pronged activity of LIGHT. LIGHT binds both LTβR and HVEM for immune modulation, and interactions with LTβR increase chemokines and adhesion molecules and attract T cells. LIGHT activates T cells and NK cells through HVEM for increased immune function and tumor immunity. Finally, LIGHT can direct apoptosis of LTβR or HVEM expressing tumors.
Figure 10:
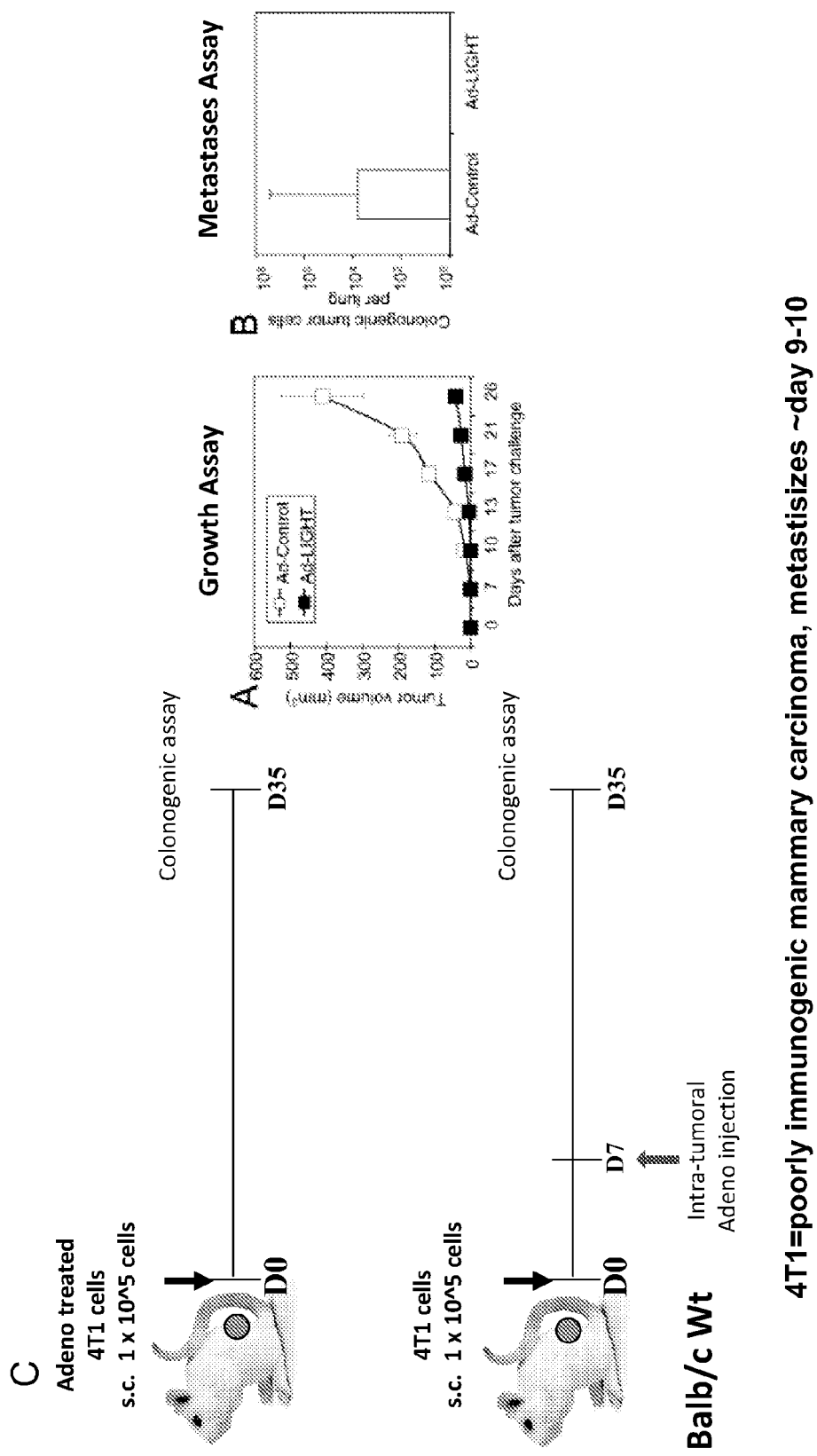
FIG. 10 shows that expression of LIGHT near mammalian tumors in vivo controls metastases. (C) 4T1, a normally poorly immunogenic mammary carcinoma cell line, mimics breast cancer when injected into the mammary fat pad of mice. It can metastasize to various organs, including lungs. In vitro-cultured 4T1 mammary carcinoma ($1 \times 10^5$ cells) were infected with Ad-LIGHT or Adcontrol ($2 \times 10^8$ PFU/ml) for 24 h and then $1 \times 10^8$ cells were injected s.c. into the flank of BALB/c mice. Tumor growth was monitored (A) until mice were sacrificed on day 35 posttumor inoculation for analysis of (B) lung metastases with colonogenic assay.
Figure 11:
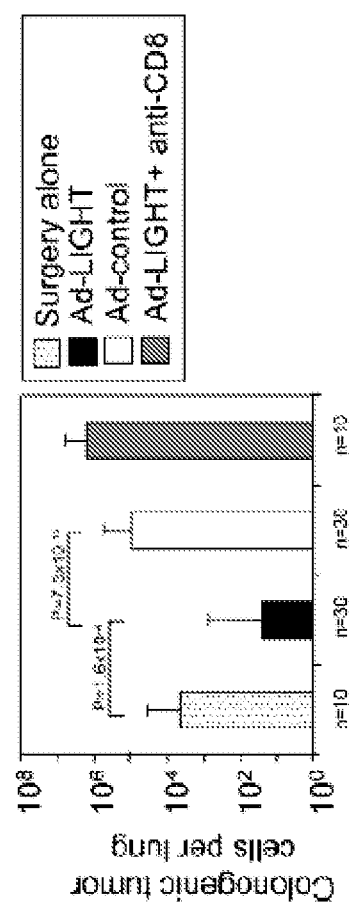
FIG. 11 shows that Ad-LIGHT treatment eradicates established metastases. A, 4T1 mammary carcinoma cells injected s.c. into the flank of BALB/c mice were treated intratumorally with $1 \times 10^9$ PFU Ad-LIGHT (black) or Adcontrol (white) on days 14 and 17 posttumor inoculation. One group of mice was treated with surgery alone on day 14 posttumor challenge (dotted). Other 4T1 tumor-bearing mice were treated with Ad-LIGHT in the same way, with the addition of CD8 depletion by anti-CD8 Ab (YTS. 169.4.2), starting day 14 after primary tumor inoculation (gray). Anti-CD8 Ab was given to mice i.p., 125 µg/mouse once every week until the mice were sacrificed for analysis. More than 90% of CD8+ T cells were depleted by this regimen, as confirmed by FACS staining of peripheral blood. Except for the mice that were treated with surgery alone, the primary tumors (about 150 mm3) on other mice were surgically resected on day 24 and mice were sacrificed for analysis of lung metastases with colonogenic assay on day 35. Data are a pool of multiple independent experiments.

The synergy of anti-neu antibody with LIGHT. TUBO. TUBO is a cloned cell line generated from a spontaneous mammary gland tumor from a BALB-neuT mouse and highly expresses HER-2 protein on the cell membrane. This tumor line is sensitive to anti-neu antibody treatment in vivo and in vitro. However, when a tumor is well established, the effect of either antibody or LIGHT alone is diminished. After anti-neu antibody is discontinued, TUBO cells can recover within 3-4 weeks. To determine whether there is a synergy between the two, TUBO cells were established for 18 days and then treated with both ad-LIGHT and anti-neu antibody once a week for three weeks. Impressively, no tumor can be detected in this combination while tumor grows progressively with single treatment of either (FIGS. 4-5). All five mice in each group have tumors, except for those administered the combinational treatment.

Thus combining LIGHT-mediated therapy, e.g., by Ad-LIGHT expressing vector or by another stable LIGHT presentation to tumor cells with any other anticancer therapy provides a synergistic tumor suppression therapeutics.

Example 7

Generation of Antibody-LIGHT Fusion Proteins

To express sc-Fv-LIGHT, scFV-58LIGHT (LIGHT fragment with amino acid positions 58-240) and scFV-85LIGHT (LIGHT fragment with amino acid positions 85-240, bypassing protease site of 81-84) were constructed. Flag tap was attached to the LIGHT fragment following western blotting since anti-Flag antibody is very specific and sensitive. Such plasmids were transfected into a 293 cell line. The cells were harvested one week later and lysates were prepared and blotted with anti-flag antibody. Visualization of the anti-Flag western blot shows that the expression of scFv-85LIGHT expression is higher than scFv-58LIGHT.

This demonstrates that the antibody-LIGHT fusion construct generates fusion proteins and that resulting fusion proteins can be isolated, purified and used to demonstrate that antibody-LIGHT fusion proteins specifically targets tumor cells and stimulates production of T-cells against the tumor cells. Similar fusion proteins of LIGHT can be made with any other antibody that is directed against a tumor cell surface antigen and preferably that targets a tumor-specific cell surface antigen.

Example 8

Antibody-LIGHT Fusion Constructs

Figure 12:
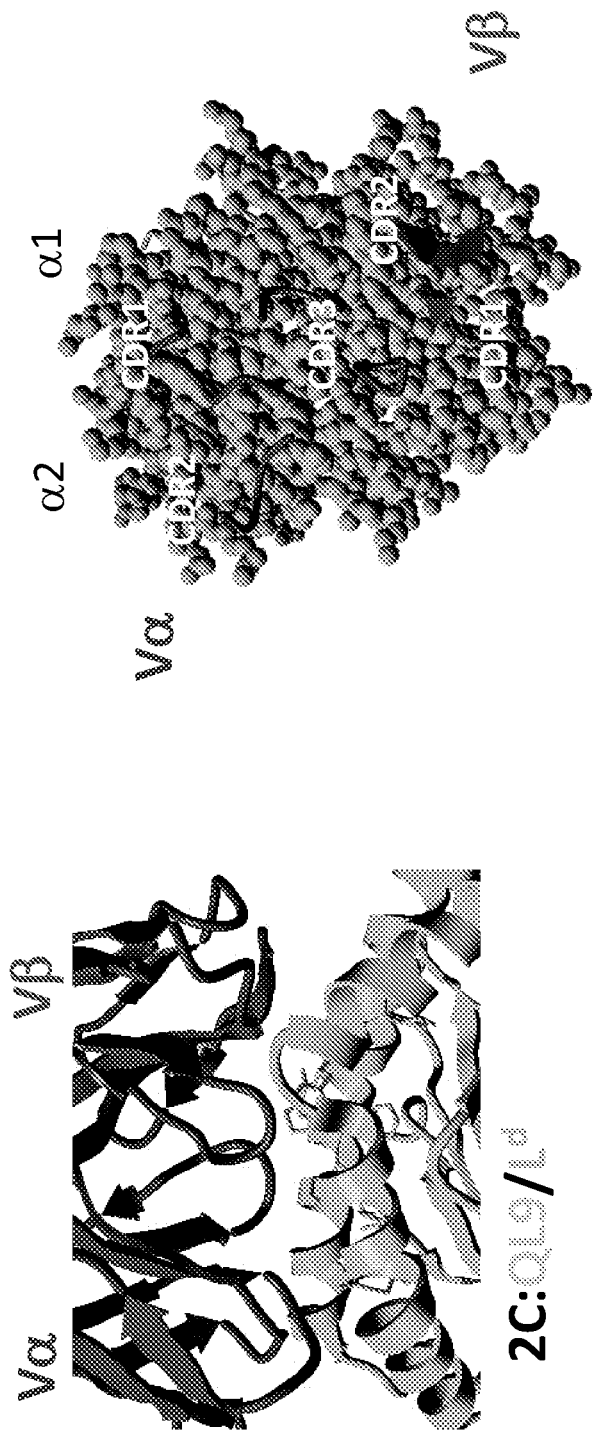
FIG. 12 shows models of a T-cell receptor with the CDR1, CDR2, and CDR3 regions highlighted.
Figure 13:
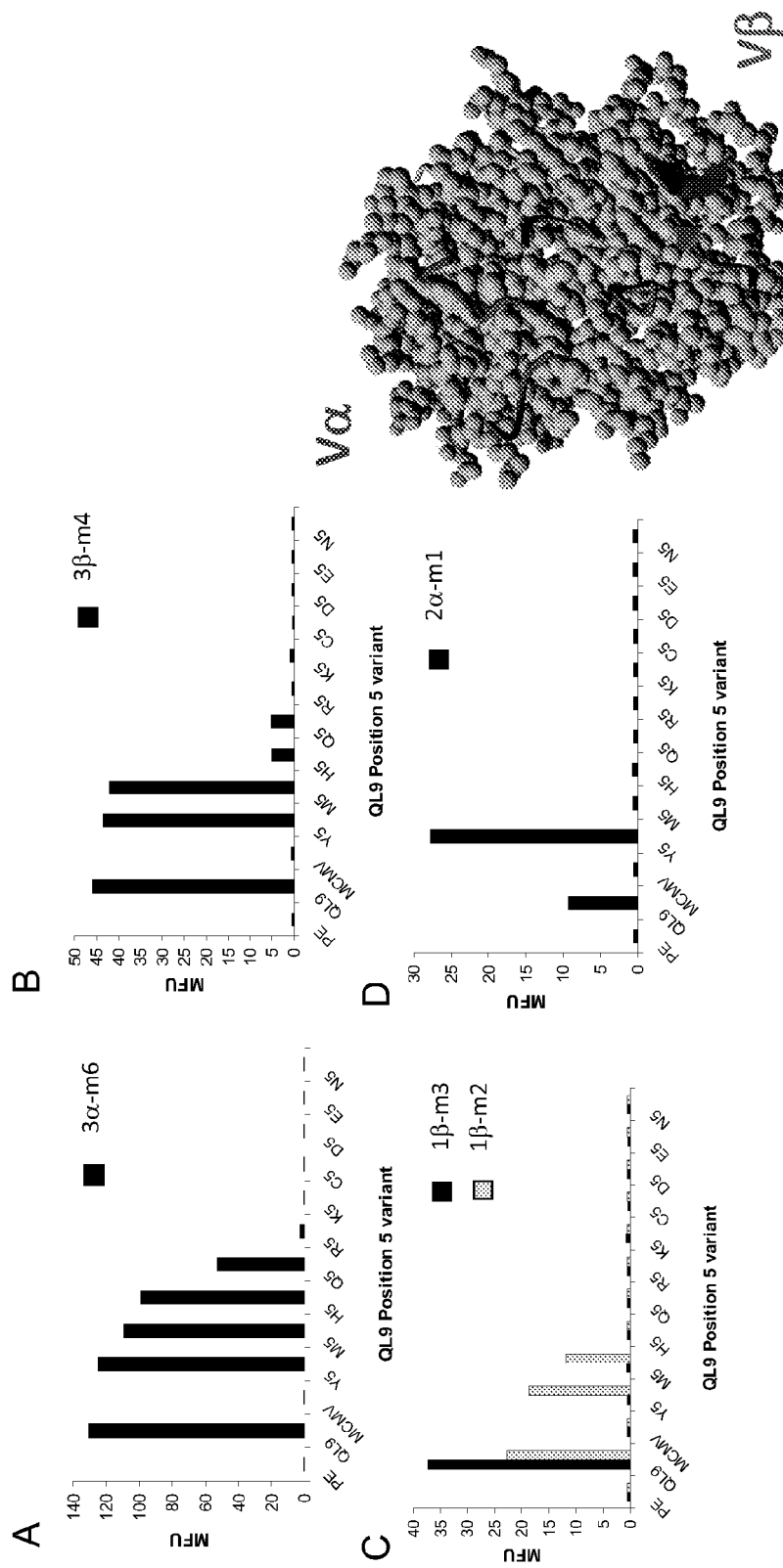
FIG. 13 shows peptide specificity of CDR mutants, QL9/Ld binding and peptide-Ld specificity of various CDR mutants. Peptide selectivity of yeast-displayed 2C mutants selected on QL9/Ld. Mutants in (A) CDR3a, (B) CDR3b, (C) CDR1b, and (D) CDR2a were assayed with (0.4 mM) the indicated peptide/Ld/Ig dimer, or the secondary reagent (PE) alone. MCMV, YPHFMPTNL (SEQ ID NO: 34); QL9, QLSPFPFDL (SEQ ID NO: 35); QL9 variants contained single amino acid substitutions at position 5 (wild-type, F). Yeast cells were assayed by flow cytometry for binding of the pep-Ld complexes (MFU, mean fluorescence units).

To generate a tumor targeting antibody-LIGHT immunocytokine, the following steps were taken:
 a. LIGHT was engineered for increased stability/affinity;
 b. a scFV(neu)-LIGHT fusion protein was generated for production; and
 c. the scFV(neu)-LIGHT fusion protein was tested in vitro and in vivo
To engineer LIGHT:
 human LIGHT was used as a platform for the engineering.
 Human LIGHT seems more stable (YD and prior expression) than mouse LIGHT; and
 Human LIGHT cross-reacts (weakly) to murine receptors.
 Criteria for engineering of LIGHT
 a. Equivalent binding to murine and human LTbR and HVEM, and if possible, decreased to DcR3; and
 b. Improved expression/stability to ease production.
Proteins that were engineered using yeast-display include the following: 2C
T-cell receptor, Ly49C—c-type lectin NKR, 2B4 (CD244)—Ig-like NKR, CD48—Ig-like NKR and murine and human KLRG1—c-type lectin NKR. Higher-affinity clones in other CDRs show excellent peptide specificity. (FIGS. 12-13.)

Figure 14:
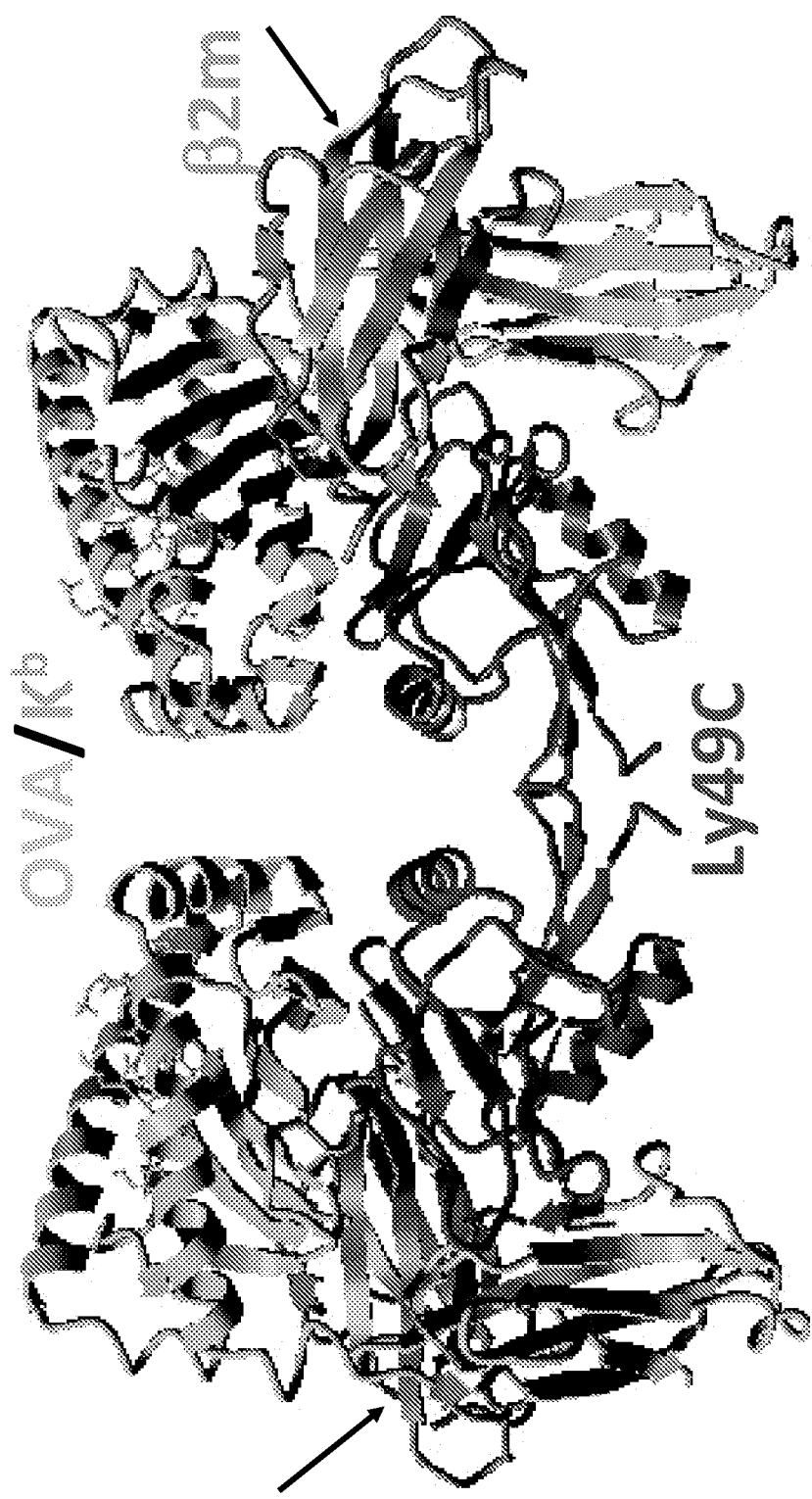
FIG. 14 is a ribbon diagram of the mutant Ly49C-H-2 Kb complex, in which the crystallographic Ly49C dimer (arrow) crosslinks two MHC class I molecules.
Figure 15:
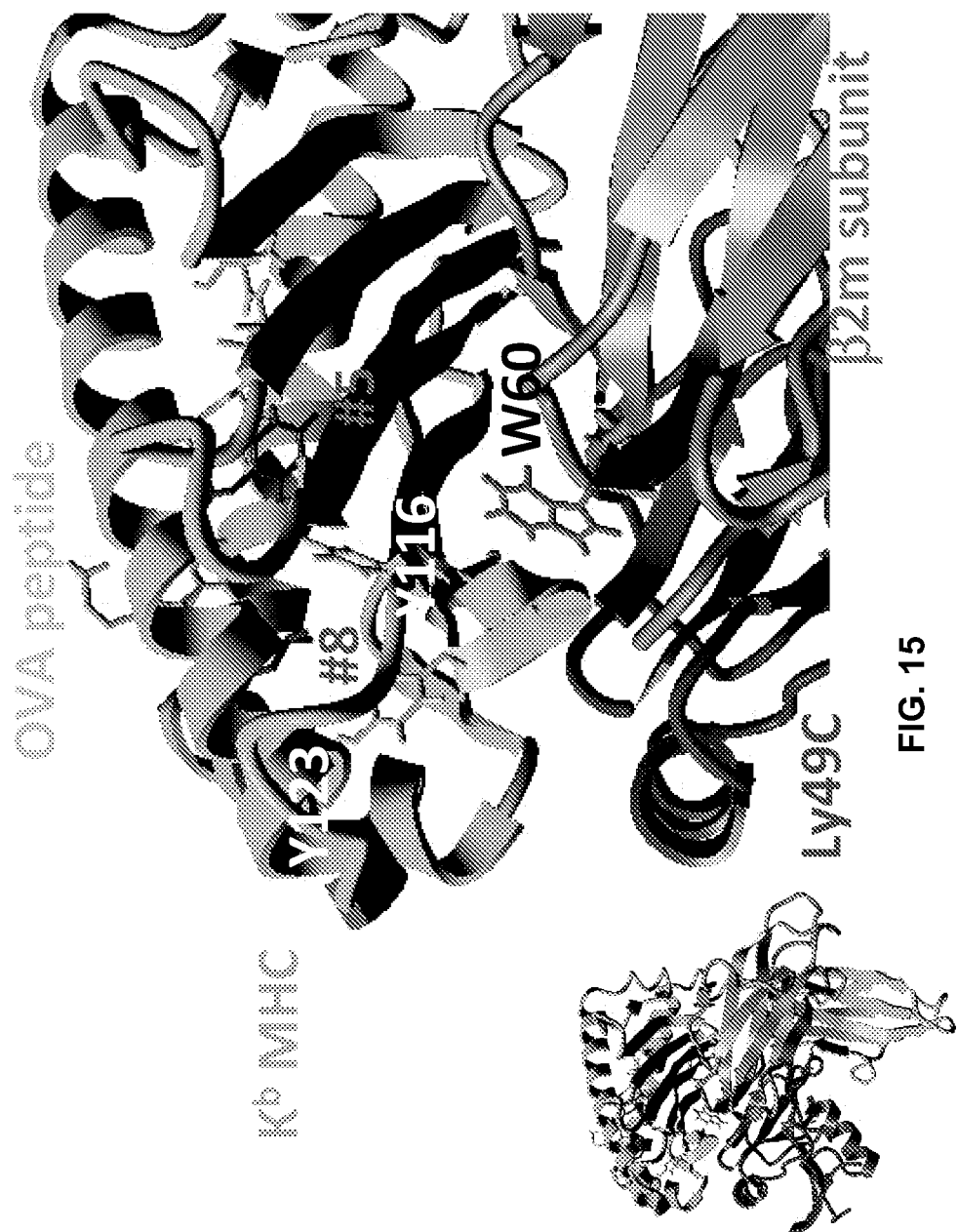
FIG. 15 illustrates the "domino" effect of peptides on pepMHC binding and specificity. There is a network of hydrogen bonding interactions that cascade to the Ly49C contact region. Different peptides may alter MHC conformation and change Ly49C binding.

Engineering of LY49C allowed high resolution crystal structure of LY49C-OVA/$K^b$ complex. (FIG. 14.) There is a "domino" effect for the influence of peptides on pepMHC binding and specificity. A network of hydrogen bonding interacts from the peptide down to Ly49C contact region. (FIG. 15.)

Figure 16:
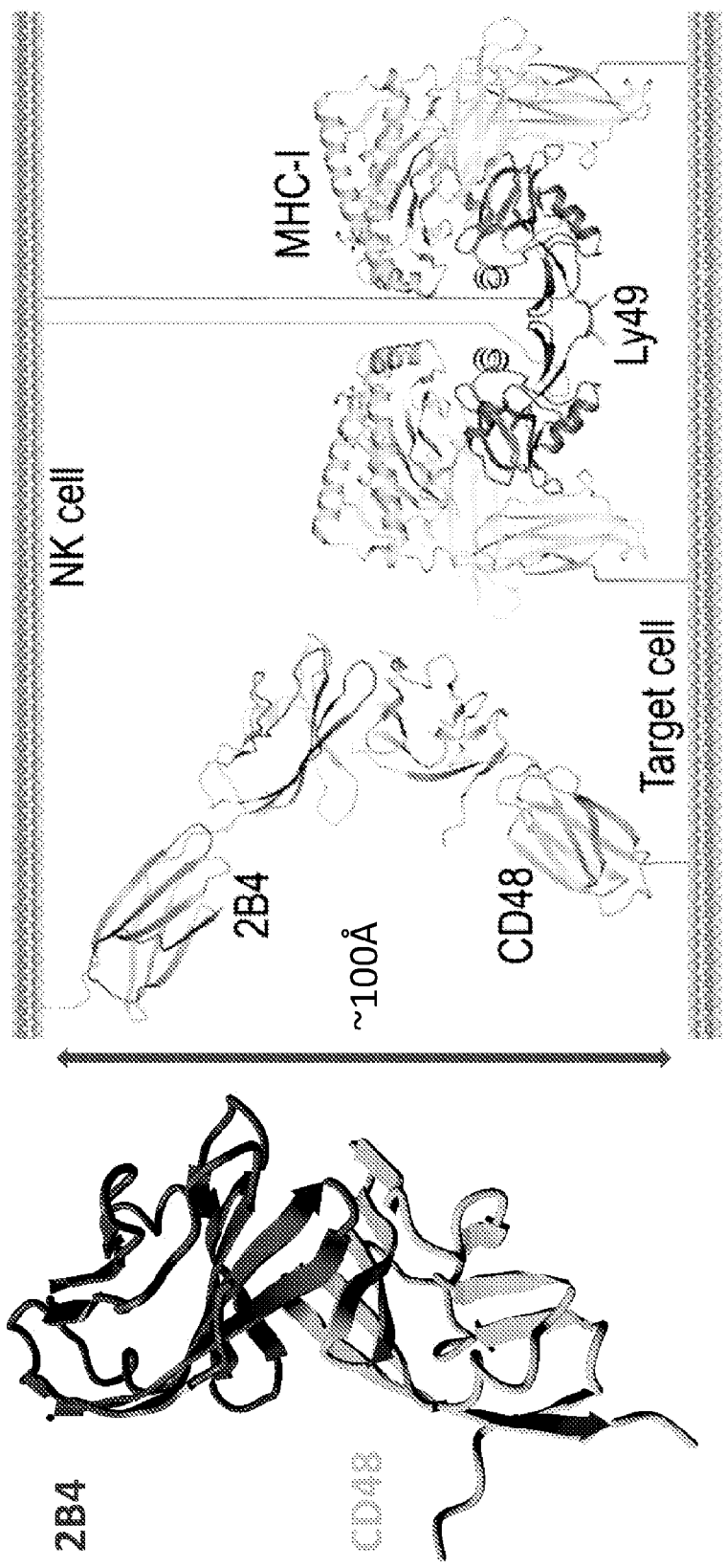
FIG. 16 illustrates crystallization of 2B4-CD48, and the mouse NK cell immune synapse. The structure of the Ly49C-H-2 Kb complex (1P4L) does not include the 70-residue stalk regions that connect the Ly49C homodimer to the NK cell membrane.
Figure 17:
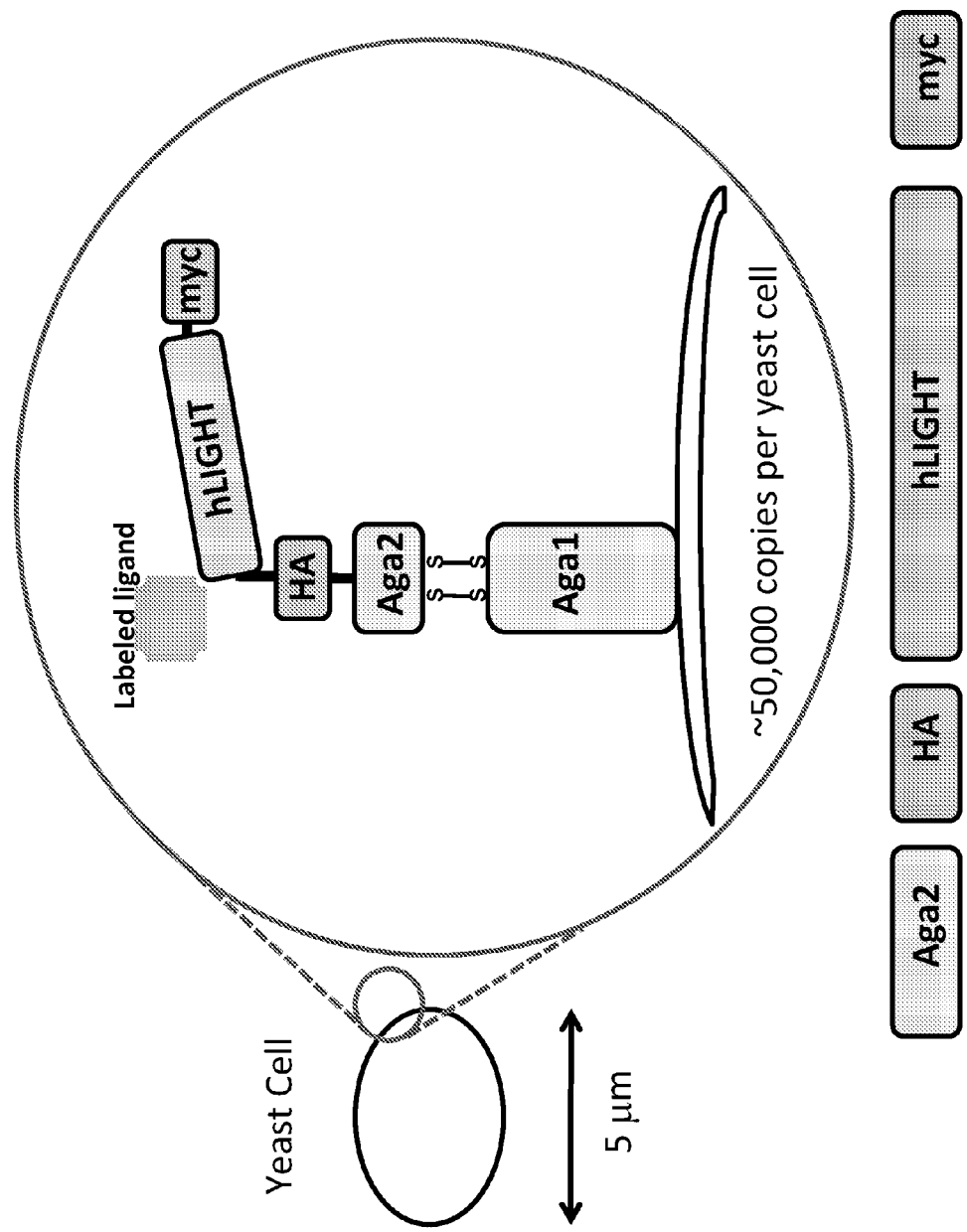
FIGS. 17 and 18 illustrate the engineering of the new human LIGHT mutants using Yeast Display (YD). Human LIGHT was fused to mating adhesion receptor Aga2. Fluorescent epitope tags were used for normalization, and equilibrium, kinetic and thermal stability analysis was assessed by flow cytometry.
Figure 18:
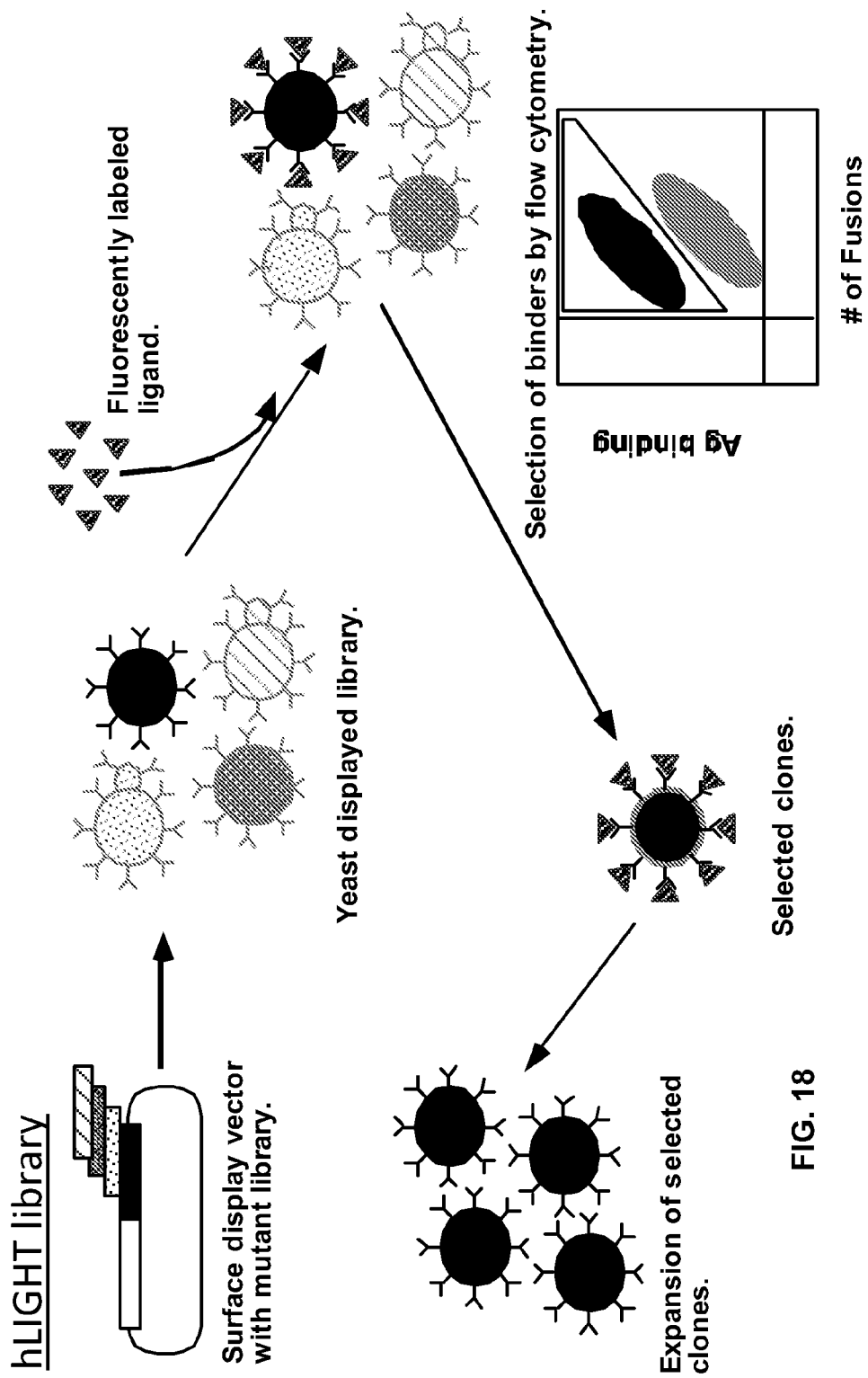
Figure 19:
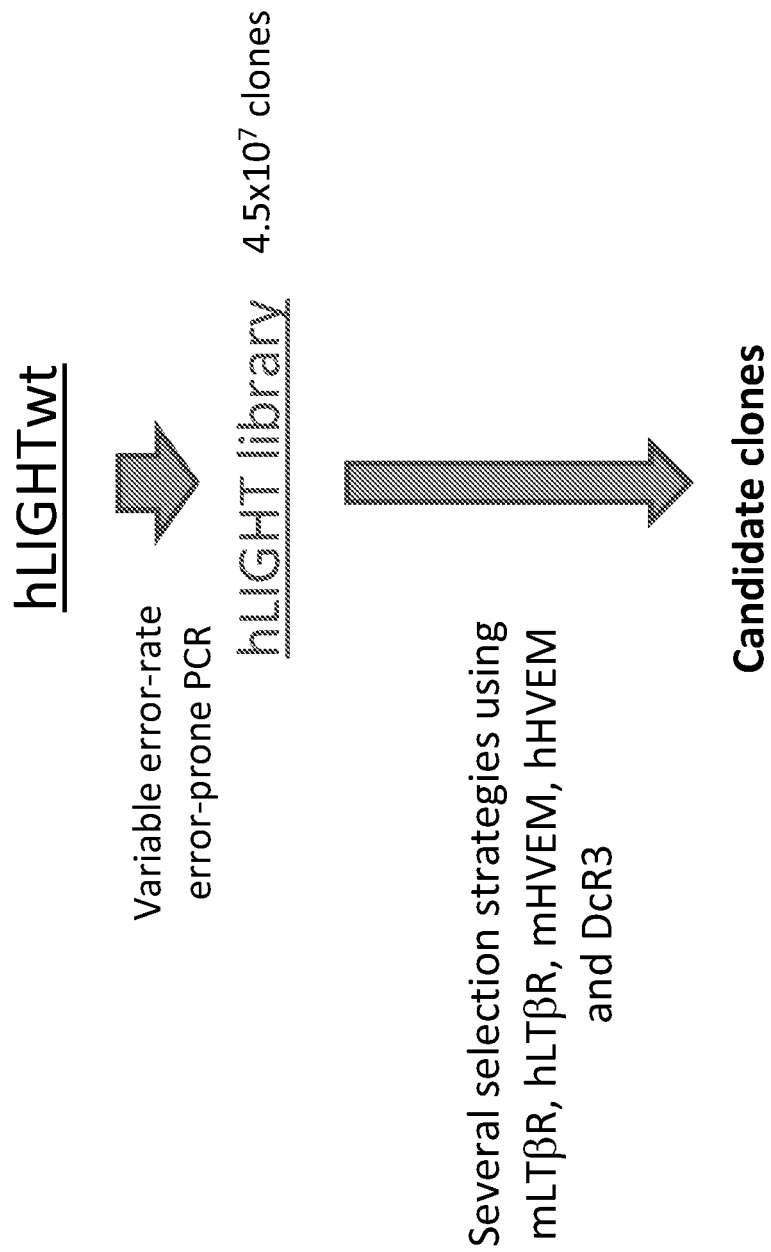
FIG. 19 shows how the human LIGHT library was generated for use in YD. Human LIGHT was subjected to variable error-rate error-prone PCR, which generated 4.5× $10^7$ clones. Selection was performed using the mouse and human LIGHT receptors mLTβR, mHVEM and hLTβR, hHVEM, respectively.

An engineered CD48 facilitated crystallization of the 2B4-CD48 complex. (FIG. 16.)

hLIGHT was engineered using yeast-display. hLIGHT was fused to mating adhesion receptor Aga2 using epitope Tags for normalization. Equilibrium, kinetic and thermal stability analysis was by flow cytometry. (FIGS. 17-19)

Figure 20:
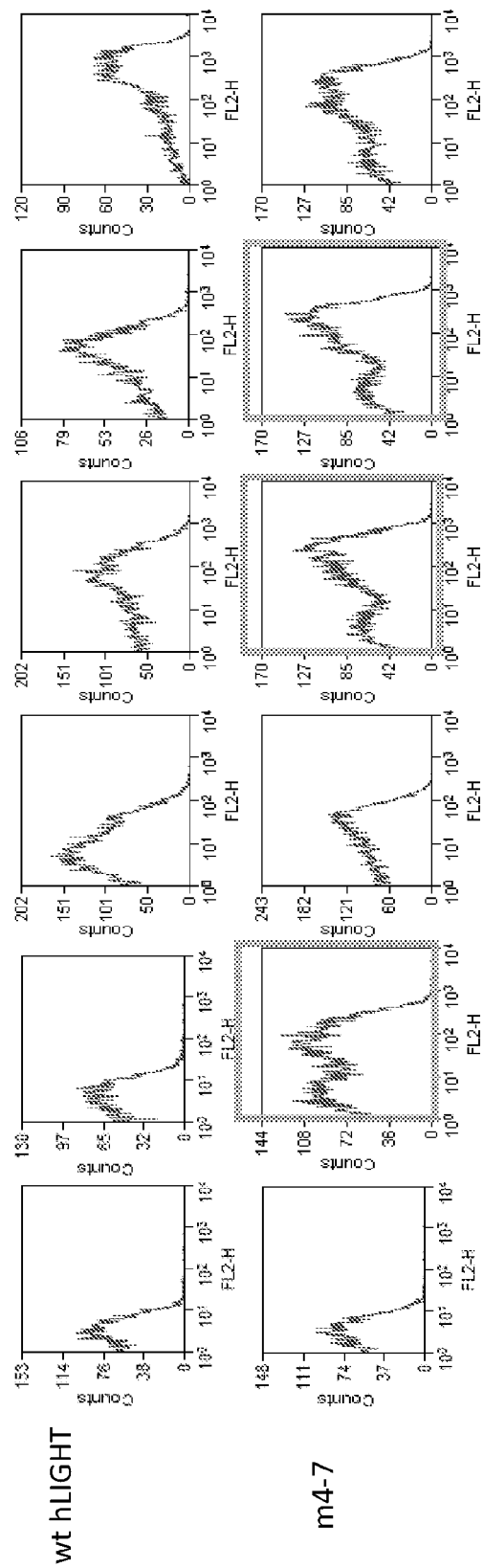
FIG. 20 shows the binding properties of isolated mutants (constructs) when tested against the mouse and human LTβR and HVEM.
Figure 20:
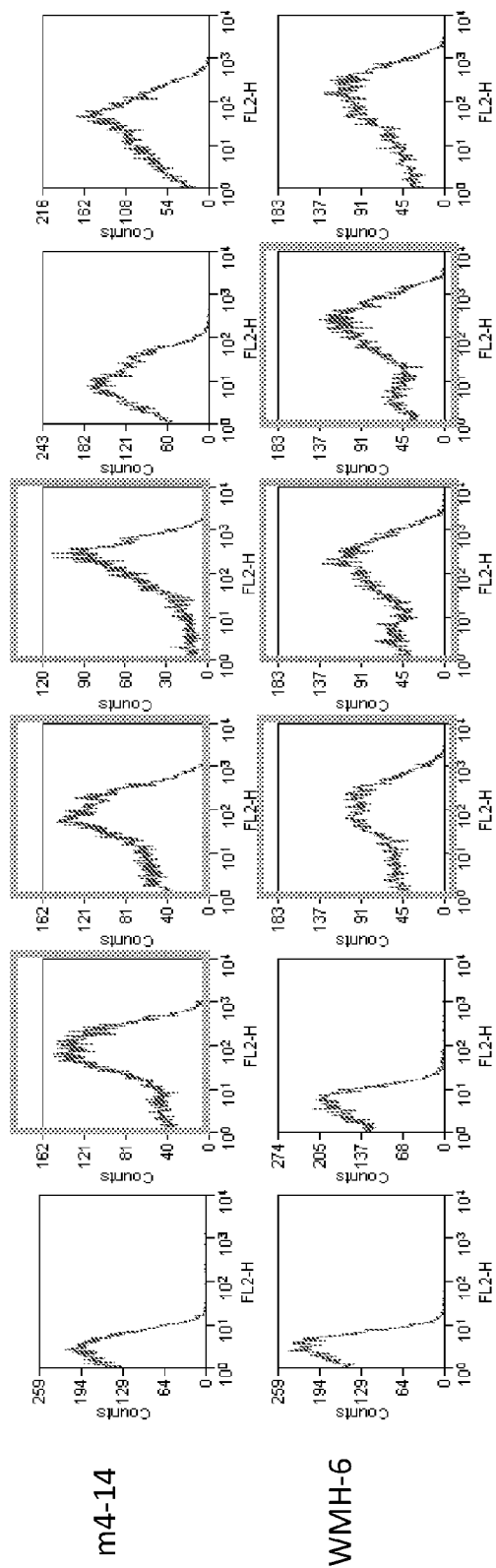
Figure 20:
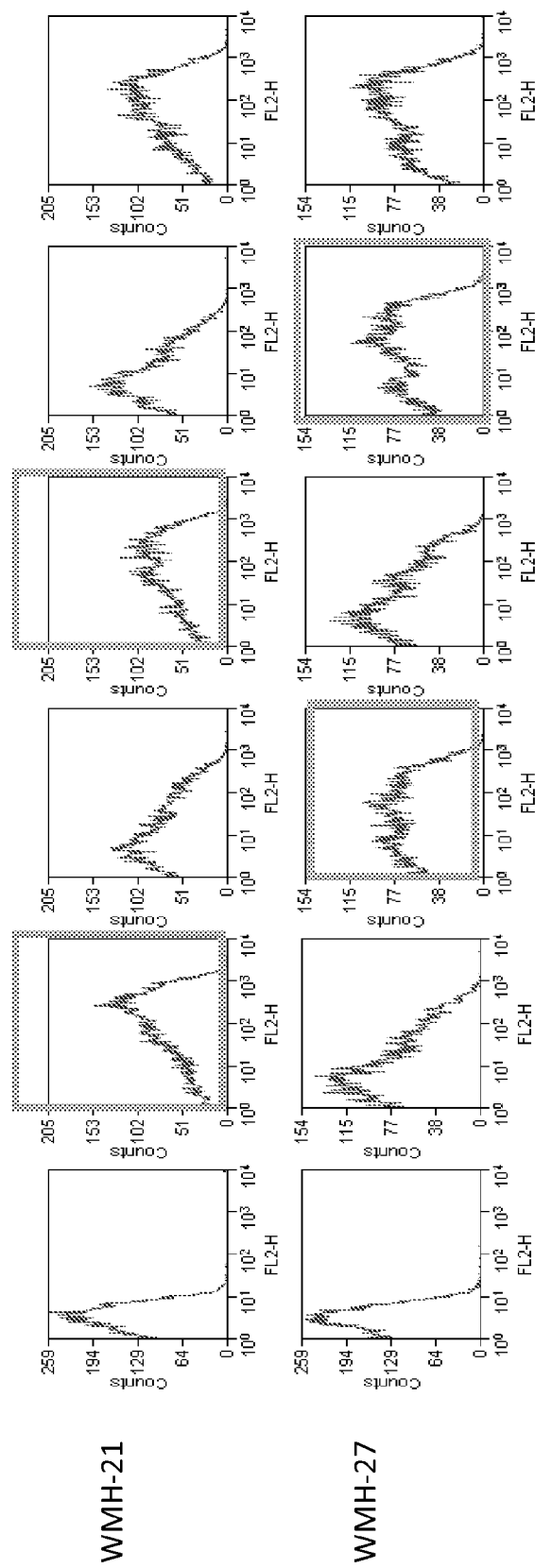
Figures 21, 22:
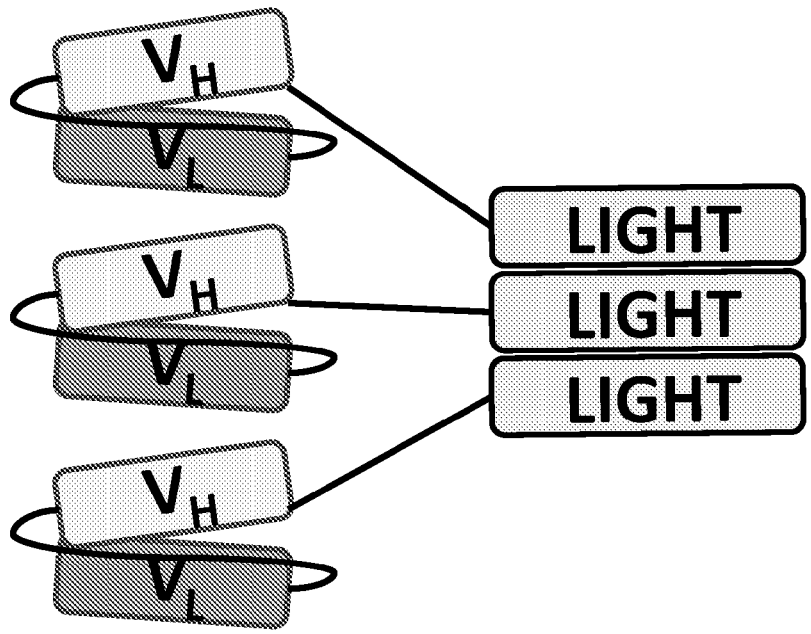
FIG. 21 shows the increased binding affinity of the human LIGHT mutants to mLTβR and mHVEM.
FIG. 22 illustrates an scFV (neu)-LIGHT fusion protein. The fusion protein was generated with a c-terminal streptavidin tag II for enhanced detection by western blot, flow cytometry and ELISA, and for high specificity, one-step purification.

The mutants of human LIGHT had improved binding properties and affinity when tested against the mouse and human LTβR and HVEM. (FIGS. 20-21.)

A scFV (neu)-LIGHT fusion protein was generated. A glutamine-synthetase vector allowed gene amplification with MSX, and adeno E1a co-transfection was used for transcriptional enhancement. A C-terminal Strep-Tag II sequence provides detection by western blot, ELISA, flow cytometry and high-specificity 1-step purification. (FIG. 22)

Figure 23:
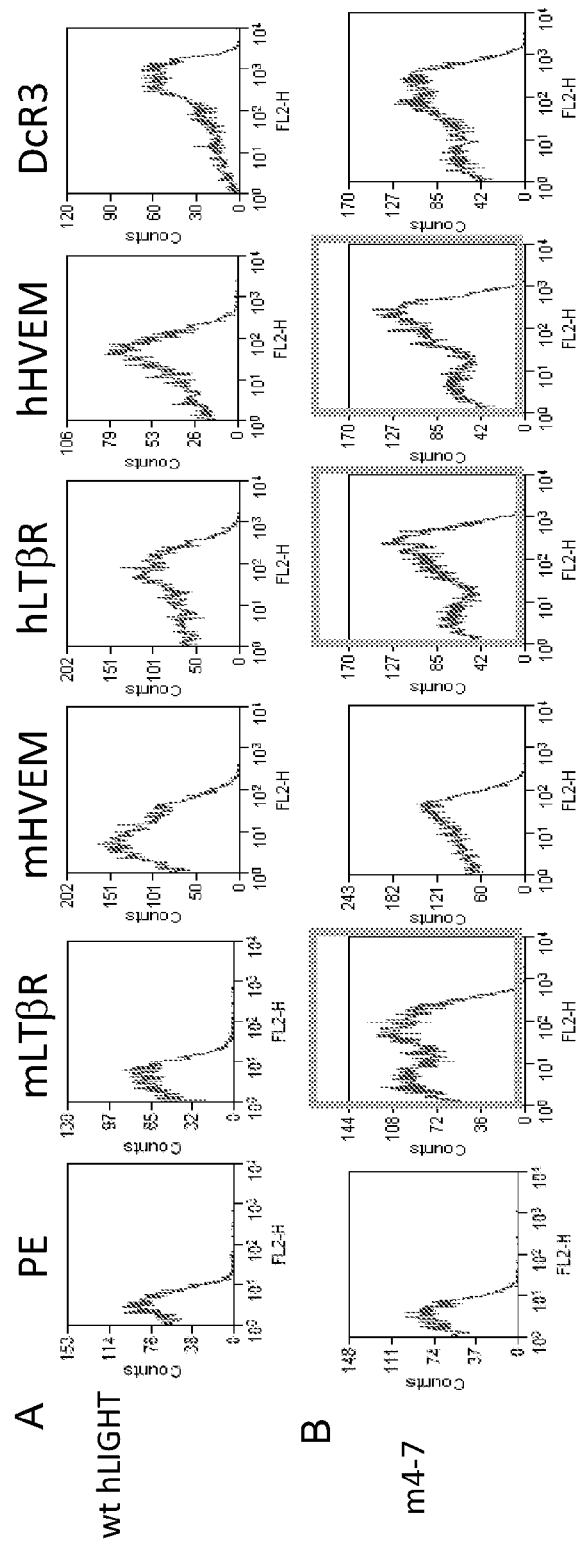
FIG. 23 (A-D) shows favorable binding of 4 mutant human LIGHT clones for mLTβR, mHVEM and hLTβR, hHVEM.
Figure 23:
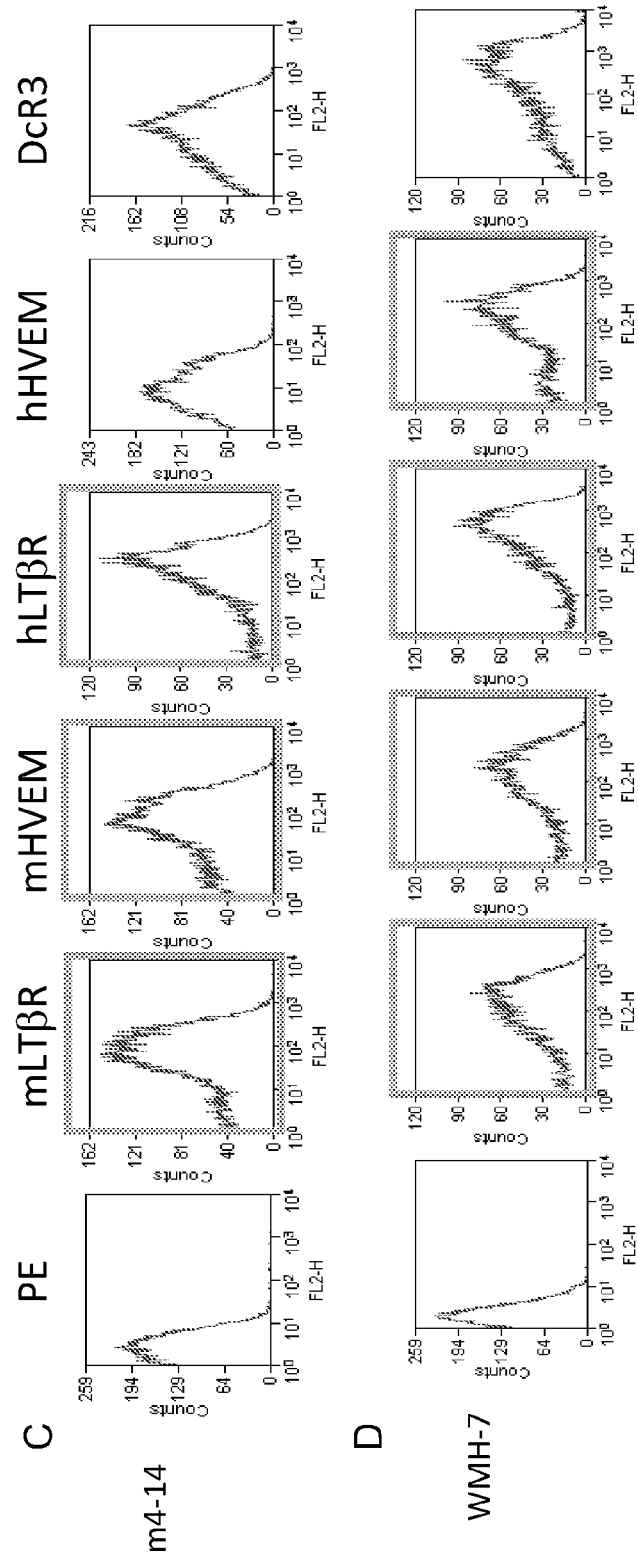
Figure 24:
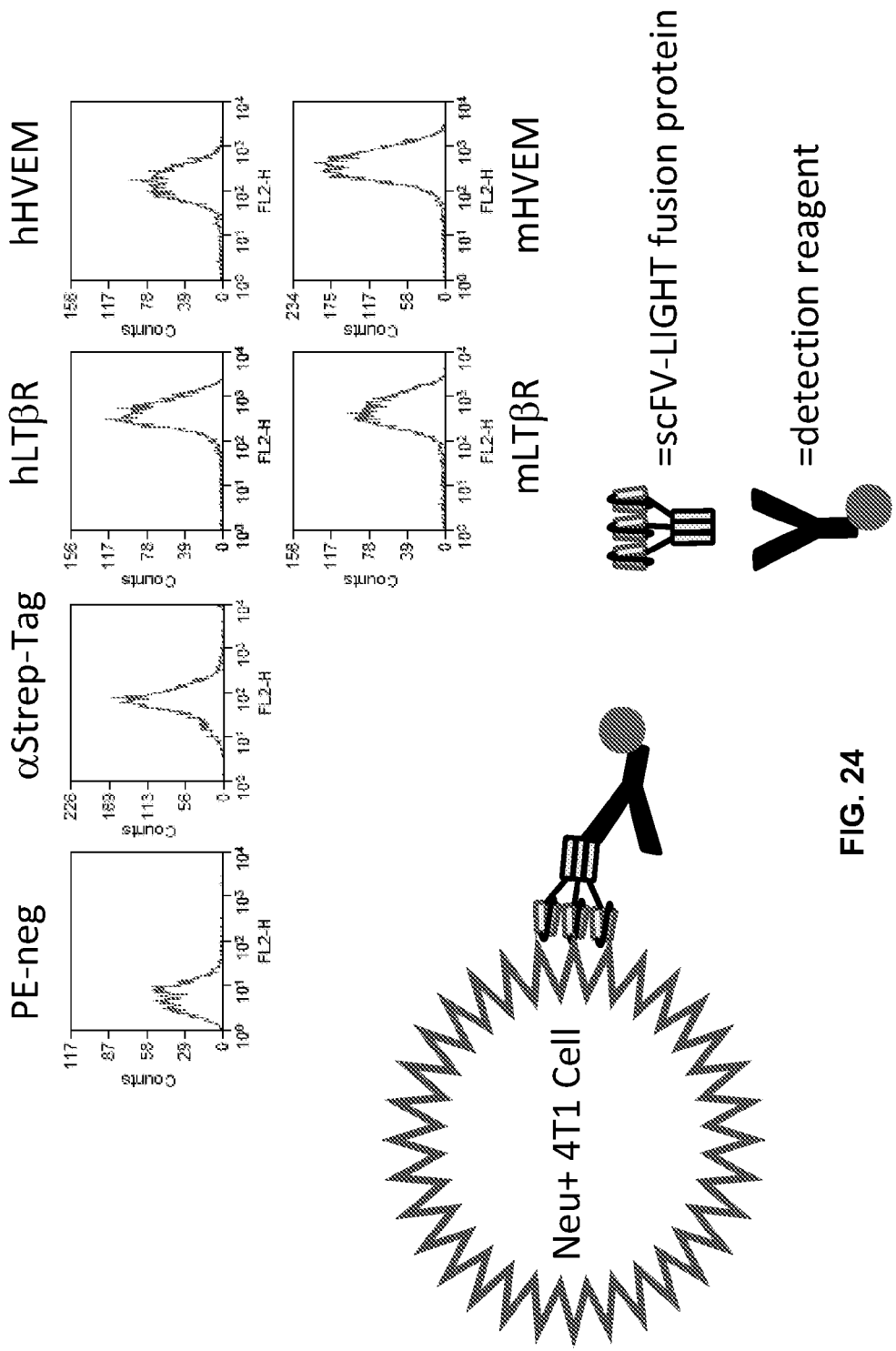
FIG. 24 shows that scFV and LIGHT bind their respective ligands when produced as an scFV-LIGHT fusion protein.
Figure 25:
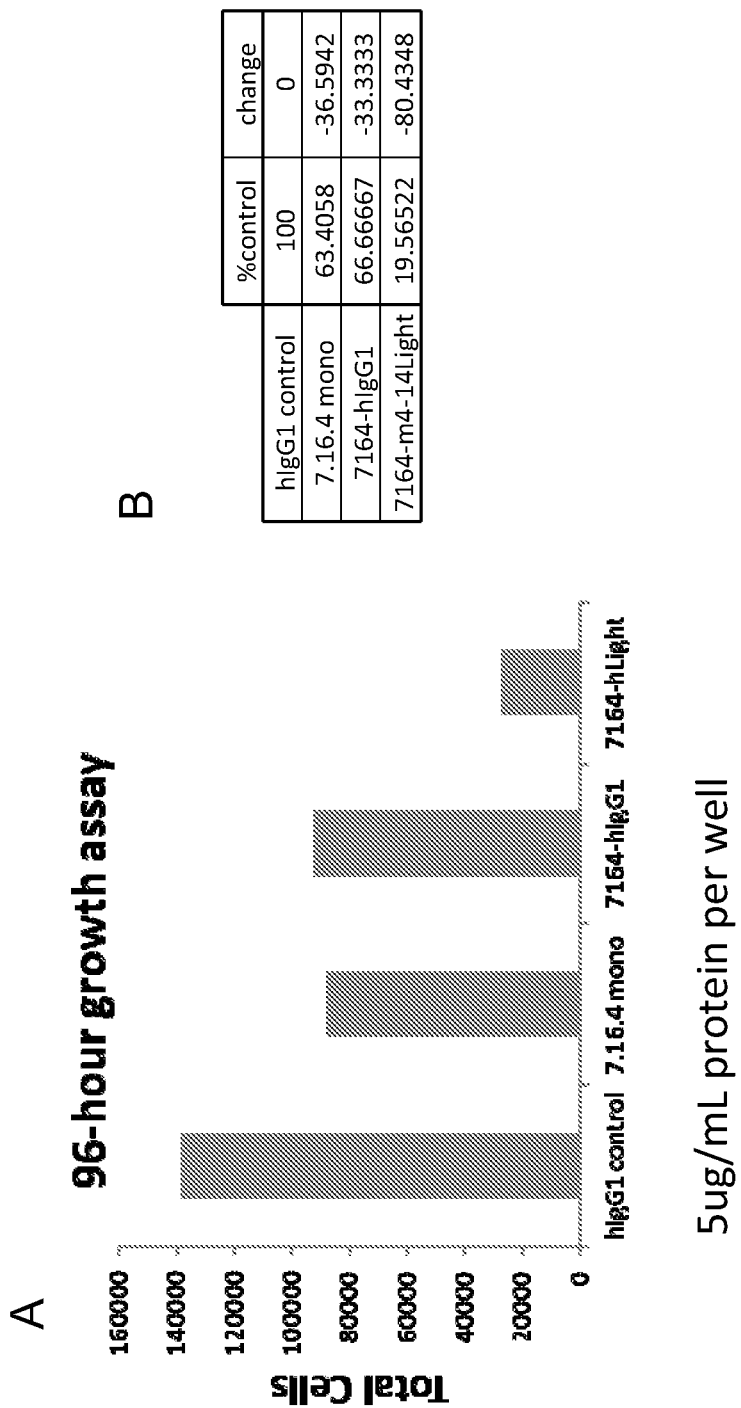
FIGS. 25 and 26 show that scFV(neu)-LIGHT fusion protein decreases growth of TUBO cells in culture. TUBO is a cloned cell line generated from a spontaneous mammary gland tumor from a BALB-neuT mouse and highly expresses HER-2 protein on the cell membrane. (A) TUBO cells were cultured and treated with 5 ug/mL protein, and assessed for growth after four days. (B) The fusion protein 7164 m4-14LIGHT, generated from an anti-neu single chain antibody and the mutant human LIGHT m4-14, significantly decreased growth of TUBO cells as compared to the antibody-treated or untreated cells.
Figure 26:
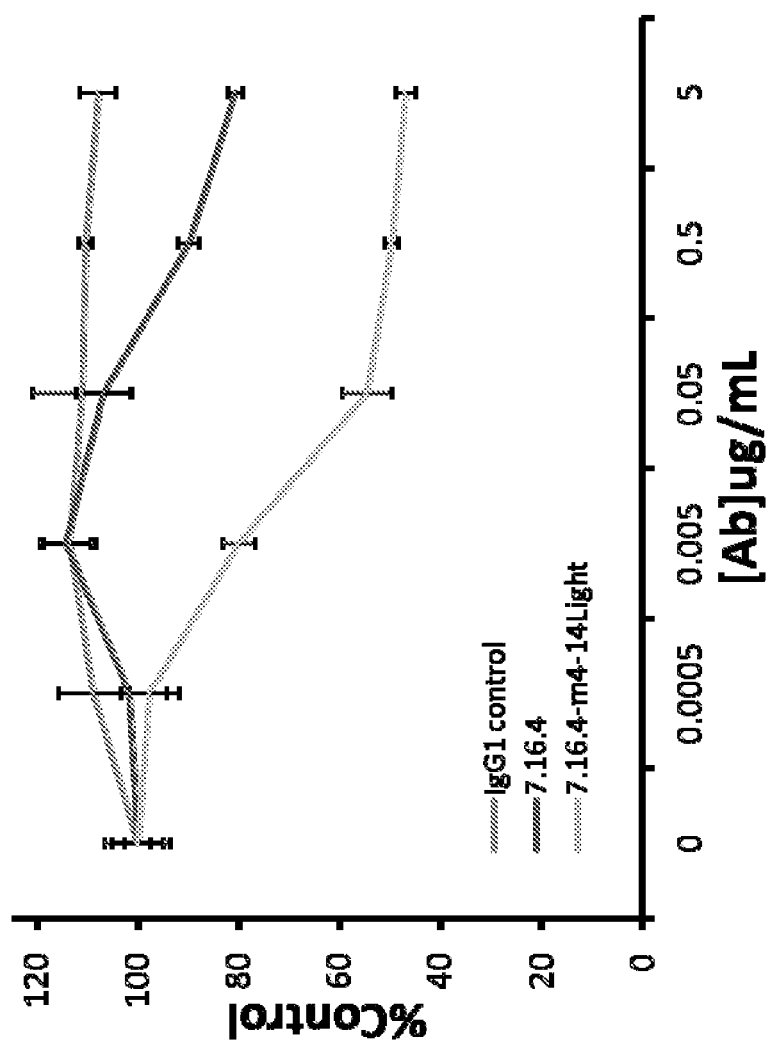
Figure 27:
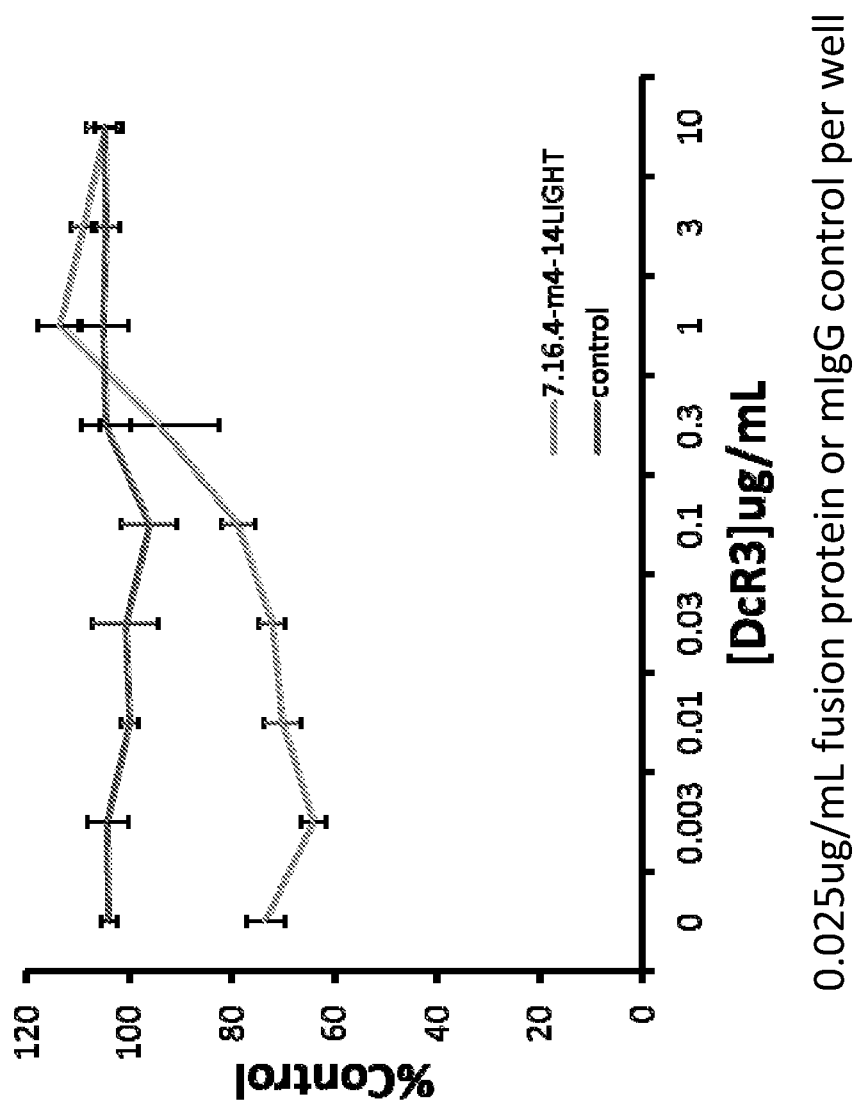
FIG. 27 shows that cell death caused by 7164 m4-14LIGHT is mediated via the interaction between LIGHT and LTβR.
Figure 29:
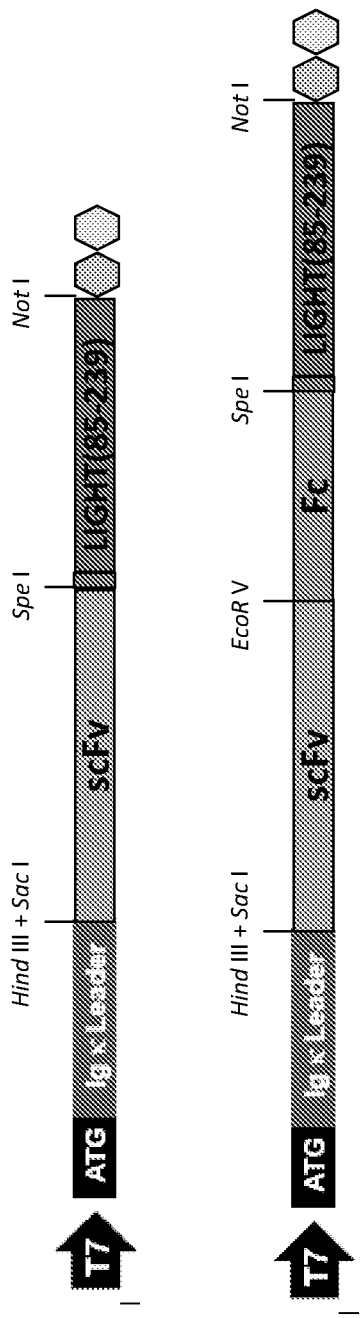
FIG. 29 are diagrams of scFV-LIGHT (85-239) fusion proteins.
Figure 30:
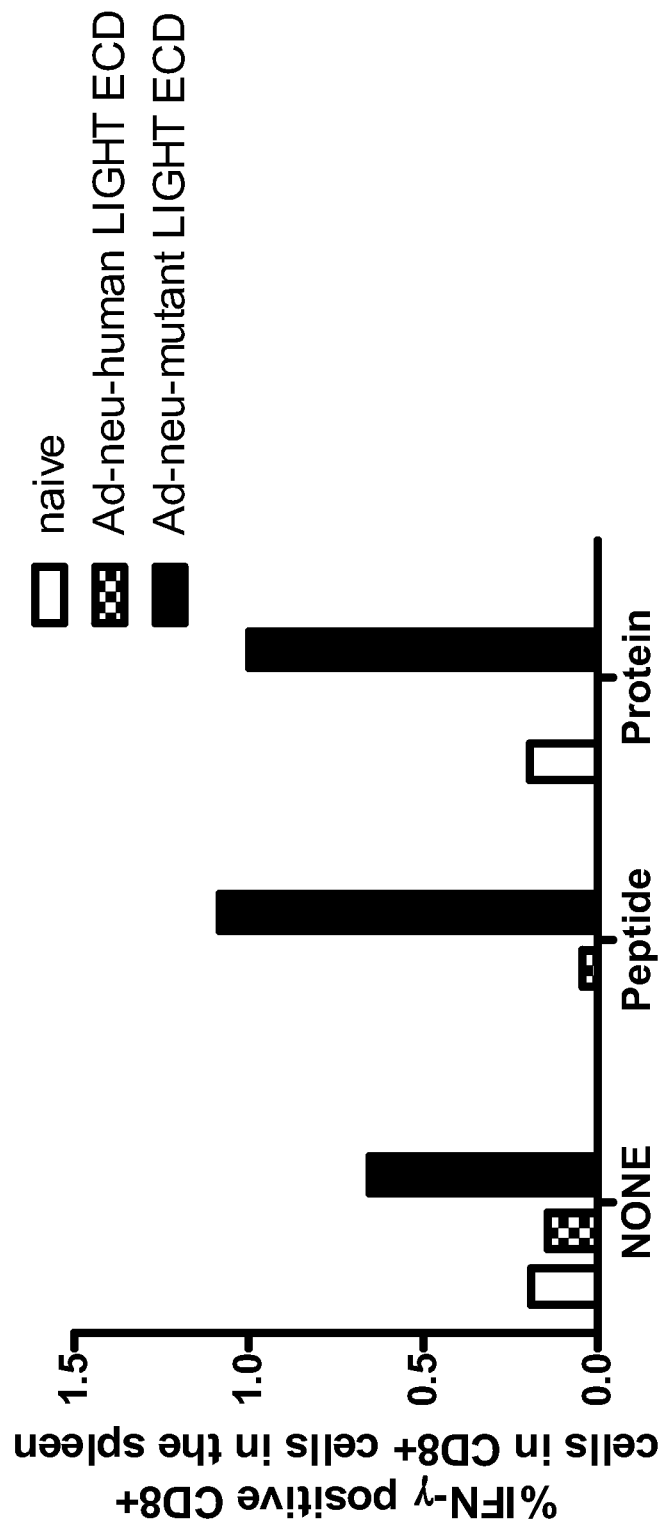
FIG. 30 shows that superLIGHT, an adenoviral construct that links a neu sequence via an IRES to the human mutant LIGHT m4-14, improves CD8-CTL response to new ICS. WT B/C mice were immunized with $5 \times 10^8$ IFU ad-neu-human LIGHT or ad-neu mutant LIGHT, and after 10 days, the splenocytes were made into singe cells and stimulated with neu-HIS protein or peptide RatP66, or left unstimulated. ICS was performed to detect IFN-gamma positive CD8 cells.
Figure 31:
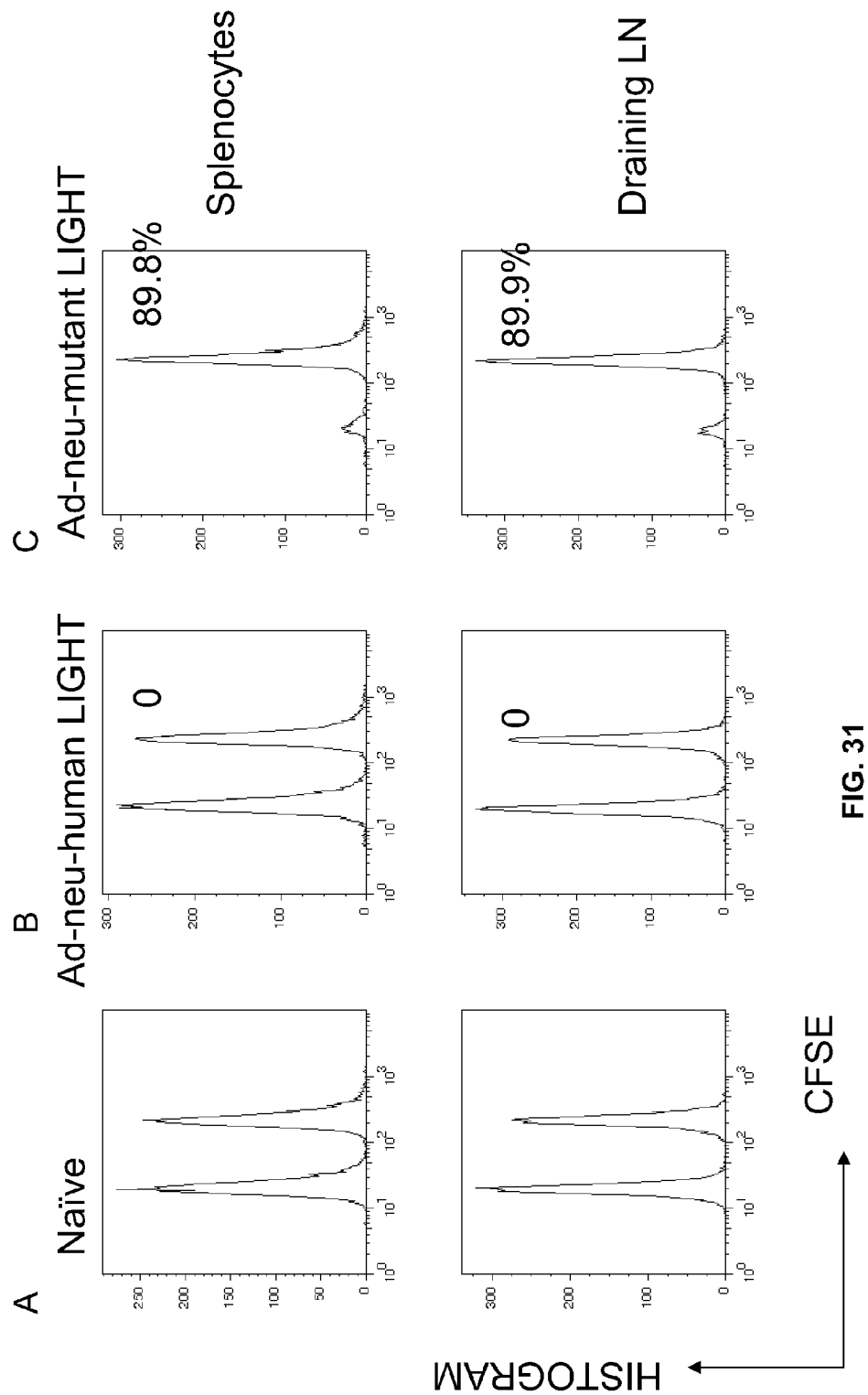
FIGS. 31 and 32 show superLIGHT (m4-14 mutant) improves CD8 CTL response to neu in vivo killing. WT B/C mice were immunized with (B) $5 \times 10^8$ IFU ad-neu-human LIGHT or (C) ad-neu mutant LIGHT. After 10 days, (A) naïve splenocytes were labeled with 0.5 uM and 5 uM CFSE and the 0.5 uM cells were also loaded with peptide Ratp66, equal numbers of the cells were mixed together and tail vein injected into naïve mice or immunized mice. After 16 hours, the spleen and draining lymph nodes (LN) were analysized for CFSE positive cells.
Figure 32:
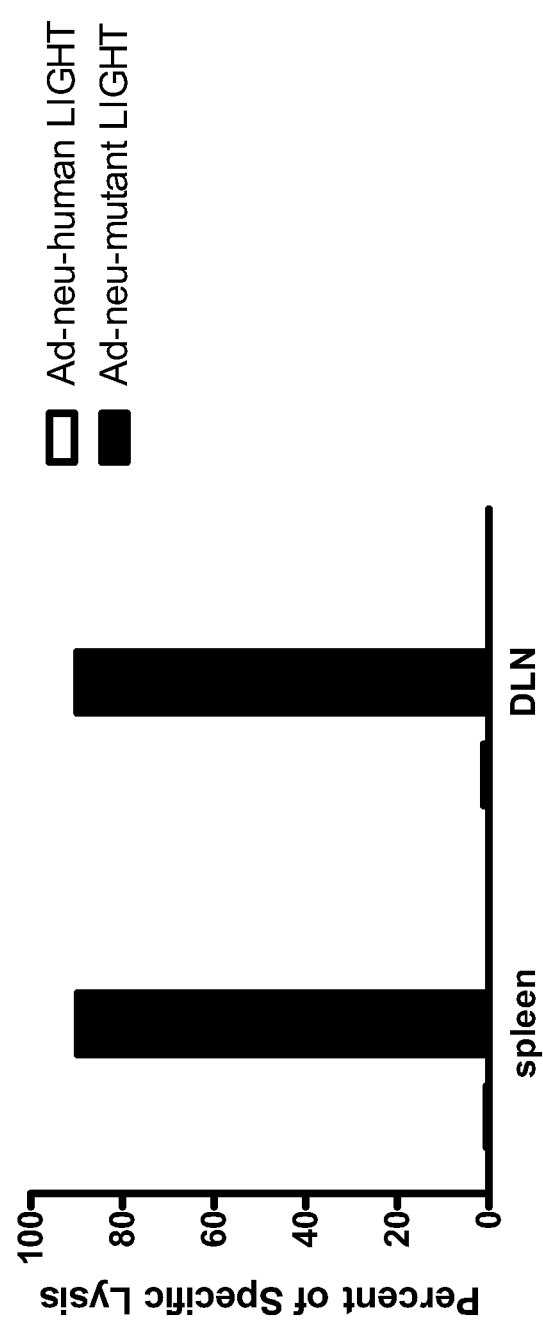
Figure 33:
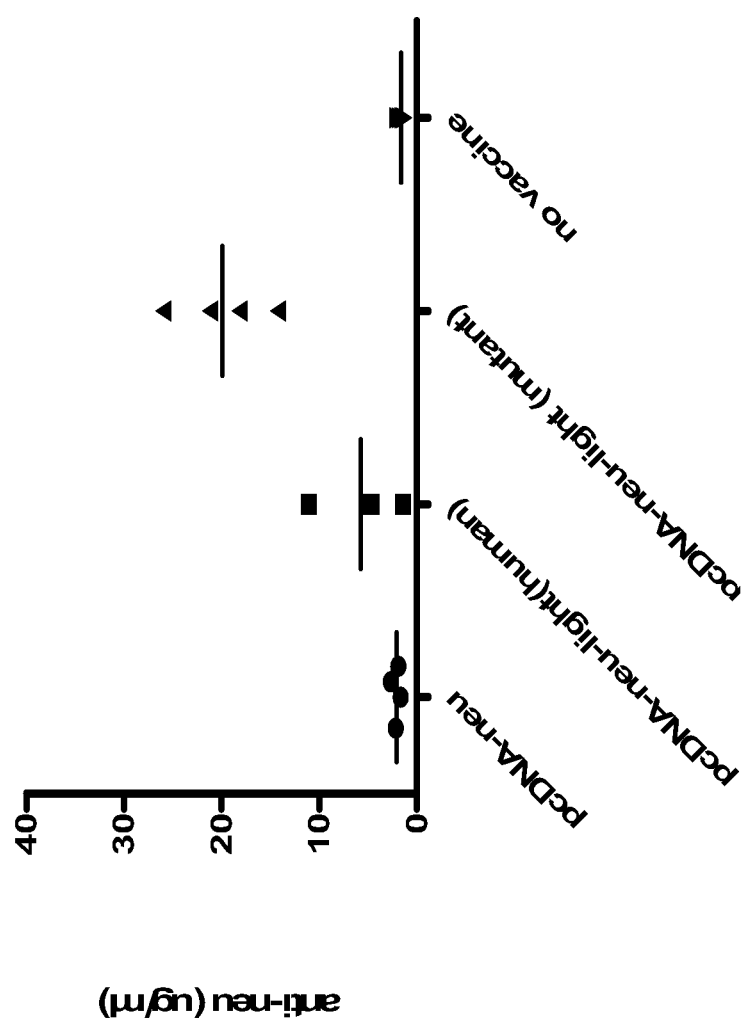
FIG. 33 shows super LIGHT induces higher anti-neu antibody after NA vaccine. Naïve mice (4 mice in each group) were immunized twice at 14 day intervals with PcDNA-neu or PcDNA-neu-LIGHT(human or mutant) by hydrodynamic injection. Seven days after the second immunization, mouse serum was collected and anti-neu antibody was tested using cellular ELISA.
Figure 34:
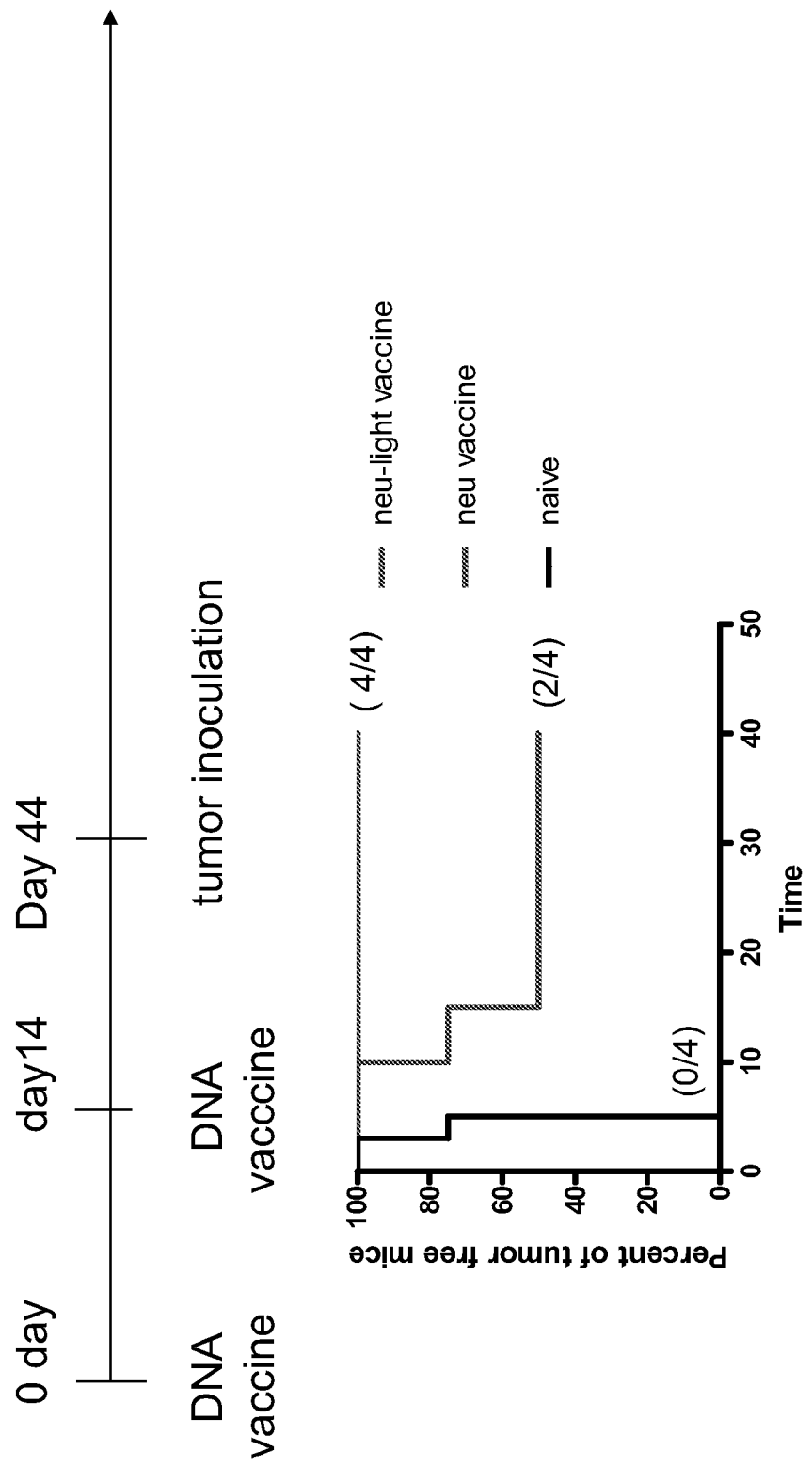
FIG. 34 shows improved efficiency of new super LIGHT DNA vaccine in 10 of tumor free mice (in vivo). Naïve mice (4 mice in each group) were immunized with PcDNA-neu or PcDNA-neu-LIGHT(mutant) by hydrodynamic injection. Forty four days later, the immunized mice were inoculated with 5*10⁵ TUBO cells. Tumor free mice were sacrificed and analyzed after another 40 days.
Figure 35:
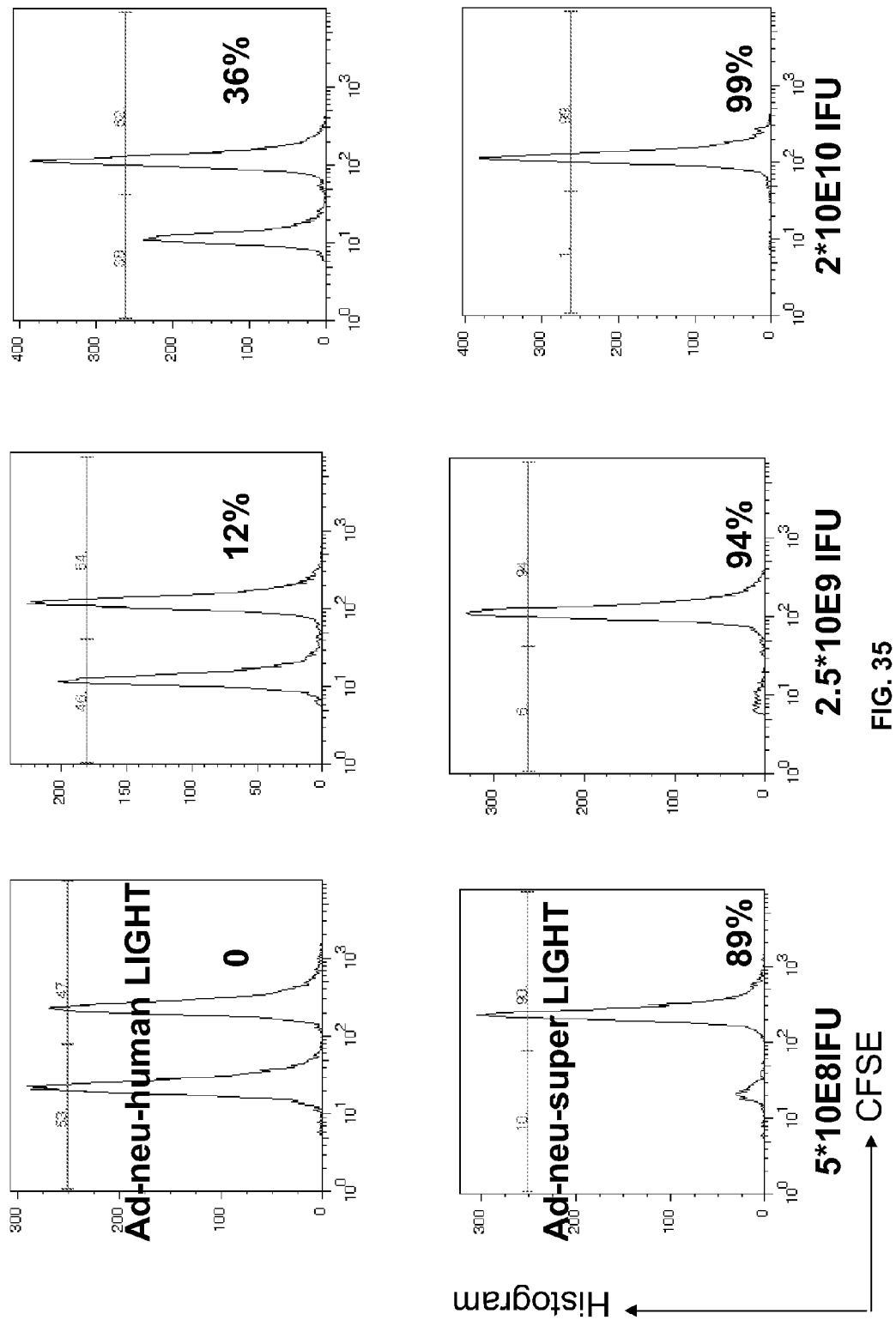
FIGS. 35 and 36 shows that super LIGHT improves neu-specific killing compound to hLIGHT, Naïve Balb/c mice was vaccinated subcutaneously with several different doses of adenovirus. After eleven days, ICS is performed as the following: naïve splenocytes were labeled with 0.5 uM or 5 uM CFSE, and the CFSE low cells were loaded with her2/neu peptide, then equal numbers of CFSE low and high cells were injected into the immunized mice by tail vein, 20 hours later, the CFSE positive cells in the spleen of vaccinated mice were analyzed by FACS.
Figure 36:
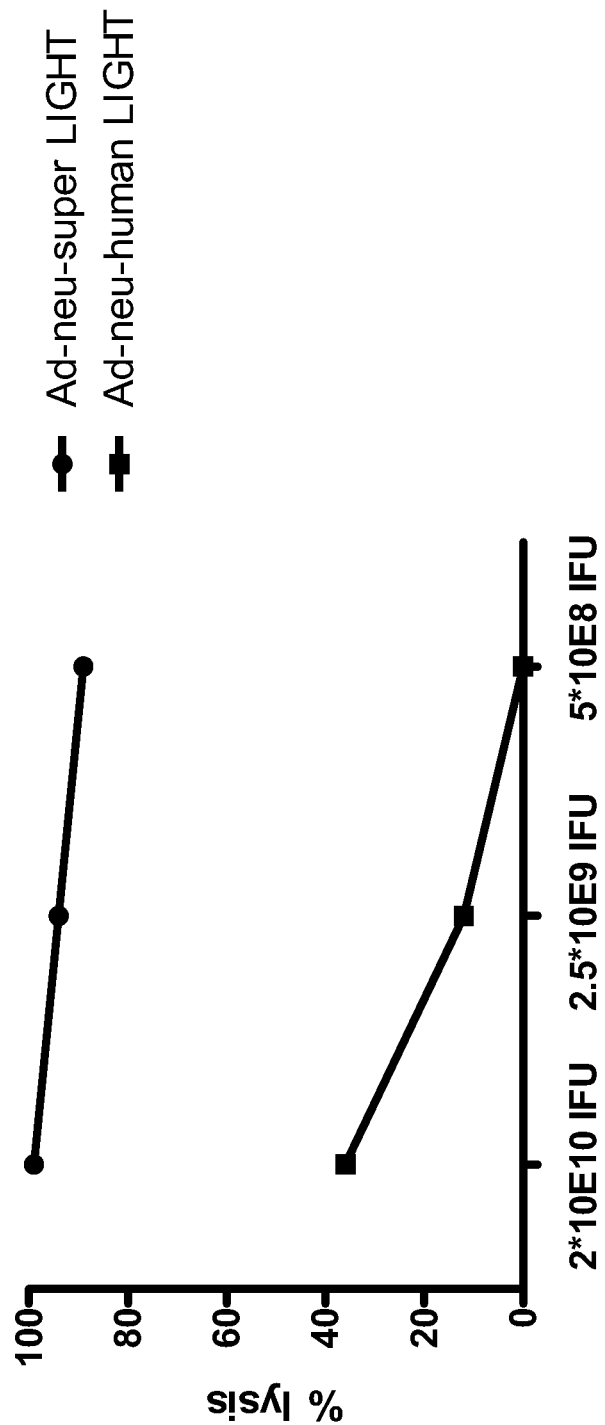
Figure 37:
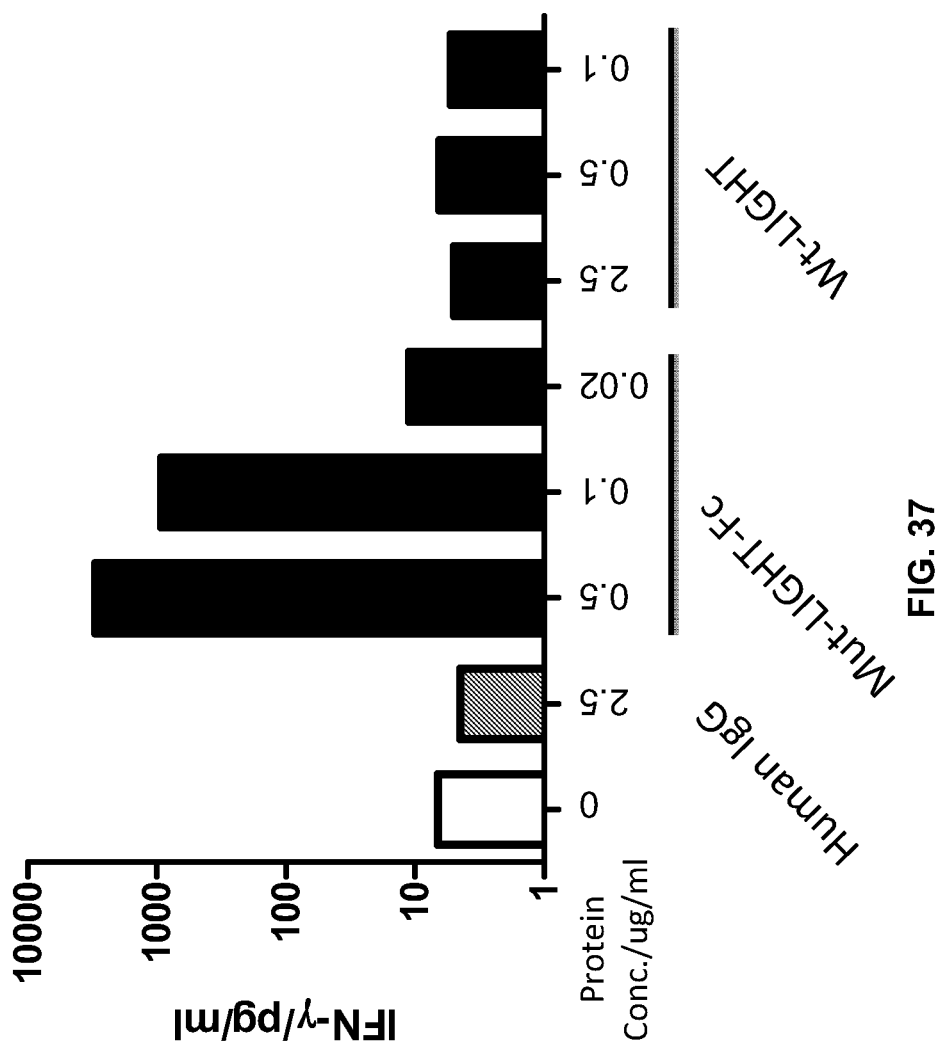
FIG. 37 demonstrates that LIGHT induced IFN-γ in Rag-1-Splenocytes.
Figure 38:
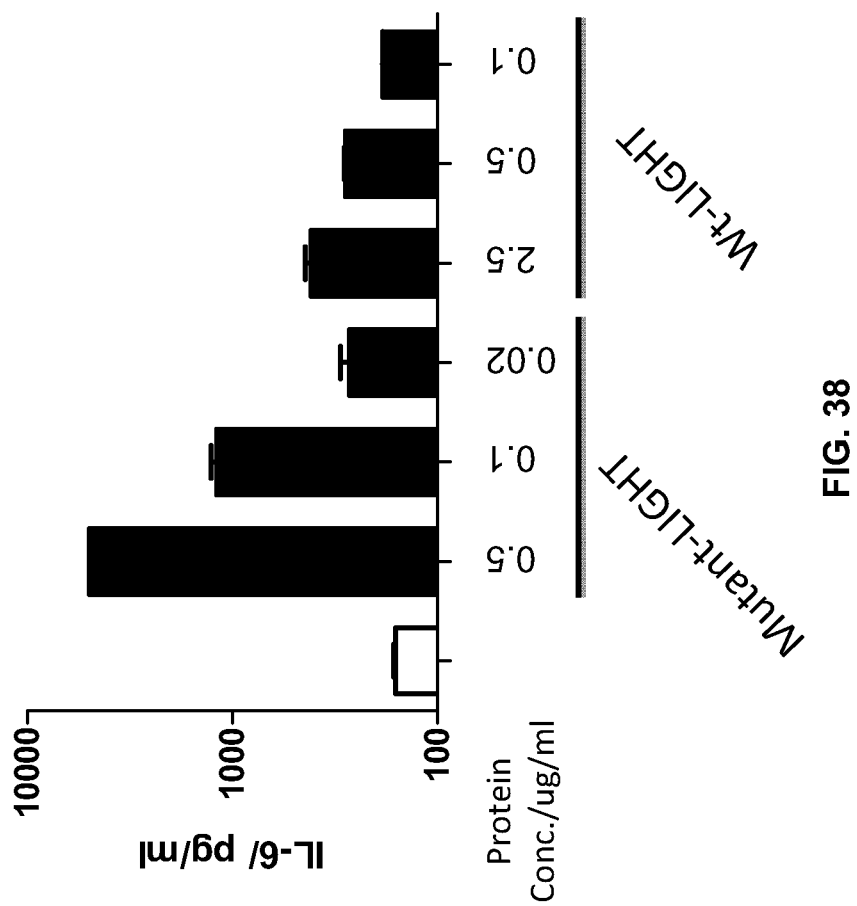
FIG. 38 demonstrates that LIGHT induced IL-6 in MEF cells.

A new set of clones was isolated with favorable binding for all 4 desired receptors. scFV-LIGHT fusion was produced in CHO cells. Both scGV and LIGHT bound their respective ligands. (FIGS. 23-24)

scFV(neu)-LIGHT fusion protein decreases growth of Tubo cells in culture. Fusion protein mediated cell death was due to the direct effects of LIGHT on LTβR expressed on tumor cells. (FIGS. 25-27)

Materials and Methods

The Generation of Fusion Protein of Antibody-LIGHT.

A recombinant antibody construct designated heterominibody was developed that allows for the specific targeting of LIGHT to an antibody that binds to a tumor antigen or tumor cells with high affinity using standard protocol.

Mice, Cell Lines, and Reagents.

Female C3HXC57BL/6 F1 (C3B6F1) mice, 4-8 weeks old were purchased from the National Cancer Institute, Frederick Cancer Research Facility, (Frederick, Md.). C57BL/6-RAG-1-deficient (RAG-1$^{-/-}$) mice were purchased from the Jackson Laboratory (Bar Harbor, Me.). H-Y TCR transgenic mice (H-Y mice) on the RAG-2-deficient/B6 background were purchased from Taconic Farms (Germantown, N.Y.). 2C TCR transgenic mice on RAG-1-deficient background bred into B6 for 10 generations (2C mice) were provided by J. Chen (Massachusetts Institute of Technology, Boston, Mass.). OT-1 TCR transgenic mice (OT-1 mice) were provided by A. Ma (The University of Chicago). RAG-1$^{-/-}$, H-Y, 2C, OT-1 mice were bred and maintained in the specific pathogen-free facility at the University of Chicago. Animal care and use were in accord with institutional guidelines.

The AG104A expressing murine H-2L$^d$ (AG104-L$^d$), the transfectant of AG104A cells, has been described previously (Wick M, 1997, JEM 186:229-38). These tumor cell lines were maintained in DMEM (Mediatech) supplemented with 10% FCS (Sigma-Aldrich), 100 U/ml penicillin, and 100 .mu.g/ml streptomycin (BioWhittaker). The hybridoma cell lines producing anti-L$^d$ (clone 30-5-7) and anti-2C TCR (1B2) antibodies were obtained from D. Sachs (National Institutes of Health, Bethesda, Md.) and T. Gajweski (The University of Chicago), respectively.

Monoclonal antibodies produced by hybridomas were purified from the culture supernatant with protein G column by procedures known to those of skill in the art. The antecedent 1B2 antibody was conjugated to FITC or biotin by the Monoclonal Antibody Facility of The University of Chicago. PE-coupled anti-CD8 antibody, Cy-chrome (CyC)-coupled streptavidin, CyC-coupled anti-CD44 antibody, PE-coupled anti-CD62L antibody and PE-coupled Th1.2 antibody were purchased from BD Biosciences. FITC-conjugated-goat-anti-mouse IgG was purchased from Caltag. PE-coupled streptavidin was purchased from Immunotech. PE-coupled donkey anti-human IgG was purchased from Jackson Immunological Research Lab (West grove, PA). Biotinylated goat anti-SLC antibody was purchased from R&D systems Inc. (Minneapolis, Minn.). AP conjugated rabbit anti-goat Ig antibody was purchased from Vector Laboratories Inc. (Burlingame, Calif.). Purified goat anti-SLC antibody was purchased from PeproTech (Rock hill, NJ). Collagenase (type 4) was purchased from Sigma-Aldrich. CFSE was purchased from Molecular Probes.

Tumor Growth In Vivo.

Tumor cells were injected subcutaneously into the lower back, that is, 0.5-1 cm above the tail base of the mice. Tumor growth was measured every 3 to 4 days with a caliper. Size in cubic centimeters was calculated by the formula πabc/6, where a, b, and c are three orthogonal diameters.

Histology.

Tumor tissues for histology examination were collected at time indicated and fixed in 10% neutral buffered formalin, processed to paraffin embedment, and stained with hematoxylin and eosin. For immunohistochemical staining of SLC, tumor tissues were harvested, embedded in OCT compound (Miles-Yeda, Rehovot, Israel) and frozen at −70.degree. C. Frozen sections (5-10 μm thick) were fixed in cold 2% formalin in PBS and permeablized with 0.1% saponin/PBS. The sections were preblocked with 5% goat serum in 0.1% saponin/PBS for half an hour at room temperature in a humidified chamber. Staining for SLC was done by first incubating with biotinylated goat anti-SLC antibody (R&D systems Inc. Minneapolis, Minn.) at a 1/25 dilution in blocking buffer. Alkaline phosphatase conjugated rabbit anti-goat Ig antibody (Vector Laboratories Inc. Burlingame, Calif.) was added 2 h later. For immunofluorescence staining, sections were blocked with 2% normal mouse serum, rabbit serum, and goat serum in PBS for half an hour at room temperature in a humidified chamber. Blocking solution was replaced with 50 μl of primary Abs. PE-conjugated anti-Th1.2 (BD PharMingen), or PE-conjugated anti-CD8 (BD PharMingen), diluted 1/100 in blocking solution, and sections were incubated for 1 h at room temperature in a humid chamber. Specimens were mounted in Mowiol 4-88 (BD Biosciences, La Jolla, Calif.) containing 10% 1,4-diazobicyclo [2.2.2]octane. Samples were analyzed within 48 h using a Zeiss Axioplan microscope (Zeiss, Oberkochen, Germany) and a Photometrics PXL CCD camera (Photometrics, Tucson, Ariz.). No-neighbor deconvolution was performed using Openlab v2.0.6 (Improvision, Lexington, Mass.).

ELISA for CCL21.

Tumor homogenates were prepared and assayed for CCL21. Comparable amount of tumor tissues from tumor-bearing mice were collected and weighed, homogenized in PBS that contained protease inhibitors, and the supernatants were collected by centrifugation. Polystyrene 96-well microtiter plates (Immulon 4, Dynatech Laboratories, Chantilly, Va.) were coated with goat anti-mouse CCL21 at 2 μg/ml in PBS and were then blocked with 0.1% bovine serum albumin (BSA) in PBS for 30 min at room temperature. After washing, serial dilutions of standards of known concentrations (Recombinant CCL21, 50 ng/ml, R&D) and samples were added and incubated for 2 h at room temperature. After 3 washes, biotinylated rabbit anti-SLC Ab was added to the wells. After 2 h incubation and washing, 50 μl of a 1/1000 diluted alkaline phosphatase-conjugated avidin (Dako) was added for 1 h and then developed. Color development was measured at 405 nm on an automated plate reader (Spectra-Max 340, Molecular Devices, Sunnyvale, Calif.) and The amount of CCL21 was determined by ELISA from the standard curve, and normalized according to tissue weight. Data are mean.+−.s.d.

T-Cell Co-Stimulation Assay.

T cells were purified by a negative selection method in the magnetic field as instructed by the manufacture (Miltenyi Biotec, Auburn, Calif.). The purity of isolated T cells was greater than 95%, as assessed by flow cytometry using monoclonal antibody against CD3. Plates coated with 0.2 g/ml monoclonal antibody against CD3 were further coated at 37° C. for 4 h with Mutant LIGHT-flag. After being washed, purified T cells (1×10$^6$ cells/ml) were cultured in the wells. Monoclonal antibody against CD28 (1 μg/ml) was used in soluble form. In all assays, the proliferation of T cells was assessed by the addition of 1 Ci/well $^3$H-thymidine during the last 15 h of the 3-day culture $^3$H-thymidine incorporation was measured in a TopCount microplate scintillation counter (Packard instrument, Meriden, Conn.).

Cell Isolation from Tumor Tissue.

The mice were first bled to decrease the blood contamination of tumor tissue. The tumor tissues were collected, washed in the PBS, cut into pieces, and resuspended in DMEM supplemented with 2% FCS and 1.25 mg/ml collagenase D (collagenase D solution) for 40 min in a 37.degree. C. shaking incubator. The single cell suspension was collected after 40 min, and the cell clumps were digested for another 40 min in the collagenase D solution until all tumor tissue had resolved into a single cell suspension.

Pharmaceutical Compositions.

Therapeutic compositions used herein can be formulated into pharmaceutical compositions comprising a carrier suitable for the desired delivery method. Suitable carriers include materials that when combined with the therapeutic composition retain the anti-tumor function of the therapeutic composition. Examples include a number of standard pharmaceutical carriers such as sterile phosphate buffered saline solutions, bacteriostatic water, and the like. Therapeutic formulations can be solubilized and administered via any route suitable to deliver the therapeutic composition to the tumor site. Potentially effective routes of administration include intravenous, parenteral, intraperitoneal, intramuscular, intratumor, intradermal, intraorgan, orthotopic, and the like. A formulation for intravenous injection includes the therapeutic composition in a solution of preserved bacteriostatic water, sterile unpreserved water, and/or diluted in polyvinylchloride or polyethylene bags containing sterile sodium chloride for injection. Therapeutic protein preparations can be lyophilized and stored as sterile powders, preferably under vacuum, and then reconstituted in bacteriostatic water (containing for example, benzyl alcohol preservative) or in sterile water prior to injection. Dosages and administration protocols for the treatment of cancers using the methods disclosed herein may vary with the method and the target cancer, and generally depend on a number of factors appreciated and understood in the art.

Measurement of Cytokines in the Spleen and Tumor.

Tumor and spleen homogenates was prepared as described (Yu et al., 2003 JEM197:985-995). Briefly, comparable amounts of tumor or spleen tissues were collected, weighed and homogenized in PBS containing protease inhibitors, and the supernatants were collected by centrifugation. The amount of cytokines in the supernatants was quantified using the cytometric bead array kit (CBA) (BD Biosciences) on a FACS Caliber cytometer equipped with CellQuestPro and CBA software (Becton Dickinson) according to manufacture's instruction.

Statistical Analysis for Difference in Tumor Growth.

Because the tumor growth was observed repeatedly over time on the same mouse, the random effect models for longitudinal data were used to analyze such data. For each experiment, the tumor growth was assumed to depend on treatment and to follow a linear growth rate over time. The model gave an overall estimate of the intercept and slope of the linear growth for each group. Both the intercept and slope were allowed to vary among individual mouse. The slope, i.e., the growth rate was compared was different among different treatment groups. Because the actual tumor growth may not follow a linear growth trend over the entire follow up period. The increase of tumor growth was slow at the early stage and became rapid at the later stage in some experiments. A quadratic term was added to the follow-up time in the above random effect models.

Generation of mutant LIGHT Expression Vectors and Clones pcDNA3.1-LIGHT was used as template to generate two dsDNA fragments A and B by PCR. For generation of fragment A (about 500 b.p.), sense primer 5'-CATGGATC-CAAGACCATGGAGAGTGTGGTACA-3' (SEQ ID NO: 36) (the bold text indicated BamHI site) and antisense primer 5'-AGATCGTTGATCTTGCCAGGAGCCTTT-GCC-3' (SEQ ID NO: 37) were used. To generate fragment B (about 200 b.p.), sense primer 5'-GGCAAAGGCTCCTG-GCAAGATCAACGATCT-3' (SEQ ID NO: 38) and antisense primer 5'-ACCTCTAGATCAGACCAT-GAAAGCTCCGA-3' (SEQ ID NO: 39) (the underlined text indicated XbaI site) were used. The antisense primer for fragment A is complimentary with sense primer for fragment B, which covers sequences for amino acid (a.a.) 73-87 among which a.a. 79-82 were deleted. Fragments A and B were mixed, denatured at 94 degrees C. and cooled down to room temperature to anneal the two DNA fragments. The annealed DNA product was used as template for a PCR reaction and the product was cloned into pcDNA3.1 using BamHI and XbaI. The deletion of a.a. 79-82 was verified by sequencing. To generate pMFG-mutant LIGHT, pcDNA3.1-mutant LIGHT was digested with NcoI and BamHI and ligated to a NcoI and BamHI-digested the pMFG-S-TPA plasmid (Mulligan R C, Massachusetts Institute of Technology, Boston, Mass.).

Delivery of a nucleic acid encoding mutant human LIGHT into a patient may be either direct, in which case the patient is directly exposed to the nucleic acid or nucleic acid-carrying vectors, or indirect, in which case, tumor cells obtained from a biopsy are first transformed with the nucleic acids in vitro, irradiated and then transplanted into the patient. These approaches are routinely practiced in gene therapies for suppressing tumors or treating other illness.

Delivery of Nucleic Acids.

The nucleic acid sequences are directly administered in vivo, where they are expressed to produce the encoded products. This can be accomplished by any of numerous methods known in the art, e.g., by constructing them as part of an appropriate nucleic acid expression vector and administering it so that they become intracellular, e.g., by infection using defective or attenuated retroviral or other viral vectors (U.S. Pat. No. 4,980,286), or by direct injection of naked DNA, or by use of microparticle bombardment, or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (which can be used to target cell types specifically expressing the receptors), etc. Alternatively, the nucleic acid can be introduced intracellularly and incorporated within host cell DNA for expression, by homologous recombination.

Biodegradable microspheres have also been used in gene delivery that encapsulate the nucleic acid. Microspheres such as matrices, films, gels and hydrogels which include hyaluronic acid (HA) derivatized with a dihydrazide and crosslinked to a nucleic acid forming slow release microspheres have been used to deliver nucleic acids. U.S. Pat. No. 6,048,551 discloses a controlled release gene delivery system utilizing poly (lactide-co-glycolide) (PLGA), hydroxypropylmethyl cellulose phthalate, cellulose acetate phthalate, and copolymer microspheres to encapsulate the gene vector.

The therapeutic compositions used in the practice of the foregoing methods can be formulated into pharmaceutical compositions comprising a carrier suitable for the desired delivery method. Suitable carriers include materials that when combined with the therapeutic composition retain the anti-tumor function of the therapeutic composition. Examples include, but are not limited to, any of a number of standard pharmaceutical carriers such as sterile phosphate buffered saline solutions, bacteriostatic water, and the like. Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing sterile sodium chloride for injection. Therapeutic protein preparations can be lyophilized and stored as sterile powders, preferably under vacuum, and then reconstituted in bacteriostatic water (containing for example, benzyl alcohol preservative) or in sterile water prior to injection. Dosages and administration protocols for the treatment of cancers using the foregoing methods will vary with the method and the target cancer, and will generally depend on a number of other factors appreciated in the art.

Delivery Using Viral Vectors.

Viral vectors that contain nucleic acid sequences encoding an antibody of the invention are used for delivering specific nucleic acids. For example, a retroviral vector can be used. These retroviral vectors contain the components necessary for the correct packaging of the viral genome and integration into the host cell DNA. The nucleic acid sequences encoding the desired protein to be used in gene therapy are cloned into one or more vectors, which facilitates delivery of the gene into a patient. Adenoviruses are other viral vectors that can be used in gene therapy. Adenoviruses are especially attractive vehicles for delivering genes to respiratory epithelia and other targets for adenovirus-based delivery systems are liver, the central nervous system, endothelial cells, and muscle. Adenoviruses have the advantage of being capable of infecting non-dividing cells. Adeno-associated virus (AAV) has also been proposed for use in gene therapy (U.S. Pat. No. 5,436,146). Lentiviruses are promising for use in gene therapy.

Transfecting cells in tissue culture followed by delivery to patients. Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient. In this method, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. The technique should provide for the stable transfer of the nucleic acid to the cell, so that the nucleic acid is expressible by the cell and preferably heritable and expressible by its cell progeny.

The resulting recombinant cells may be irradiated and can be delivered to a patient by various methods known in the art. Recombinant cells (e.g., hematopoietic stem or progenitor cells) are preferably administered intravenously. The amount of cells envisioned for use depends on the desired effect, patient state, etc., and can be determined by one skilled in the art. Cells into which a nucleic acid can be introduced for purposes of gene therapy encompass any desired, available cell type, and include but are not limited to epithelial cells, endothelial cells, keratinocytes, fibroblasts, muscle cells, hepatocytes, blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

Vaccines.

As used herein, the term "vaccine" refers to a composition (e.g., a mutant human LIGHT antigen and an adjuvant) that elicits a tumor-specific immune response. These vaccines include prophylactic (preventing new tumors) and therapeutic (eradicating parental tumors). A vaccine vector such as a DNA vaccine encoding a mutant human LIGHT can be used to elicit immune response against tumors. The response is elicited from the subject's own immune system by administering the vaccine composition at a site (e.g., a site distant from the tumor). The immune response may result in the eradication of tumor cells in the body (e.g., both primary and metastatic tumor cells). Methods for generating tumor vaccines are well known in the art (See e.g., U.S. Pat. Nos. 5,994,523 and 6,207,147 each of which is herein incorporated by reference).

The vaccines may comprise one or more tumor antigens in a pharmaceutical composition. In some cases, the tumor antigen is inactivated prior to administration. In other embodiments, the vaccine further comprises one or more additional therapeutic agents (e.g., cytokines or cytokine expressing cells).

In certain cases, cells selected from a patient, such as fibroblasts, obtained, for example, from a routine skin biopsy, are genetically modified to express one or of the desired protein. Alternatively, patient cells that may normally serve as antigen presenting cells in the immune system such as macrophages, monocytes, and lymphocytes may also be genetically modified to express one or more of the desired antigens. The antigen expressing cells are then mixed with the patient's tumor cells (e.g., a tumor antigen), for example in the form of irradiated tumor cells, or alternatively in the form of purified natural or recombinant tumor antigen, and employed in immunizations, for example subcutaneously, to induce systemic anti-tumor immunity. The vaccines may be administered using any suitable method, including but not limited to, those described above.

Cancer metastasis may be reduced by stimulation of at least one of the following including chemokines, adhesion molecules, and costimulatory molecules for priming naive T-cells. Cancer types include breast cancer, lung cancer, prostrate cancer, colon cancer, and skin cancer.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be performed following the method of Winter and co-workers [Jones et al., Nature, 321:522-525 (1986); Riechmann et al., Nature, 332:323-327 (1988); Verhoeyen et al., Science, 239: 1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Various forms of a humanized antibody-LIGHT fusions or conjugates are contemplated. For example, the humanized antibody may be an antibody fragment, such as a Fab, which is conjugated with LIGHT or an extracellular fragment thereof. Alternatively, the humanized antibody may be an intact antibody, such as an intact IgG1 antibody.

As an alternative to humanization, human antibodies can be generated. For example, it is possible to produce transgenic animals (e.g., mice) that are capable, upon immunization, of producing a variety of human antibodies in the absence of endogenous immunoglobulin production. See, e.g., Jakobovits et al., Proc. Natl. Acad. Sci. USA, 90:2551 (1993); Jakobovits et al., Nature, 362:255-258 (1993).

Alternatively, phage display technology (McCafferty et al., Nature 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle (See e.g., Johnson, Kevin S, and Chiswell, David J., Current Opinion in Structural Biology 3:564-571 (1993)). Human antibodies may also be generated by in vitro activated B cells (see U.S. Pat. Nos. 5,567,610 and 5,229,275).

Various techniques have been developed for the production of antibody fragments. Traditionally, these fragments were derived via proteolytic digestion of intact antibodies. However, these fragments can also be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries. The antibody fragment may also be a "linear antibody", e.g., as described in U.S. Pat. No. 5,641,870 for example. Such linear antibody fragments may be monospecific or bispecific.

Conjugates of the antibody and a co-stimulatory molecules such as LIGHT may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bisazido compounds (such as bis(p-azidobenzoyl) hexanediamine), bis-diazonium derivatives (such as bis-(p-diazoniumbenzoyl)-ethylenediaminc), di isocyanates (such as tolyene 2,6-diisocyanate), and bis-active fluorine compounds (such as 1,5-difluoro-2,4-dinitrobenzene). An extracellular domain of LIGHT or fragments thereof are conjugated to an antibody or antibody fragments that are specific to a tumor antigen, preferably, a surface tumor antigen.

Alternatively, a fusion protein comprising the anti-tumor antigen antibody and LIGHT may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

The antibody-LIGHT complexes disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in U.S. Pat. Nos. 4,485,045 and 4,544,545; and WO97/38731 published Oct. 23, 1997. Liposomes with enhanced circulation time are disclosed in U.S. Pat. No. 5,013,556.

For the prevention or treatment of disease, the dosage and mode of administration will be chosen by the physician according to known criteria. The appropriate dosage of LIGHT, Antibody-LIGHT conjugate or fusion product may depend on the type of cancer to be treated, the severity and course of the disease, the size of the tumor, the extent of metastases, whether the antibody is administered for preventive or therapeutic purposes, previous therapy, the patient's clinical history and response to the antibody, and the discretion of the attending physician. The LIGHT or antibody-LIGHT composition is suitably administered to the patient at one time or over a series of treatments. Preferably, the composition is administered by intravenous infusion or by subcutaneous injections. Depending on the type and severity of the disease, about 1 .mu.g/kg to about 50 mg/kg body weight (e.g., about 0.1-15 mg/kg/dose) of antibody can be an initial candidate dosage for administration to the patient, whether, for example, by one or more separate administrations, or by continuous infusion. A dosing regimen may include administering an initial loading dose of about 5 mg/kg, followed by a weekly maintenance dose of about 2 mg/kg of the anti-TAT antibody. However, other dosage regimens may be useful. A typical daily dosage might range from about 1 .mu.g/kg to 100 mg/kg or more, depending on the factors mentioned above. For repeated administrations over several days or longer, depending on the condition, the treatment is sustained until a desired suppression of disease symptoms occurs, e.g., reduction in tumor size/volume and reduction in metastases. The progress of this therapy can be monitored by conventional methods and assays and based on criteria known to the physician or other persons of skill in the art.

TABLE I

Ad-LIGHT eradicates metastases and promotes long-term survival

| Treatments and Time[a] | Time of Sacrifice, In Day[a] | Number of Mice Free of Tumor Cells in the Lung/All Mice (%)[b] |
|---|---|---|
| None | 14 | 3/22 (13.6%) |
| Surgery on day 14 | 35 | 0/10 (0%) |
| Ad-control[c] on day 14 + Surgery on day 24 | 35 | 0/35 (0%) |
| Ad-LIGHT[c] on day 14 + Surgery on day 24 | 35 | 18/35 (51.4%) |
| Ad-LIGHT and CD8 depletion[d] and day 14 + Surgery on day 24 | 35 | 0/35 (0%) |

[a]Days after primary tumor inoculation.
[b]Pooled from several independent experiments.
[c]Total of 2.5 × 10^9 PFU Ad-control (LacZ) or Ad-LIGHT was injected intratumorly per mouse.
[d]A total of 125 mg of depleting anti-CD8 Ab was injected on day 14 and once every week.

The invention claimed is:

1. A pharmaceutical composition comprising a mutant human LIGHT molecule comprising an amino acid sequence selected from the group consisting of SEQ ID Nos: 3, 4, 5, and 20, having increased binding affinity for murine receptors of LIGHT as compared to wild type human LIGHT, and having at least the same affinity to human receptors of LIGHT as compared to wild type human LIGHT, wherein the composition stimulates cytotoxic T lymphocytes against tumor cells.

2. The pharmaceutical composition of claim 1, wherein a tumor specific agent is linked to the mutant human LIGHT molecule.

3. The pharmaceutical composition of claim 2, wherein the tumor specific agent is selected from the group consisting of a humanized monoclonal antibody, a chimeric antibody, a heterominibody, a single chain antibody, and an antibody fragment sufficient to recognize a tumor antigen, and where the tumor antigen is EGFR.

4. The pharmaceutical composition of claim 3, comprising a molecule comprising SEQ ID NO: 20 and an antibody against Her-2.

* * * * *